US007943310B2

(12) United States Patent
Li et al.

(10) Patent No.: US 7,943,310 B2
(45) Date of Patent: May 17, 2011

(54) METHODS FOR ASSESSING RESPONSE TO THERAPY IN SUBJECTS HAVING ULCERATIVE COLITIS

(75) Inventors: Xilin Li, Wallingford, PA (US); Xiao-yu Song, Bridgewater, NJ (US)

(73) Assignee: Centocor Ortho Biotech Inc., Horsham, PA (US)

( * ) Notice: Subject to any disclaimer, the term of this patent is extended or adjusted under 35 U.S.C. 154(b) by 187 days.

(21) Appl. No.: 11/847,812

(22) Filed: Aug. 30, 2007

(65) Prior Publication Data
US 2009/0054253 A1 Feb. 26, 2009

Related U.S. Application Data

(60) Provisional application No. 60/823,983, filed on Aug. 30, 2006.

(51) Int. Cl.
*C12Q 1/68* (2006.01)
*C07H 21/02* (2006.01)
*C07H 21/04* (2006.01)
*C12P 19/34* (2006.01)

(52) U.S. Cl. ......... 435/6; 536/23.1; 536/23.5; 435/91.2; 435/91.21

(58) Field of Classification Search ........................ None
See application file for complete search history.

(56) References Cited

U.S. PATENT DOCUMENTS

| | | | |
|---|---|---|---|
| 5,328,470 A | 7/1994 | Nabel et al. | |
| 5,843,767 A | 12/1998 | Beattie | |
| 2002/0006622 A1 | 1/2002 | Bradley et al. | |
| 2006/0134663 A1 | 6/2006 | Harkin et al. | |
| 2008/0293582 A1* | 11/2008 | Li et al. ............................. | 506/9 |
| 2010/0069256 A1 | 3/2010 | Baribaud et al. | |

FOREIGN PATENT DOCUMENTS

| | | | |
|---|---|---|---|
| WO | WO 93/18186 A1 | 9/1993 | |
| WO | WO 01/94630 A2 | 12/2001 | |
| WO | WO2004/002417 A2 | 1/2004 | |
| WO | WO 2004/112589 | * 12/2004 | |
| WO | WO 2008/028044 A2 | 3/2008 | |

OTHER PUBLICATIONS

Liu et al. Clinical Immunology. 2004. 112: 225-230.*
Coleman et al. Drug Discovery Today. 2003. 8: 233-235.*
Saetre et al. Molecular Brain Research. 2004. 126: 198-206.*
Costello et al. PLoS Med. Aug. 23, 2005. 2(8): e199.*
Singh et al. Proceedings of the New Zealand Society of Animal Production. 2004. 64: 8-10.*
Csillag et al. Scandinavian Journal of Gastroenterology. 42(7): 834-840.*
Burczynski et al. Journal of Molecular Diagnostics. Feb. 2006. 8(1): 51-61 and Supplement Table S1.*
Affymetrix (Design and Performance of the GeneChip Human Genome U133 Plus 2.0 and Human Genome U133A 2.0 array. 2003-2004, available via url: <affymetrix.com>.*
Genecard for IL-24, available via url: <genecards.org>, printed Jul. 29, 2009.*
Genecard for OSM, available via url: <genecards.org>, printed Jul. 29, 2009.*
Genecard for PTGES, available via url: <genecards.org>, printed Jul. 29, 2009.*
Genecard for protocadherin 17, available via url: <genecards.org>, printed Jul. 29, 2009.*
GeneCard for CPA6, (available via url: <genecards.org>, printed Jul. 29, 2009.*
Rutgeerts et al. New England Journal of Medicine. 2005. 353: 2462-2476.*
Al-Sadi, et al., "Mechanism of IL-1{beta}-induced increase in intestinal epithelial tight junction permeability," J. Immunol. 2008:180:5653-5661.
Amasheh, et al., "Cytokine-dependent transcriptional down-regulation of epithelial sodium channel in ulcerative colitis," Gastroenterology, 2004: 126:1711-1720.
Balding, et al., "Inflammatory bowel disease: the role of inflammatory cytokine gene polymorphisms," Med. Inflam. 2004:13:181-187.
Banks, et al., "Chemokine expression in IBD. Mucosal chemokine expression is unselectively increased in both ulcerative colitis and Crohn's disease," J. Pathol. 2003:199:28-35.
Ben-Baruch, et al., "Signals and receptors involved in recruitment of inflammatory cells," J. Biol. Chem. 1995: 270:11703-11706.
Bermejo, et al., "Adaptive soft k-nearest-neighbor classifiers," Pattern Recog. 2000: 33:1999-2005.
Braegger, et al., "Tumour necrosis factor alpha in stool as a marker of intestinal inflammation," Lancet 1992: 339:389.
Brun, et al., "Increased intestinal permeability in obese mice: new evidence in the pathogenesis of nonalcoholic steatohepatitis," Am. J. Physiol. Gastrointest. Liver Physiol. 2007:292:G518-G525.
Burdzynski, et al., "Molecular Classification of Crohn's Disease and Ulcerative Colitis Patients Using Transcriptional Profiles in Peripheral Blood Mononuclear Cells," Journal of Molecular Diagnostics, 2006: 8(1): 51-61.
Chen, et al., "Gene therapy for brain tumors: Regression of experimental gliomas by adenovirus-mediated gene transfer in vivo," Proc. Natl. Acad. Sci. USA. 1994: 91: 3054-3057.
Colliver, et al., "Molecular profiling of ulcerative colitis-associated neoplastic progression," Experimental and Molecular Pathology, 2005: 80(1): 1-10.
Comelli, et al., "Biomarkers of human gastrointestinal tract regions," Mamm. Genome, 2009: 20: 516-527.
Craig, et al., "Removal of repetitive sequences from FISH probes using PCT-assisted affinity chromatography," Hum. Genet. 2007: 100:472-476.
Cruikshank, et al., "A Lipidated Anti-Tat Antibody Enters Living Cells and Blocks HIV-1 Viral Replica," Journal of Acquired Immune Deficiency Syndromes and Human Retrovirology, 1997: 14(3): 193-203.
Frolova, et al., "Expression of Toll-like Receptor 2 (TLR2), TLR4, and CD14 in Biopsy Samples of Patients With Inflammatory Bowel Diseases: Upregulated Expression of TLR2 in Terminal Ileum of Patients With Ulcerative Colitis," J. Histochem. Cytochem. 2008:56:267-274.

(Continued)

*Primary Examiner* — Carla Myers
(74) *Attorney, Agent, or Firm* — Eric Dichter

(57) ABSTRACT

A method for prognostic or diagnostic assessment of a gastrointestinal-related disorder, such as ulcerative colitis, in a subject correlates the presence, absence, and/or magnitude of a gene in a sample with a reference standard to determine the presence and/or severity of the disorder, and/or the response to treatment for the disorder. The method enables identification of the effectiveness of candidate therapies.

12 Claims, No Drawings

OTHER PUBLICATIONS

Geboes et al., "A reproducible grading scale for histological assessment of inflammation in ulcerative colitis," Gut 2000:47:404-409.
Greenberg, et al., "Phagocytosis and innate immunity," Curr. Opin. Immunol. 2002:14:136-145.
Guo, et al., "Role of C5a—C5ar interaction in sepsis," Shock 2004:21:1-7.
Hanauer, et al., Maintenance infliximab for Crohn's disease: the ACCENT I randomised trial. Lancet 2002: 359:1541-1549.
Hart, et al., "Characteristics of Intestinal Dendritic Cells in Inflammatory Bowel Diseases," Gastroenterology 2005:129:50-65.
Hayashi, et al., "Toll-like receptors stimulate human neutrophil function," Blood 2003:102:2660-2669.
Hughes, et al., "Expression Profiling of Wnt Family of Genes in Normal and Inflammatory Bowel Disease Primary Human Intestinal Myofibroblasts and Normal Human Colonic Crypt Eipthelial Cells," Inflammatory Bowel Disease 2010:1-8.
Izzo, et al., "Interleukin-8 and neutrophils markers in colonic mucosa from patients with ulcerative colitis," Am. J. Gastroenterol .1992:87:1447-1452.
Klein, et al., "A polymorphism in the IL11 gene is associated with ulcerative colitis," Genes Immun. 2002:3:494-496.
Kusam, et al., "Inhibition of Th2 differentiation and GATA-3 expression by BCL-6," J. Immunol. 2003:170:2435-41.
Leeb, et al., "Reduced migration of fibroblasts in inflammatory bowel disease: role of inflammatory mediators and focal adhesion kinase," Gastroenterology, 2003: 125:1341-1354.
Linder, et al., "Pharmacogenetics: a laboratory tool for optimizing therapeutic efficiency," Clin. Chem, 1997: 43(2): 254-266.
Liu, et al., "Regulation of leukocyte transmigration: cell surface interactions and signaling events," J. Immunol. 2004:172:7-13.
Melgar, et al., "Over-expression of interleukin 10 in mucosal T cells of patients with active ulcerative colitis," Clin. Exp. Immunol. 2003: 134:127-137.
Mesko, et al., "Peripheral blood gene expression patterns discriminate among chronic inflammatory diseases and healthy controls and identify novel targets," BMC Medical Genomics 3: 1-15(2010).
Mizoguchi, et al., "Role of tumor necrosis factor receptor 2 (TNFR2) in colonic epithelial hyperplasia and chronic intestinal inflammation in mice," Gastroenterology, 2002: 122:134-144.
Murch, et al., "Serum concentrations of tumour necrosis factor alpha in childhood chronic inflammatory bowel disease," Gut 1991: 32:913-917.
Murch, et al., "Location of tumour necrosis factor alpha by immunohistochemistry in chronic inflammatory bowel disease," Gut 1993: 34:1705-1709.
Noble, et al., "Regional variation in gene expression in the healthy colon is dysregulated in ulcerative colitis," Gut 57(10): 1398-1405 (2008).
Okahara, et al., "Inflammatory gene signature in ulcerative colitis with cDNA macroarray analysis," Aliment Pharmacol. Ther. 2005: 21:1091-1097.
Olsen, et al., "Diagnosis of Ulcerative Colitis Before Onset of Inflammation of Multivariate Modeling of Genome-wide Gene Expression Data," Inflammatory Bowel Disease, 2009: 15: 1032-1038.
Pender, et al., "Matrix metalloproteinases and the gut—new roles for old enzymes"_Curr. Opin. Pharmacol. 2004:4:546-550.
Ramos, et al., "Neutrophil migration induced by IL-8-activated mast cells is mediated by CINC-1," Cytokine 2003:21:214-223.
Raunch, et al, "Quantitative microscopy after fluorescence in situ hybridization—a comparison between repeat-depleted and non-depleted DNA probes,"J. Biochem, Biophys. Methods, 2000:44:59-72.
Rutgeerts, et al., "Comparison of scheduled and episodic treatment strategies of infliximab in Crohn's disease," Gastroenterology 2004:126:402-413.
Rutgeerts, et al., "Infliximab for indiction and maintenane therapy for ulcerative colitis," N.Engl. J. Med. 2005: 353:2462.
Rybaczyk, et al., "New Bionformatics Approach to Analyze Gene Expressions and Signaling Pathways Reveals Unique Purine Gene Dysregulation Profiles that Distinguish Between CD and UC," Inflammatory Bowel Disease 2009: 15(7): 971-984.
Sands, et al., "Infliximab maintenance therapy for fistulizing Crohn's disease," N. Engl. J. Med. 2004, 350:879-885.
Sands, et al., "Long-term treatment of rectovaginal fistulas in Crohn's disease: response to infliximab in the ACCENT II Study," Clin. Gastroenterol. Hepatol. 2004, 2:912-920.
Ten Hove, et al., "Expression of CD45RB functionally distinguishes intestinal T Lymphocytes in inflammatory bowel disease," J. Leukoc. Biol. 2004, 75:1010-1015.
Ufer, et al., "Decreased sigmoidal ABCB1 (P-glycoprotein) expression in ulcerative colitis is associated with disease activity," Pharmacogenomics, 2009, 10(12): 1941-1953.
Von Stein, et al., "Multigene Analysis Can Discriminate Between Ulcerative Colitis, Crohn's Disease, and Irritable Bowel Syndrome," Gastroentrology, 2008: 134(7): 1869-1881.
Wu, et al., "Genome-wide Gene Expression Differences in Crohn's Disease and Ulcerative Colitis from Endoscopic Pinch Biopsies: Insights into Distinctive Pathogensis," Inflammatory Bowel Disease. 2007, 13: 807-821.
Yamamoto, et al., "Systemic and local cytokine production in quiescent ulcerative colitis and its relationship to future relapse: a prospective pilot study" Inflamm. Bowel Dis. 2005;11:589-596.
Ye, et al., "The BCL-6 proto-oncogene controls germinal-centre formation and Th2-type," Inflamm. Nat. Genet. 1997;16:161-70.

* cited by examiner

METHODS FOR ASSESSING RESPONSE TO THERAPY IN SUBJECTS HAVING ULCERATIVE COLITIS

CLAIM TO PRIORITY

This application claims the benefit of U.S. Provisional Application Ser. No. 80/823,983, filed 30 Aug. 2006, the entire contents of which is incorporated herein by reference in its entirety.

FIELD OF THE INVENTION

The invention relates to the identification of expression profiles and the nucleic acids indicative of gastrointestinal-related disorders, such as ulcerative colitis, and to the use of such expression profiles and nucleic acids in diagnosis of ulcerative colitis and related diseases. The invention further relates to methods for identifying, using, and testing candidate agents and/or targets which modulate ulcerative colitis.

BACKGROUND OF THE INVENTION

Ulcerative colitis (UC) is a multifactorial autoimmune disease with a complex pathogenesis involving unidentified genetic, microbial, and environmental factors. Recent studies using microarray analysis of inflamed colonoscopic tissue biopsy vs. non-inflamed biopsy samples from UC patients revealed dysregulation of a few inflammatory cytokines (1), however, the etiology, pathogenesis, and role of tumor necrosis factor-alpha (TNFα) in UC is still poorly understood. TNFα is a critical proinflammatory cytokine in Crohn's disease as demonstrated by the therapeutic effect of infliximab on the induction and maintenance of clinical remission, closure of enterocutaneous, perianal, and rectovaginal fistulas, maintenance of fistula closure, and steroid tapering in Crohn's disease patients (2-5). However, the evidence to support a role of TNFα in the pathogenesis of UC has been controversial (6-10) despite the fact that it is also found at increased levels in the blood, colonic tissue, and stools of UC patients (11-13), A recent clinical study (ACT-1) by Rutgeerts et al. showed that infliximab is effective when administered at weeks 0, 2, 6 and every 8 weeks thereafter in achieving clinical response and remission in patients with moderate-to-severe active UC despite the use of conventional therapy supporting a critical pathogenic role of TNFα in UC (14).

Microarray technology is a powerful tool since it enables analysis of the expression of thousands of genes simultaneously and can also be automated allowing for a high-throughput format. In diseases associated with complex host functions, such as those known as immune mediated inflammatory diseases, such as UC, microarray results can provide a gene expression profile that can be of utility in designing new approaches to disease diagnosis and management. These approaches also serve to identify novel genes and annotating genes of unknown function heretofore unassociated with the disease or condition. Accordingly, there is a need to identify and characterize new gene markers useful in developing methods for diagnosing and treating autoimmune disorders, such as UC and Crohn's disease, as well as other diseases and conditions and how a patient would respond to a therapeutic intervention.

Gene expression can be modulated in several different ways, including by the use of siRNAs, shRNAs, antisense molecules and DNAzymes, SiRNAs and shRNAs both work via the RNAi pathway and have been successfully used to suppress the expression of genes. RNAS was first discovered in worms and the phenomenon of gene silencing related to dsRNA was first reported in plants by Fire and Mello and is thought to be a way for plant cells to combat infection with RNA viruses, in this pathway, the long dsRNA viral product is processed into smaller fragments of 21-25 bp in length by a DICER-like enzyme and then the double-stranded molecule is unwound and loaded into the RNA induced silencing complex (RISC). A similar pathway has been identified in mammalian cells with the notable difference that the dsRNA molecules must be smaller than 30 bp in length in order to avoid the induction of the so-called interferon response, which is not gene specific and leads to the global shut down of protein synthesis in the cell.

Synthetic siRNAs have been successfully designed to selectively target a single gene and can be delivered to cells in vitro or in vivo, ShRNAs are the DNA equivalents of siRNA molecules and have the advantage of being incorporated into a cells' genome where they are replicated during every mitotic cycle.

DNAzymes have also been used to modulate gene expression. DNAzymes are catalytic DNA molecules that cleave single-stranded RNA. They are highly selective for the target RNA sequence and as such can be used to down-regulate specific genes through targeting of the messenger RNA.

Accordingly, there is a need to identify and characterize new gene markers useful in developing methods for diagnosing and treating autoimmune disorders, such as UC and Crohn's disease, as well as other diseases and conditions.

SUMMARY OF THE INVENTION

The present invention relates to a method of diagnosing and/or treating UC and/or related diseases or disorders by identifying and using candidate agents and/or targets which modulate such diseases or disorders. The present invention includes the discovery of panels of genes, one of 66 genes that have modified expression levels in patients with UC and/or treated with an agent effective in reducing the symptoms of UC (and modified levels in patients whose UC treatment has not been effective). The modified expression levels constitute a profile that can serve as a biomarker profile indicative of UC and/or the response of a subject to treatment.

In a particular embodiment, the present invention comprises a method of determining the efficacy of the treatment for UC based on the pattern of gene expression of one or more of the 68 genes which constitute the profile. One or more of these genes may be from a category of genes, for example, an innate or adaptive immune response-related gene, a cell-cell interaction, cell-matrix interaction or matrix regulation-related gene, a cell-cell, intracellular signaling pathway-related gene, a cell growth and apoptosis-related gene, a protein regulation-related gene, a metabolic regulation-related gene, a cytoskeleton organization-related gene, a developmental regulation-related gene, and a transcriptional regulation-related gene. This can be done for a subject, for example, prior to the manifestation of other gross measurements of clinical response, in one embodiment, the method of screening drug candidates includes comparing the level of expression in the absence of the drug candidate to the level of expression in the presence of the drug candidate, wherein the concentration of the drug candidate can vary when present, and wherein the comparison can occur during treatment or after treatment with the drug candidate. In a typical embodiment, the cell specimen expresses at least two expression profile genes. The profile genes may show an increase or decrease.

In one embodiment, the UC-related gene profile is used to create an array-based method for prognostic or diagnostic purposes, the method comprising;
- (a) preparing a representative mixture of nucleic acids from a specimen obtained from a patient and causing said sample nucleic acids in the mixture to be labeled with a detectable marker;
- (b) contacting a sample with an array comprising a plurality of nucleic acid segments, wherein each nucleic acid segment is immobilized to a discrete and known address on a substrate surface wherein the panel of UC-related biomarkers is identified as a feature of the array by address, the array further comprises at least one calibration nucleic acid at a known address on the substrate, and contacting is performed under conditions in which a sample nucleic acid specifically may bind to the nucleic acid segment immobilized on the arrays;
- (c) performing a statistical comparison of all test samples from treated patients and a reference standard; and
- (d) comparing the pattern of intensity changes in features for the test sample to the pattern of intensity changes for those features which are members of the UC-related gene profile with historical patterns for samples taken from patients responsive to treatment with an anti-TNF antibody.

Optionally, statistical analysis is performed on the changes in levels of members of the gene panel to evaluate the significance of these changes and to identify which members are meaningful members of the panel.

In an alternative embodiment, the present invention comprises a kit for diagnosing UC and/or related diseases or disorders by identifying and using candidate agents and/or targets which modulate such diseases or disorders and for determining the efficacy of the treatment for UC and/or related diseases or disorders based on the pattern of gene expression.

Another embodiment of the present invention relates to agonists and/or antagonists of the transcription of the genes or of the gene products of the UC-related gene panel and a method of using UC-related gene panel antagonists, including antibodies directed toward UC-related gene panel products, to treat UC or related disorders.

In one aspect, the UC-related gene panel antagonist is an antibody that specifically binds UC-related gene panel product. A particular advantage of such antibodies is that they are capable of binding UC-related gene panel product in a manner that prevents its action. The method of the present invention thus employs antibodies having the desirable neutralizing property which makes them ideally suited for therapeutic and preventative treatment of disease states associated with various UC-related disorders in human or nonhuman patients. Accordingly, the present invention is directed to a method of treating UC or a related disease or condition in a patient in need of such treatment which comprises administering to the patient an amount of a neutralizing UC-related gene panel product antibody to inhibit the UC-related disease or condition.

In another aspect, the invention provides methods for modulating activity of a member of a UC-related gene panel comprising contacting a cell with an agent (e.g., antagonist or agonist) that modulates (inhibits or enhances) the activity or expression of the member of the UC-related gene panel such that activity or expression in the cell is modulated, in a preferred embodiment, the agent is an antibody that specifically binds to the UC-related gene panel. In other embodiments, the modulator is a peptide, peptidomimetic, or other small molecule.

The present invention also provides methods of treating a subject having UC or related disorder wherein the disorder can be ameliorated by modulating the amount or activity of the UC-related gene panel. The present invention also provides methods of treating a subject having a disorder characterized by aberrant activity of the UC-related gene panel product or one of their encoding polynucleotide by administering to the subject an agent that is a modulator of the activity of the UC-related gene panel product or or a modulator of the expression of a UC-related gene panel.

In one embodiment, the modulator is a polypeptide or small molecule compound. In another embodiment, the modulator is a polynucleotide. In a particular embodiment, the UC-related gene panel antagonist is an siRNA molecule, an shRNA molecule, an antisense molecule, a ribozyme, or a DNAzyme capable of preventing the production of UC-related gene panel by cells.

The present invention further provides any invention described herein.

DETAILED DESCRIPTION OF THE INVENTION

Definitions

The following definitions are set forth to illustrate and define the meaning and scope of various terms used to describe the invention herein.

An "activity," a biological activity, and a functional activity of a polypeptide refers to an activity exerted by a gene of the UC-related gene panel in response to its specific interaction with another protein or molecule as determined in vivo, in situ, or in vitro, according to standard techniques. Such activities can be a direct activity, such as an association with or an enzymatic activity on a second protein, or an indirect activity, such as a cellular process mediated by interaction of the protein with a second protein or a series of interactions as in intracellular signaling or the coagulation cascade.

An "antibody" includes any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. For example, antibody fragments include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, and single domain antibodies (e.g., $V_H$ or $V_L$), are encompassed by the invention (see, e.g., Colligan, et al., eds., Current Protocols in Immunology, John Wiley & Sons. Inc., NY (1994-2001); Colligan et al., Current Protocols in Polypeptide Science, John Wiley & Sons, NY (1997-2001)).

The terms "array" or "microarray" or "biochip" or "chip" as used herein refer to articles of manufacture or devices comprising a plurality of immobilized target elements, each target element comprising a "clone," "feature," "spot" or defined area comprising a particular composition, such as a biological molecule, e.g., a nucleic acid molecule or polypeptide, immobilized to a solid surface, as discussed in further detail, below.

"Complement of" or "complementary to" a nucleic acid sequence of the invention refers to a polynucleotide molecule having a complementary base sequence and reverse orientation as compared to a first polynucleotide.

A "gene" is a set of segments of nucleic acid that contains the information necessary to produce a functional RNA product in a controlled manner. By "gene" is meant a DNA sequence capable of being transcribed to produce a unique gene product, which product will usually be a protein synthesized from the transcribed, properly processed, and translated gene sequence. Some genes encode gene products that are transcribed but not translated, such as rRNA genes and tRNA genes. Gene expression, or simply "expression", is the process by which the inheritable information which comprises a gene, such as the DNA sequence, is made manifest as a biologically functional gene product, such as protein or RNA. The genes of eukaryotic organisms can contain non-coding regions called introns that are removed from the messenger RNA in a process known as splicing. Exons are the regions that encode the gene product. One single gene can lead to the synthesis of multiple proteins through the different arrangements of exons produced by alternative splicings. Several steps in the gene expression process may be modulated, including the transcription step and mRNA processing step(s). The level of gene expression can have a profound effect on the functions (actions) of the gene and therefore of the gene product in the organism, A gene may exist in one of multiple alternative forms, each of which is a viable DNA sequence occupying a given position, or locus on a chromosome known as alleles with nucleic acid variations which may produce changes in the encoded protein gene product or, by virtue of the redundancy in the genetic code, be silent. Thus, DNA fragments representative of a single gene may comprise variations in length of the segment or variations in sequence.

"identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov. M, and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (informax, Frederick, Md.).

The terms "specifically hybridize to," "hybridizing specifically to," "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence; and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Alternative hybridization conditions that can be used to practice the invention are described in detail, below, in alternative aspects, the hybridization and/or wash conditions are carried out under moderate conditions, stringent conditions and very stringent conditions, as described in further detail, below. Alternative wash conditions are also used in different aspects, as described in further detail, herein.

The phrases "labeled biological molecule" or "labeled with a detectable composition" or "labeled with a detectable moiety" as used herein refer to a biological molecule, e.g., a nucleic acid, comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label) into the nucleic acid by, e.g., nick translation, random primer extension, amplification with degenerate primers, and the like. Any label can be used, e.g., chemiluminescent labels, radiolabes, enzymatic labels and the like. The label can be detectable by any means, e.g., visual, spectroscopic, photochemical, biochemical, immunochemical, physical, chemical and/or chemiluminescent detection. The invention can use arrays comprising immobilized nucleic acids comprising detectable labels.

The term "nucleic acid" as used herein refers to a deoxyribonucleotide (DNA) or ribonucleotide (RNA) in either single- or double-stranded form. The term encompasses nucleic acids containing known analogues of natural nucleotides. The term nucleic acid is used interchangeably with gene, DNA, RNA, cDNA, mRNA, oligonucleotide primer, probe and amplification product. The term also encompasses DNA backbone analogues, such as phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs).

The terms "sample" or "sample of nucleic acids" as used herein refer to a sample comprising a DNA or RNA, or nucleic acid representative of DNA or RNA isolated from a natural source. A "sample of nucleic acids" is in a form suitable for hybridization (e.g., as a soluble aqueous solution) to another nucleic acid (e.g., immobilized probes). The sample nucleic acid may be isolated, cloned, or extracted from particular cells or tissues. The cell or tissue sample from which the nucleic acid sample is prepared is typically taken from a patient having or suspected of having UC or a related disease or condition. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves taken from patients or from ceil cultures, cells from tissue culture and other media in which it may be desirable to detect the response to drug candidates. In some cases, the nucleic acids may be amplified using standard techniques such as PCR, prior to the hybridization. The probe an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., SACs, PACs, YACs, and the like (see below).

"Nucleic acids" are polymers of nucleotides, wherein a nucleotide comprises a base linked to a sugar which sugars are in turn linked one to another by an interceding at least bivalent molecule, such as phosphoric acid. In naturally occurring nucleic acids, the sugar is either 2'-deoxyribose (DNA) or ribose (RNA). Unnatural poly- or oliogonucleotides contain modified bases, sugars, or linking molecules, but are generally understood to mimic the complementary nature of the naturally occurring nucleic acids after which they are designed. An example of an unnatural oligonucleotide is an antisense molecule composition that has a phosphorothiorate backbone. An "oligonucleotide" generally refers to a nucleic acid molecule having less than 30 nucleotides.

The term "profile" means a pattern and relates to the magnitude and direction of change of a number of features. The profile may be interpreted stringently, i.e., where the variation in the magnitude and/or number of features within the profile displaying the characteristic is substantially similar to a reference profile or it may be interpreted less stringently, for example, by requiring a trend rather than an absolute match of all or a subset of feature characteristics.

The terms "protein," "polypeptide," and "peptide" include "analogs," or "conservative variants" and "mimetics" or "peptidomimetics" with structures and activity that substantially correspond to the polypeptide from which the variant was derived, as discussed in detail above.

A "polypeptide" is a polymer of amino acid residues joined by peptide bonds, and a peptide generally refers to amino acid polymers of 12 or less residues. Peptide bonds can be produced naturally as directed by the nucleic acid template or synthetically by methods well known in the art.

A "protein" is a macromolecule comprising one or more polypeptide chains. A protein may further comprise substituent groups attached to the side groups of the amino acids not involved in formation of the peptide bonds. Typically, proteins formed by eukaryotic cell expression also contain carbohydrates. Proteins are defined herein in terms of their amino acid sequence or backbone and substituents are not specified, whether known or not.

The term "receptor" denotes a molecule having the ability to affect biological activity, in e.g., a cell, as a result of interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. Non-cell associated receptors are termed soluble receptor's or ligands.

All publications or patents cited herein are entirely incorporated herein by reference, whether or not specifically designated accordingly, as they show the state of the art at the time of the present invention and/or provide description and enablement of the present invention. Publications refer to any scientific or patent publications, or any other information available in any media format, including ail recorded, electronic or printed formats. The following references are entirely incorporated herein by reference; Ausubel, et al., ed., Current Protocols in Molecular Biology, John Wiley & Sons, inc., NY (1987-2001): Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY (1997-2001).

Gene Panel Identification and Validation

The present invention provides novel methods for diagnosis of disorders associated with UC, as well as methods for screening for compositions which modulate the symptoms of UC, particularly the mucosal layer of the rectum and all or part of the colon. By "UC" or grammatical equivalents as used herein, is meant a disease state or condition which is marked by diarrhea, rectal bleeding, tenesmus, passage of mucus, and crampy abdominal pain.

In one aspect, the expression levels of genes are determined in different patient samples for which diagnosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the patient sample. That is, normal tissue may be distinguished from lesion tissue and tissue from a treated patient may be distinguished from an untreated patient. By comparing expression profiles of tissue in different disease states that are known, information regarding which genes are important (including both up- and down-regulation of genes) in each of these states is obtained.

The identification of sequences (genes) that are differentially expressed in disease tissue allows the use of this information in a number of ways. For example, the evaluation of a particular treatment regime may be evaluated. Similarly, diagnosis may be done or confirmed by comparing patient samples with the known expression profiles. Furthermore, these gene expression profiles (or individual genes) allow screening of drug candidates with an eye to mimicking or altering a particular expression profile; for example, screening can be done for drugs that suppress the angiogenic expression profile.

This may be done by making biochips comprising sets of the important disease genes, which can then be used in these screens. These methods can also be performed on the protein basis; that is, protein expression levels of the UC-related gene product proteins can be evaluated for diagnostic purposes or to screen candidate agents. In addition, the nucleic acid sequences comprising the UC-related gene profile can be used to design a therapeutic including the administration of antisense nucleic acids, or the protein coded for by the gene sequence can be administered as a component of a vaccine.

Thus, the present invention provides information on nucleic acid and protein sequences that are differentially expressed in UC, herein termed "UC-related gene sequences," As outlined below, UC-related gene sequences include those that are upregulated (i.e., expressed at a higher level) in disorders associated with UC, as well as those that are down-regulated (i.e., expressed at a lower level). In a preferred embodiment, the UC-related gene sequences are from humans; however, as will be appreciated by those in the art, UC-related gene sequences from other organisms may be useful in animal models of disease and drug evaluation: thus, other UC-related gene sequences are provided, from vertebrates, including mammals, including rodents (rats, mice, hamsters, guinea pigs, etc.), primates, farm animals (including sheep, goats, pigs, cows, horses, etc). UC-related gene sequences from other organisms may be obtained using the techniques known in the art.

UC-related gene sequences can include both nucleic acid and amino acid sequences. In a preferred embodiment, the UC-related gene sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus, an isolated nucleic acid, in a linear form, or an expression vector formed in vitro by ligating DMA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

Method of Practicing the Invention

The invention provides in silico, array-based methods relying on the relative amount of a binding molecule (e.g., nucleic acid sequence) in two or more samples. Also provided are computer-implemented methods for determining the relative amount of a binding molecule (e.g., nucleic acid sequence) in two or more samples and using the determined relative binding amount to diagnose and stage disease, predict responsiveness to a particular therapy, and monitor and enhance therapeutic treatment.

In practicing the methods of the invention, two or more samples of labeled biological molecules (e.g., nucleic acid) are applied to two or more arrays, where the arrays have substantially the same complement of immobilized binding molecule (e.g., immobilized nucleic acid capable of hybridizing to labeled sample nucleic acid). The two or more arrays are typically multiple copies of the same array. However, because each "spot," "clone" or "feature" on the array has similar biological molecules (e.g., nucleic acids of the same sequence) and the biological molecules (e.g., nucleic acid) in each spot is known, as is typical of nucleic acid and other arrays, it is not necessary that the multiple arrays used in the invention be identical in configuration it is only necessary that the position of each feature on the substrate be known, that is, have an address. Thus, in one aspect, multiple biological molecules (e.g., nucleic acid) in samples are comparatively bound to the array (e.g., hybridized simultaneously) and the information gathered is coded so that the results are based on the inherent properties of the feature (e.g., the nucleic acid sequence) and not it's position on the substrate.

Amplification of Nucleic Acids

Amplification using oligonucleotide primers can be used to generate nucleic acids used in the compositions and methods of the invention, to detect or measure levels of test or control samples hybridized to an array, and the like. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:569; Landegren (1988) Science 241:1077; Barringer (1990) Gene 89:117); transcription amplification (see, e.g., Kwoh (1989) Proc. Natl. Acad. Sci., USA 86:1173); and, self-sustained sequence replication (see, e.g., Guatelli (1990) Proc. Natl. Acad. Sci. USA 87:1874), Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-318; Sambrook; Ausubel; U.S. Pat. Nos. 4,883,195 and 4,683,202; Sooknanan (1995) Biotechnology 13:563-564.

Hybridizing Nucleic Acids

In practicing the methods of the invention, test and control samples of nucleic acid are hybridized to immobilized probe nucleic acid, e.g., on arrays. In alternative aspects, the hybridization and/or wash conditions are carried out under moderate conditions, stringent conditions and very stringent conditions. An extensive guide to the hybridization of nucleic acids is found in, e.g., Sambrook Ausubel, Tijssen. Generally, highly stringent hybridization and wash conditions are selected to be about 5° C. Sower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or a filter in a Southern or northern blot is 42° C. using standard hybridization solutions (see, e.g., Sambrook), with the hybridization being carried out overnight. An example of highly stringent wash conditions is 0.15 M NaCl at 72° C. for about 15 minutes. An example of stringent wash conditions is a 0.2× SSC wash at 65° C. for 15 minutes (see, e.g., Sambrook). Often, a high stringency wash is preceded by a medium or low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

In alternative aspects of the compositions and methods of the invention, e.g., in practicing comparative nucleic acid hybridization, such as comparative genomic hybridization (CGH) with arrays, the fluorescent dyes Cy3® and Cy5® are used to differentially label nucleic acid fragments from two samples, e.g., the array-immobilized nucleic acid versus the sample nucleic acid, or, nucleic acid generated from a control versus a test cell or tissue. Many commercial instruments are designed to accommodate the detection of these two dyes. To increase the stability of Cy5®, or fluors or other oxidation-sensitive compounds, antioxidants and free radical scavengers can be used in hybridization mixes, the hybridization and/or the wash solutions. Thus, Cy5® signals are dramatically increased and longer hybridization times are possible. See WO 0194630 A2 and U.S. Patent Application No. 20020006622.

To further increase the hybridization sensitivity, hybridization can be carried out in a controlled, unsaturated humidity environment; thus, hybridization efficiency is significantly improved if the humidity is not saturated. See WO 0194630 A2 and U.S. Patent Application No. 20020006622. The hybridization efficiency can be improved if the humidify is dynamically controlled, i.e., if the humidity changes during hybridization. Mass transfer will be facilitated in a dynamically balanced humidity environment. The humidity in the hybridization environment can be adjusted stepwise or continuously. Array devices comprising housings and controls that allow the operator to control the humidity during pre-hybridization, hybridization, wash and/or detection stages can be used. The device can have detection, control and memory components to allow pre-programming of the humidity and temperature controls (which are constant and precise or which flucturate), and other parameters during the entire procedural cycle, including pre-hybridization, hybridization, wash and detection steps. See WO 0194630 A2 and U.S. Patent Application No. 20020006622.

The methods of the invention can comprise hybridization conditions comprising osmotic fluctuation. Hybridization efficiency (i.e., time to equilibrium) can also be enhanced by a hybridization environment that comprises changing hyper-Zhypo-tonicity, e.g., a solute gradient. A solute gradient is created in the device. For example, a low salt hybridization solution is placed on one side of the array hybridization chamber and a higher salt buffer is placed on the other side to generate a solute gradient in the chamber. See WO 0194630 A2 and U.S. Patent Application No. 20020006622.

Blocking the Ability of Repetitive Nucleic Acid Sequences to Hybridize

The methods of the invention can comprise a step of blocking the ability of repetitive nucleic acid sequences to hybridize (i.e., blocking "hybridization capacity") in the immobilized nucleic acid segments. The hybridization capacity of repetitive nucleic acid sequences in the sample nucleic acid sequences can be blocked by mixing sample nucleic acid sequences with unlabeled or alternatively labeled repetitive nucleic acid sequences. Sample nucleic acid sequences can be mixed with repetitive nucleic acid sequences before the step of contacting with the array-immobilized nucleic acid segments. Blocking sequences are for example, Cot-1 DNA, salmon sperm DNA, or specific repetitive genomic sequences. The repetitive nucleic acid sequences can be unlabeled. A number of methods for removing and/or disabling the hybridization capacity of repetitive sequences using, e.g., Cot-1 are known; see, e.g., Craig (1997) Hum. Genet. 100: 472-476; WO 93/18186. Repetitive DNA sequences can be removed from library probes by means of magnetic purification and affinity PCR, see, e.g., Rauch (2000) J. Biochem. Biophys. Methods 44:59-72.

Arrays are genetically a plurality of target elements immobilized onto the surface of the plate as defined "spots" or "clusters," or "features," with each target element comprising one or more biological molecules (e.g., nucleic acids or polypeptides) immobilized to a solid surface for specific binding (e.g., hybridization) to a molecule in a sample. The immobilized nucleic acids can contain sequences from specific messages (e.g., as cDNA libraries) or genes (e.g., genomic libraries), including a human genome. Other target elements can contain reference sequences and the like. The biological molecules of the arrays may be arranged on the solid surface at different sizes and different densities. The densities of the biological molecules in a cluster and the number of clusters on the array will depend upon a number of factors, such as the nature of the label, the solid support, the degree of hydropbobicity of the substrate surface, and the like. Each feature may comprise substantially the same biological molecule (e.g., nucleic acid), or, a mixture of biological molecules (e.g., nucleic acids of different lengths and/or sequences). Thus, for example, a feature may contain more than one copy of a cloned piece of DNA, and each copy may be broken into fragments of different lengths.

Array substrate surfaces onto which biological molecules (e.g., nucleic acids) are immobilized can include nitrocellulose, glass, quartz, fused silica, plastics and the like, as discussed further, below. The compositions and methods of the invention can incorporate in whole or in part designs of arrays, and associated components and methods, as described, e.g., in U.S. Pat. Nos. 6,344,316; 8,197,503; 6,174, 864; 8,159,685; 6,156,501; 6,093.370; 6,087,112; 6,087,103; 6,087,102; 6,083,697; 6,080,585; 6,054,270; 6,048,695; 6,045,996; 6,022,963; 6,013,440; 5,959,098; 5,856,174; 5,843,655; 5,837,832; 5,770,456; 5,723,320; 5,700,637; 5,695,940; 5,556,752; 5,143,854; see also, e.g., WO 99/51773; WO 99/09217; WO 97/46313; WO 96/17958; WO 89/10977; see also, e.g., Johnston (1998) Curr. Biol. 8:R171-174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32; Epstein (2000) Current Opinion in Biotech. 11:36-41; Mendoza (1999 Biotechniques 27: 778-788; Lueking (1999) Anal. Biochem. 270:103-111; Davies (1999) Biotechniques 27:1258-1261.

Substrate Surfaces

Substrate surfaces that can be used in the compositions and methods of the invention include, for example, glass (see, e.g., U.S. Pat. No. 5,843,767), ceramics, and quartz. The arrays can have substrate surfaces of a rigid, semi-rigid or flexible material. The substrate surface can be flat or planar, be shaped as wells, raised regions, etched trenches, pores, beads, filaments, or the like. Substrate surfaces can also comprise various materials such as nitrocellulose, paper, crystalline substrates (e.g., gallium arsenide), metals, metalloids, polacryloylmorpholide, various plastics and plastic copolymers, Nylon®, Teflon®, polyethylene, polypropylene, latex, polymethacrylate, polyethylene terephthalate), rayon, nylon, poly(vinyl butyrate), and cellulose acetate. The substrates may be coated and the substate and the coating may be functionalized to, e.g., enable conjugation to an amine.

Arrays Comprising Sequences Representative of Human Genes

As genomic DMA comprises nucleic acid sequences that do not code for gene products, e.g. sequences involved in gene regulation and intervening sequences (introns), arrays comprising discreet probes or DNA fragments representative of exons of a gene which are expressed and form functional gene products may used rather than arrays created e.g. from random fragmentation of a genome or chromosome.

in one embodiment, a DNA chip comprising DNA fragments which representative of coding sequences of specified genetic loci, preferably specific named genes, are used to detect the expression patterns of genes from samples of UC patients. One example of such a commercially available DNA chip is the Human Genome U133 (MG-U133) Set, consisting of two GeneChip® arrays, available from Affymetrix (Sunnyvale, Calif.). The Human Genome U133 contains almost 45,000 probe sets representing more than 39,000 transcripts derived from approximately 33,000 well-substantiated human genes. According to the documentation available from Affymetrix, the Human Genome U133 set design uses sequences selected from GenBank®, dbEST, and RefSeq. The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release). While some commercially available gene chips are useful for research purposes, similar arrays using probe sets of oligonucleotides or DNA fragments representative of the UC-gene product panels of the present invention for detecting gene expression related to the treatment, prediction, or diagnosis of UC can be manufactured based on the techniques described in U.S. Pat. Nos. 7,135,265, 6,610,482, 5,800,992, and 6,054,270.

Arrays Comprising Calibration Sequences

The invention contemplates the use of arrays comprising immobilized calibration sequences for normalizing the results of array-based hybridization reactions, and methods for using these calibration sequences, e.g., to determine the copy number of a calibration sequence to "normalize" or "calibrate" ratio profiles. The calibration sequences can be substantially the same as a unique sequence in an immobilized nucleic acid sequence on an array. For example, a "marker" sequence from each "spot" or "biosite" on an array (which is present only on that spot, making it a "marker" for that spot) is represented by a corresponding sequence on one or more "control" or "calibration" spot(s).

The "control spots" or "calibration spots" are used for "normalization" to provide information that is reliable and repeatable. Control spots can provide a consistent result independent of the labeled sample hybridized to the array (or a labeled binding molecule from a sample). The control spots can be used to generate a "normalization" or "calibration" curve to offset possible intensity errors between the two arrays (or more) used in the in silico, array-based methods of the invention.

One method of generating a control on the array would be to use an equimolar mixture of all the biological molecules (e.g., nucleic acid sequences) spotted on the array and generating a single spot. This single spot would have equal amounts of the biological molecules (e.g., nucleic acid sequences) from all the other spots on the array. Multiple control spots can be generated by varying the concentration of the equimolar mixture.

Samples and Specimens

The sample nucleic acid may be isolated, cloned, or extracted from particular cells, tissues, or other specimens. The cell or tissue sample from which the nucleic acid sample is prepared is typically taken from a patient having or suspected of having UC or a related condition. Methods of isolating cell and tissue samples are well known to those of skill in the art and include, but are not limited to, aspirations, tissue sections, needle biopsies, and the like. Frequently, the sample will be a "clinical sample" which is a sample derived from a patient, including whole blood, or sections of tissues, such as frozen sections or paraffin sections taken for histological purposes. The sample can also be derived from supernatants (of ceils) or the cells themselves taken from patients or from cell cultures, cells from tissue culture and other media in which it may be desirable to detect the response to drug candidates. In some cases, the nucleic acids may be amplified using standard techniques such as PGR, prior to the hybridization.

In one embodiment, the present invention is a post-treatment method of monitoring disease resolution. The method includes (1) taking a colon biopsy or other specimen from an individual diagnosed with UC or a related disease or disorder, (2) measuring the expression levels of the profile genes of the panel, (3) comparing the post-treatment expression level of the genes with a pre-treatment reference profile for the individual, and (4) determining the prognosis for resolution of the UC condition by monitoring at least one constituent of the UC-related gene profile.

In another embodiment, the present invention is a diagnostic method for UC and the reference standard (sample) is taken from an uninvolved site and the test sample from a suspect biopsy.

Methods of Assessing Biomarker Utility

The diagnostic and prognostic utility of the present biomarker gene panel for assessing a patient's response to treatment, prognosis, or presence, extent, severity or stage of disease can be validated by using other means for assessing a patient's state of health or disease. For example, gross measurement of disease may be assessed and recorded by certain imaging methods, such as but not limited to: physician evaluation, imaging by photographic, radiometric, or magnetic resonance technology. General indices of health or disease further include serum or blood composition (protein, liver enzymes, pH, electrolytes, red cell volume, hematocrit, hemoglobin, or specific protein). However, in some diseases, the etiology is still poorly understood. UC is an example of one such disease.

Patient Assessment and Monitoring

Some of the genes in the panel have been reported to be aberrantly expressed in UC patients previously, such as IL-1b, IL-1ra, IL-6, superoxide dismutase, selectins, integrins, and various MMPs etc., the expression patterns of the genes over the course of treatment have not been studied in the treatment of UC, and none has been identified as having predictive value. The panel of gene expression biomarkers disclosed herein permits the generation of methods for rapid and reliable prediction, diagnostic tools that predict the clinical outcome of a UC trial, or prognostic tools for tracking the efficacy of UC therapy. Diagnostic and prognostic methods based on detecting these genes in a sample are provided. These compositions may be used, for example, for the diagnosis, prevention and treatment of a range of immune-mediated inflammatory diseases.

Therapeutic Agents

Antagonists

As used herein, the term "antagonists" refer to substances which inhibit or neutralize the biologic activity of the gene product of the UC-related gene panel of the invention. Such antagonists accomplish this effect in a variety of ways. One class of antagonists will bind to the gene product protein with sufficient affinity and specificity to neutralize the biologic effects of the protein, included in this class of molecules are antibodies and antibody fragments (such as, for example, F(ab) or F(ab')$_2$ molecules). Another class of antagonists comprises fragments of the gene product protein, muteins or small organic molecules, i.e., peptidomimetics, that will bind to the cognate binding partners or ligands of the gene product, thereby inhibiting the biologic activity of the specific interaction of the gene product with its cognate ligand or receptor. The UC-related gene antagonist may be of any of these classes as long as it is a substance that inhibits at least one biological activity of the gene product.

Antagonists include antibodies directed to one or more regions of the gene product protein or fragments thereof, antibodies directed to the cognate ligand or receptor, and partial peptides of the gene product or its cognate ligand which inhibit at least one biological activity of the gene product. Another class of antagonists include siRNAs, shRNAs, antisense molecules and DNAzymes targeting the gene sequence as known in the art are disclosed herein.

Suitable antibodies include those that compete for binding to UC-related gene products with monoclonal antibodies that block UC-related gene product activation or prevent UC-related gene product binding to its cognate ligand, or prevent UC-related gene product signaling.

A therapeutic targeting the inducer of the psoriasis-related gene product may provide better chances of success. Gene expression can be modulated in several different ways including by the use of siRNAs, shRNAs, antisense molecules and DNAzymes. Synthetic siRNAs, shRNAs, and DNAzymes can be designed to specifically target one or more genes and they can easily be delivered to ceils in vitro or in vivo.

The present invention encompasses antisense nucleic acid molecules, i.e., molecules that are complementary to a sense nucleic acid encoding a UC-related gene product polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a UC-related gene product polypeptide. The non-coding regions ("5' and 3' untranslated regions") are the 5' and 3' sequences that flank the coding region and are not translated into amino acids.

The invention also provides chimeric or fusion proteins. As used herein, a "chimeric protein" or "fusion protein" comprises all or part (preferably biologically active) of a UC-related gene product polypeptide operably linked to a heterologous polypeptide (i.e., a polypeptide other than the same UC-related gene product polypeptide). Within the fusion protein, the term "operably linked" is intended to indicate that the UC-related gene product polypeptide and the heterologous polypeptide are fused in-frame to each other. The heterologous polypeptide can be fused to the amino-terminus or the carboxyl-terminus of the UC-related gene product polypeptide. In another embodiment, a UC-related gene product polypeptide or a domain or active fragment thereof can be fused with a heterologous protein sequence or fragment thereof to form a chimeric protein, where the polypeptides, domains or fragments are not fused end to end but are interposed within the heterologous protein framework.

In yet another embodiment, the fusion protein is an immunoglobulin fusion protein in which all or part of a UC-related gene product polypeptide is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a UC-related gene product polypeptide, inhibition of ligand/receptor interaction can be useful therapeutically, both for treating proliferative and differentiative disorders and for modulating (e.g., promoting or inhibiting) cell survival. A preferred embodiment of an immunoglobulin chimeric protein is a CH1 domain-deleted immunoglobulin or "mimetibody" having an active polypeptide fragment interposed within a modified framework region as taught in co-pending application PCT WO/04002417. Moreover, the immunoglobulin fusion proteins of the invention can be used as immunogens to produce antibodies directed against a UC-related gene product polypeptide in a subject, to purify ligands and in screening assays to identify molecules that inhibit the interaction of receptors with ligands.

Compositions and their Uses

In accordance with the invention, the neutralizing anti-UC-related gene product antagonists, such as monoclonal antibodies, described herein can be used to inhibit UC-related gene product activity. Additionally, such antagonists can be used to inhibit the pathogenesis of UC and -related inflammatory diseases amenable to such treatment, which may include, but are not limited to, rheumatic diseases. The individual to be treated may be any mammal and is preferably a primate, a companion animal which is a mammal and most preferably a human patient. The amount of antagonist administered will vary according to the purpose it is being used for and the method of administration.

The UC-related gene antagonists may be administered by any number of methods that result in an effect in tissue in which pathological activity is desired to be prevented or halted. Further, the anti-UC-related gene product antagonists need not be present locally to impart an effect on the UC-related gene product activity, therefore, they may be administered wherever access to body compartments or fluids containing UC-related gene product is achieved. In the case of inflamed, malignant, or otherwise compromised tissues, these methods may include direct application of a formulation containing the antagonists. Such methods include intravenous administration of a liquid composition, transdermal administration of a liquid or solid formulation, oral, topical administration, or interstitial or inter-operative administration, Adminstration may be affected by the implantation of a device whose primary function may not be as a drug delivery vehicle.

For antibodies, the preferred dosage is about 0.1 mg/kg to 100 mg/kg of body weight (generally about 10 mg/kg to 20 mg/kg), if the antibody is to act in the brain, a dosage of about 50 mg/kg to 100 mg/kg is usually appropriate. Generally, partially human antibodies and fully human antibodies have a longer half-life within the human body than other antibodies. Accordingly, the use of lower dosages and less frequent administration is often possible. Modifications, such as lipidation, can be used to stabilize antibodies and to enhance uptake and tissue penetration (e.g., into the brain). A method for lipidation of antibodies is described by Cruikshank et at ((1997) *J. Acquired Immune Deficiency Syndromes and Human Retrovirology* 14:193).

The UC-related gene product antagonist nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc, Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Pharmacogenomics

Agents, or modulators that have a stimulatory or inhibitory effect on activity or expression of a UC-related gene product polypeptide as identified by a screening assay described herein, can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a UC-related gene product polypeptide, expression of a UC-related gene product nucleic acid, or mutation content of a UC-related gene product gene in an individual can be determined to thereby select an appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism." These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D8 is highly polymorphic and several mutations have been identified in PM, which all lead to the absence of functional CYP2D6. Poor metabolizers of CYP2D8 and CYP2C19 quite frequently experience exaggerated drug response and side effects when they receive standard doses. It a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a UC-related gene product polypeptide, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Methods of Treatment

The present invention provides for both prophylactic and therapeutic methods of treating a subject at risk of (or susceptible to) a disorder or having a disorder associated with aberrant expression or activity of a UC-related gene product polypeptide and/or in which the UC-related gene product polypeptide is involved.

The present invention provides a method for modulating or treating at least one UC-related gene product related disease or condition, in a cell, tissue, organ, animal, or patient, as known in the art or as described herein, using at least one UC-related gene product antagonist.

Compositions of UC-related gene product antagonist may find therapeutic use in the treatment of UC or related conditions, such as Crohn's disease or other gastrointestinal disorders.

The present invention also provides a method for modulating or treating at least one gastrointestinal, immune related disease, in a cell, tissue, organ, animal, or patient including, but not limited to, at least one of gastric ulcer, inflammatory bowel disease, ulcerative colitis, Crohn's pathology, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn., (1998, 2000), each entirely incorporated by reference.

Disorders characterized by aberrant expression or activity of the UC-related gene product polypeptides are further described elsewhere in this disclosure.

1. Prophylactic Methods

In one aspect, the invention provides a method for at least substantially preventing in a subject, a disease or condition associated with an aberrant expression or activity of a UC-related gene product polypeptide, by administering to the subject an agent that modulates expression or at least one activity of the polypeptide. Subjects at risk for a disease that is caused or contributed to by aberrant expression or activity of a UC-related gene product can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

2. Therapeutic Methods

Another aspect of the invention pertains to methods of modulating expression or activity of UC-related gene or gene product for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptsdomimetic, or other small molecule. In one embodiment, the agent stimulates one or more of the biological activities of the polypeptide. In another embodiment, the agent inhibits one or more of the biological activities of the UC-related gene or gene product polypeptide. Examples of such inhibitory agents include antisense nucleic acid molecules and antibodies and other methods described herein. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a UC-related gene product polypeptide. In one embodiment, the method involves administering an agent (e.g., an agent identified by a screening assay described herein), or combination of agents that modulate (e.g., up-regulates or down-regulates) expression or activity. Inhibition of activity is desirable in situations in which activity or expression is abnormally high or up-regulated and/or in which decreased activity is likely to have a beneficial effect.

While having described the invention in general terms, the embodiments of the invention will be further disclosed in the following examples which should not be construed as limiting the scope of the claims.

Example 1

Sample Analysis by Using Nucleic Acid Microarrays

Colon Biopsies from Infliximab Treated Ulcerative Colitis Patients

Sample Collection and RNA Isolation

Patients with moderate to severe active UC were randomly assigned 1:1:1 to intravenous placebo or infliximab (anti-TNF antibody) at a dose of 5 or 10 mg/kg at 0, 2, 6 and every 8 weeks thereafter. Colonoscopic punch biopsies were obtained from disease tissues at weeks 0 (prior to therapy), 8, and 30 and kept frozen until RNA preparation. RNA isolated from the biopsy samples was subsequently used for Affymetrix (oligonucleotide) microarray analysis. One hundred and twenty-three colon biopsy samples were collected from 49 subjects in this study. Gene expression profiles from 36 infliximab treatment responder samples in both 5 and 10 mg/kg treatment group at both weeks 8 and 30 were compared to that of 13 non-responder samples across both dose groups at both time points as described herein. Treatment responders showed a marked clinical improvement following therapy defined by a decrease from baseline Mayo score by at least 3 points and at least 30% with an accompanying decrease in rectal bleeding sub-score of at least 1 point or an absolute rectal bleeding sub-score of 0 or 1.

Total RNA was isolated with an RNeasy mini kit according to the manufacturer's instructions (Qiagen inc., Valencia, Calif.). The colon biopsy samples were lysed and homogenized in the presence of 600 μL of GITC (guanidine isothiocyanate)-containing buffer, which immediately inactivates RNase to ensure isolation of intact RNA. 600 μL of 70% ethanol was added to provide appropriate binding conditions and the sample was then applied to an RNeasy mini spin column where the total RNA binds to the membrane and contaminants were efficiently washed away. High-qualify RNA was then eluted in 30 μL of water. RNA quality and quantity was analyzed with 2100 Bioanalyzer (Agilent Technologies Inc., Palo Alto, Calif.).

Microarray Data Analysis

Microarray analysis was performed on GeneChip Human Genome U133 Plus 2.0 arrays that allow the analysis of the expression level of more than 47,000 transcripts and variants, including 38,500 well-characterized human genes. RNA amplification, target synthesis and labeling, chip hybridization, washing and staining were performed in accordance with the manufacturer's protocol (Affymetrix, Santa Ciara, Calif.), The GeneChips were scanned using the GeneChip Scanner 3000. The data were analyzed with GCOS 1.4 (GeneChip Operating System) using Affymetrix default analysis settings and global scaling as normalization method. The trimmed mean target intensity of each array was arbitrarily set to 500.

Data quality was assessed by hybridization intensity distribution and Pearson's correlation in Partek Pro software version 8.1 (Partek Inc., St. Charles, Mo.), and was deemed good except for two samples, E36507_P43_5 mg/kg_W30 & E36498_P39_placebo_W8. These samples were regarded as outliers and removed from data analysis.

Using GeneSpring™ software version 7.2 (Agilent Technologies, Palo Alto, Calif.), the intensity for probe set was normalized across all samples. Each measurement was divided by the median of all measurements in that sample. The intensity of a probe set was then normalized to the median intensity of that probe set in the control group. The control groups in this study were all 45 week 0 samples. Normalized intensity of probe set A in sample X was calculated as follows:

$$\frac{\text{(Signal intensity of probe set } A \text{ in sample } X)}{\text{(Median intensity of all measurements in sample } X) \times} $$
$$\text{(Median intensity of probe set } A \text{ across all week-0 samples)}$$

Using Partek Pro 6.1, statistical analysis was done to identify significant treatment effects, and the differences between respondent and non-responders, using log 2 transformed normalized intensities. Standard ANOVA was conducted between responders at each treatment condition (5 mg/kg week 8, 5 mg/kg week 30, 10 mg/kg week 8, and 10 mg/kg week 30) vs. the corresponding baseline, and between responders and non-responders under each treatment condition. Subject effect was tested in the mix-model of ANOVA as a random factor. Differences were considered statistically significant at p-value<0.05. Using linear scaled data, genes showing more than 2× significant differential expression for a specific comparison were identified. Only the genes designated Present or Marginally Present at least once among the samples representing the condition with a higher expression level in a comparison were documented.

Class Prediction Analysis. Classification of infliximab responsiveness for each patient sample is generated with the 'K-Nearest Neighbors' algorithm (Cover TM HP, Nearest neighbor pattern classification. IEEE Transactions on information Theory 1987; 13:21-27). Week-8 or week-30 samples comprise the training set and week-8 or week-30 samples the test set. Fisher's Exact Test is used to select a smaller set of transcripts from the training set yielding the treatment-response-specific class prediction at week 8 or 30. Transcripts are scored based on the best prediction for a class. The predictive strength is the negative natural logarithm of the p-value for a hypergeometric test of predicted versus actual class membership for this class versus others. The class prediction analysis can lead to a gene panel.

Gene expression signatures between responder and nonresponder samples are compared at week 8 or 30, Classification is generated by the 'K-Nearest Neighbors' algorithm using 27 week-8 or week-30 samples as the training set (20 responders and 7 nonresponders) to predict infliximab responsiveness of the 22 week-8 or week-30 samples in the test set (16 responders and 8 nonresponders). A common set of transcripts is identified that pass ANOVA and 2-fold change cut-off in both the 5- and 10-mg/kg dose groups between responders and nonresponders at week 8 or 30. Upon subsequent Fisher's Exact Test, the top predictive transcripts (e.g., the top 50) are selected to achieve an acceptable predictive accuracy with a minimal number of transcripts.

Differences in gene expression profiles between weeks 8 and 30 were also noted when infliximab 5 and 10 mg/kg treatment responder vs. nonresponder samples were compared. Distinct transcripts were associated with the maintenance therapy up to week 30 that were different from those affected by the induction regimen up to week 8. Among the transcripts unique to week 30, immune response genes, such as IL-17A, were down regulated. IL-17A has been shown to play a key role in autoimmune diseases and animal models of inflammatory diseases, and increased expression has been associated with UC and CD. Also, chemokines that can be induced by IL-17A, e.g., CXCL2, 6, and 8 (IL-8), and chemokines important for neutrophil migration, innate immunity, acute inflammation, and T cell migration/adaptive immunity, including CXCL3, 5, 9, 10, and 11, respectively, were all downregulated in responder samples. Downregulation of matrix remodeling genes, such as matrix metalloproteinases (MMPs) 7, 9, 10, 12, and 19, and tissue inhibitor of metalloproteinase (TIMP1) was also observed.

To explore differential gene expression profiles for infliximab non-responders in UC at various follow-up time points, gene expression changes were examined in the infliximab nonresponder samples for both dose groups (n=8) at week 30 relative to baseline samples (n=13). The differential expression profiles were then compared with those in the infliximab responder samples (n=10 in the 10 mg/kg group) at week 30 relative to baseline samples (n=17). Among the genes showing unique expression changes in the nonresponder expression profiles, SL-23p19, CCR1, and serum amyloid protein A (SAA) were significantly upregulated by 2.3-, 2.0-, and 2.3- fold, respectively, Conversely, these genes were consistently and significantly downregulated by infliximab in responder samples. Additionally, a parathyroid hormone-like hormone (PTHLH), G-protein coupled receptor 86 (GPR86), and a Ral-GDS-related protein (Rgr) were also significantly upregulated in the nonresponder samples. Expression of other genes that were significantly downregulated by infliximab treatment in the responder samples was not changed significantly in nonresponder samples at weeks 8 and 30 relative to baseline. The combination of the significant and nonsignificant gene expression changes in nonresponder vs. responder samples suggests a unique molecular signature for the infliximab treatment nonresponders.

Microarray Results

Biopsies taken from infliximab treatment responders and non-responders at weeks 8 and 30 allowed an understanding of the potential mechanism underlying treatment response and non-response in UC. The post-treatment responder samples analyzed were taken from patients who showed a marked clinical improvement following infliximab therapy as defined above. The non-responder samples were taken from patients who did not achieve the treatment response as defined above.

Gene expression results from responders in each treatment condition (11, 6, 9, and 10 responders from 5 mg/kg dose group at weeks 8 and 30, 10 mg/kg dose group at weeks 8 and 30, respectively) were compared to that of non-responders in the corresponding dose groups at weeks 8 and 30 (2, 3, 5, and 3 non-responders from 5 mg/kg dose group at weeks 8 and 30, 10 mg/kg group at weeks 8 and 30, respectively). The number of genes that demonstrated significant changes with equal or greater than 2-fold differential expression between an infliximab responder vs. non-responder across both dose groups and time points is listed in Table 1.

A common set of 66 genes (results with different probe sets against the same gene were averaged) with significant differential expression at either week 8 or 30 in infliximab treatment responder samples vs. non-responder samples across 5 mg/kg and 10 mg/kg dose groups is listed in Table 1. Each differentially expressed gene is presented by the ratio of normalized hybridization intensity of infliximab treatment responder samples to that of non-responder samples (Ratio 1 represents 6 mg/kg responder sample vs. non-responder sample comparison at week 8; Ratio 2 represents 10 mg/kg responder sample vs. non-responder sample comparison at week 8; Ratio 3 represents 5 mg/kg responder sample vs. non-responder sample comparison at week 30; Ratio 4 represents 10 mg/kg responder sample vs. non-responder sample comparison at week 30). Since these genes passed the ANOVA test with a p-value of less than 0.05 and the 2-fold cut-off in the infliximab treatment responder samples when compared to infliximab treatment non-responder samples at all four conditions across two different dose groups and two different post-treatment time points, the entire expression profile as detailed in Table 1 is therefore defined as the infliximab treatment response signature in UC. In this response gene signature, 64 genes were expressed at lower levels in infliximab treatment responder samples as compared with that in the non-responder samples with at least 2-fold change in the expression levels of each gene. Only two genes were expressed at higher levels in infliximab treatment responder samples as compared with those in non-responder samples with at least 2-fold change.

Genes that were expressed at lower levels in the infliximab treatment responders in the response signature can be grouped info 7 main categories based on their functions. The first category consists of genes reported to be involved in immune and inflammatory responses as represented by IL-1β, IL-1ra, IL-6, IL-8Rβ, IL-11, IL-13Rα2, IL-23A, IL-24, oncostatin M (OSM), TNFα-inducible protein 6 (TNFAIP6), superoxide dismutase 2, selectin E: selectin L, T-cell activation GTPase (TAGAP), TLR2, and TREM1. The second class consists of genes reported to be involved in cell growth, proliferation, maintenance, apoptosis, cell-cell signaling, and cell adhesion, such as TNFR superfamily member 10c (TNFRSF10c), BCL2A1, BCL6, integrin alpha X (ITGAX), and protocadherin 17. The third class consists of genes reported to be involved in signal transduction, such as WNT5A and prokineticin 2. The fourth class consists of genes reported to be involved in matrix turnover, such as MMP3 and MMP25. The fifth class consists of genes that have been reported to be important for various metabolisms and the transporter genes. The sixth class is composed of genes reported to be involved in cytoskeleton organizations, such as myosin 1F and Kelch-like 5 gene, and the last class consists of genes reported to be involved in hormonal regulations, such as PTH (parathyroid hormone) like hormone, in the response signature, the two genes that were expressed at higher levels in the infliximab treatment responder samples were thyroid hormone receptor beta (THRB) and carboxypeptidase A6 (CPA6).

The genes disclosed above, not identified in SEQ ID NOS: 1-66, and those identified in SEQ ID NOS: 1-66, individually or in combination, are useful as biomarkers to assess the presence or severity of UC-related diseases or disorders, the response to treatment with a particular therapy (e.g., an anti-TNF antibody, such as infliximab), such as a treatment responder or non-responder, and as therapeutic targets for UC-related diseases or disorders.

Utility of the Response Signature

The response signature for infliximab treatment in UC described herein can be assessed and used as described below.

1) Archived RNA samples from treatment non-responder samples (5-10) as early as 8 weeks post-treatment are used for subsequent comparison analysis.

2) Colonoscopic biopsy samples are obtained from lesional sites of patients with active UC as early as 8 weeks post-treatment. RNA will then be isolated from the biopsy samples and subjected to real time RT-PCR analysis. One microgram of total RNA in the volume of 50 μl was converted to cDNA in the presence of Multi-Scribe Reverse Transcriptase. The reaction was carried out by incubating for 10 minutes at 25° C. followed by 30 minutes at 48° C. Reverse Transcriptase was inactivated at 95° C. for 5 minutes. Twenty-five nanograms of cDNA per reaction was used in real time PCR with ABI 7900 system (Foster City, Calif.), in the presence of AmpliTaq Gold DNA polymerase (ABI biosystem, Foster City, Calif.), the reaction was incubated for 2 minutes at 50° C. followed by 10 minutes at 95° C. Then the reaction was run for 40 cycles at 15 seconds, at 95° C. and 1 minute, 60° C. per cycle using primer/probe sets specific for the genes in the response signature. House keeping genes, such as GAPDH or actin, will be used as infernal calibrators. The relative change in gene expression is calculated using the delta-delta Ct method described by Applied Biosystems using values in the non-responder samples as the calibrator or comparator.

3) if a similar gene expression profile meets the parameters of the gene profile signature, i.e., 66 of the same signature genes showed lower expression with at least 2 fold change in the responder samples as compared with that in the non-responder samples and two genes (THRB and CPAS) showed elevated expression with at least 2 fold change in the responder vs. non-responder samples, then the patient is defined as a treatment responder. In which case, the patient will be kept on therapy, 4) if the gene expression profile does not meet the parameters of the gene profile signature, based on the direction of the change in expression level or magnitude of the changes, then the patient is defined as a treatment non-responder, in which case, the patient should discontinue the therapy. This enables a patient to avoid therapy earlier after being deemed a non-responder. This can allow the patient to receive a different type of therapy.

TABLE 1

A common set of 66 genes with significant differential expression in the infliximab treatment responder samples vs. non-responder samples at weeks 8 and 30 across 5 mg/kg and 10 mg/kg dose groups.

| Gene Bank# | Name (SEQ ID NO) | Ratio 1 | Ratio 2 | Ratio 3 | Ratio 4 | Description | Functional categories |
|---|---|---|---|---|---|---|---|
| NM_000576 | IL1B (1) | 6.54 | 5.43 | 9.62 | 8.06 | interleukin 1, beta | immune/inflammatory response |
| BE563442 | IL1RN (2) | 3.89 | 2.32 | 7.87 | 3.97 | interleukin 1 receptor antagonist | immune/inflammatory response |
| NM_000600 | IL6 (3) | 4.18 | 3.61 | 13.59 | 4.83 | interleukin 6 (interferon, beta 2) | immune/inflammatory response |
| NM_001557 | IL8RB (4) | 8.93 | 5.65 | 22.78 | 19.92 | interleukin 8 receptor, beta | immune/inflammatory response |
| NM_000641 | IL11 (5) | 4.61 | 16.61 | 26.04 | 12.50 | interleukin 11 | immune response |
| NM_000640 | IL13RA2 (6) | 12.99 | 6.41 | 28.41 | 8.13 | interleukin 13 receptor, alpha 2 | immune/inflammatory response |
| NM_016584 | IL23A (7) | 3.98 | 2.49 | 8.55 | 4.95 | interleukin 23, alpha subunit p19 | immune response |
| NM_006850 | IL24 (8) | 3.37 | 3.05 | 7.46 | 10.05 | interleukin 24 | immune response |
| AI079327 | OSM (9) | 8.70 | 10.00 | 42.55 | 23.64 | oncostatin M | immune/inflammatory response |
| AW188198 | TNFAIP6 (10) | 7.04 | 2.71 | 12.38 | 7.94 | tumor necrosis factor, alpha-induced protein 6 | immune/inflammatory response |
| BF433902 | TNFRSF11B (11) | 4.10 | 3.48 | 4.20 | 3.13 | tumor necrosis factor receptor superfamily, member 11b (osteoprotegerin) | inflammatory response |
| NM_000760 | CSF3R (12) | 5.29 | 4.90 | 24.39 | 15.48 | colony stimulating factor 3 receptor (granulocyte) | defense response |
| AV756141 | CSF2RB (13) | 3.86 | 2.54 | 4.67 | 5.59 | colony stimulating factor 2 receptor, beta, low-affinity (granulocyte-macrophage) | defense response |
| L03419 | FCGR1A (14) | 4.31 | 2.39 | 6.17 | 6.80 | Fc fragment of IgG, high affinity Ia, receptor for (CD64) | immune/inflammatory response |
| NM_021642 | FCGR2A (15) | 4.81 | 2.85 | 6.49 | 6.94 | Fc fragment of IgG, low affinity IIa, receptor for (CD32) | immune response |
| J04162 | FCGR3A (16) | 7.14 | 4.17 | 21.65 | 13.64 | Fc fragment of IgG, low affinity IIIa, receptor for (CD16) | immune/inflammatory response |

TABLE 1-continued

A common set of 66 genes with significant differential expression in the infliximab treatment responder samples vs. non-responder samples at weeks 8 and 30 across 5 mg/kg and 10 mg/kg dose groups.

| Gene Bank# | Name (SEQ ID NO) | Ratio 1 | Ratio 2 | Ratio 3 | Ratio 4 | Description | Functional categories |
|---|---|---|---|---|---|---|---|
| U82276 | LILRA2 (17) | 4.61 | 4.59 | 6.99 | 8.70 | leukocyte immunoglobulin-like receptor, subfamily B (with TM and ITIM domains), member 1 | immune response |
| AF004231 | LILRB2 (18) | 3.42 | 2.25 | 8.93 | 5.46 | leukocyte immunoglobulin-like receptor, subfamily B (with TM and ITIM domains), member 2 | immune response |
| AF009635 | LILRB3 (19) | 3.64 | 2.21 | 4.72 | 3.88 | leukocyte immunoglobulin-like receptor, subfamily B (with TM and ITIM domains), member 3 | immune response |
| BC001606 | NCF2 (20) | 6.90 | 2.52 | 8.33 | 8.26 | neutrophil cytosolic factor 2 (65 kDa, chronic granulomatous disease, autosomal 2) | defense response |
| NM_000963 | PTGS2 (21) | 4.90 | 5.92 | 11.55 | 8.55 | prostaglandin-endoperoxide synthase 2 (prostaglandin G/H synthase and cyclooxygenase) | inflammatory response |
| BF591040 | TAGAP (22) | 5.78 | 3.60 | 7.75 | 6.13 | T-cell activation GTPase activating protein | immune response |
| NM_003264 | TLR2 (23) | 4.08 | 2.39 | 4.95 | 5.88 | toll-like receptor 2 | immune/inflammatory response |
| NM_018643 | TREM1 (24) | 17.67 | 6.80 | 35.34 | 71.43 | triggering receptor expressed on myeloid cells 1 | innate immune response |
| W46388 | SOD2 (25) | 5.18 | 3.08 | 7.52 | 4.93 | superoxide dismutase 2, mitochondrial | defense response |
| NM_000450 | SELE (26) | 4.44 | 6.76 | 19.88 | 15.77 | selectin E (endothelial adhesion molecule 1) | inflammatory response |
| NM_000655 | SELL (27) | 4.17 | 2.46 | 4.95 | 4.85 | selectin L (lymphocyte adhesion molecule 1) | cell adhesion |
| AF010316 | PTGES (28) | 3.23 | 2.10 | 2.25 | 2.58 | prostaglandin E synthase | signal transduction |
| NM_002432 | MNDA (29) | 5.81 | 4.44 | 13.35 | 10.73 | myeloid cell nuclear differentiation antigen | defense response |
| AF400600 | CLECSF12 (30) | 4.98 | 3.36 | 5.65 | 7.14 | C-type (calcium dependent, carbohydrate-recognition domain) lectin, superfamily member 12 | defense response |
| NM_003841 | TNFRSF10C (31) | 3.36 | 2.82 | 7.14 | 4.17 | tumor necrosis factor receptor superfamily, member 10c, decoy without an intracellular domain | apoptosis |

TABLE 1-continued

A common set of 66 genes with significant differential expression in the infliximab treatment responder samples vs. non-responder samples at weeks 8 and 30 across 5 mg/kg and 10 mg/kg dose groups.

| Gene Bank# | Name (SEQ ID NO) | Ratio 1 | Ratio 2 | Ratio 3 | Ratio 4 | Description | Functional categories |
|---|---|---|---|---|---|---|---|
| NM_004049 | BCL2A1 (32) | 7.35 | 3.83 | 13.51 | 14.39 | BCL2-related protein A1 | apoptosis regulation |
| AW264036 | BCL6 (33) | 3.91 | 3.05 | 7.63 | 4.12 | B-cell CLL/lymphoma 6 (zinc finger protein 51) | regulation of cell growth |
| M81695 | ITGAX (34) | 4.42 | 2.43 | 3.65 | 3.40 | integrin, alpha X (antigen CD11C (p150), alpha polypeptide) | cell-matrix adhesion |
| M13436 | INHBA (35) | 10.36 | 8.06 | 26.67 | 12.85 | inhibin, beta A (activin A, activin AB alpha polypeptide) | cell growth and/or maintenance |
| NM_015714 | G0S2 (36) | 6.37 | 5.21 | 11.43 | 12.12 | putative lymphocyte G0/G1 switch gene | regulation of cell cycle |
| N69091 | PLA2G2D (37) | 2.59 | 2.51 | 2.44 | 4.12 | protocadherin 17 | cell adhesion |
| AF182069 | PROK2 (38) | 10.32 | 11.38 | 70.92 | 86.96 | prokineticin 2 | inflammatory response |
| NM_003392 | WNT5A (39) | 2.99 | 2.33 | 3.66 | 3.27 | wingless-type MMTV integration site family, member 5A | signal transduction |
| BC020691 | PBEF1 (40) | 4.98 | 3.24 | 6.37 | 9.62 | pre-B-cell colony enhancing factor 1 | cell-cell signaling |
| NM_013447 | EMR2 (41) | 3.27 | 2.78 | 6.17 | 7.30 | egf-like module containing, mucin-like, hormone receptor-like 2 | signaling pathway |
| NM_006018 | GPR109B (42) | 17.86 | 13.26 | 62.50 | 73.53 | putative chemokine receptor | G-protein signaling |
| NM_002029 | FPR1 (43) | 7.87 | 4.42 | 20.12 | 19.80 | Formyl peptide receptor 1 | G-protein signaling |
| NM_005306 | GPR43 (44) | 8.85 | 4.83 | 30.40 | 9.80 | G protein-coupled receptor 43 | G-protein signaling |
| NM_170776 | GPR97 (45) | 3.97 | 2.16 | 6.06 | 5.81 | G protein-coupled receptor 97 | G-protein signaling |
| L20966 | PDE4B (46) | 4.37 | 2.99 | 7.11 | 6.25 | phosphodiesterase 4B, cAMP-specific (phosphodiesterase E4 dunce homolog, *Drosophila*) | signal transduction |
| NM_002664 | PLEK (47) | 7.41 | 3.28 | 11.61 | 6.29 | pleckstrin | intracellular signaling cascade |
| NM_006317 | BASP1 (48) | 3.47 | 2.16 | 3.29 | 4.15 | brain abundant, membrane attached signal protein 1 | signaling pathway |
| NM_002422 | MMP3 (49) | 5.41 | 3.37 | 11.67 | 9.43 | Matrix metalloproteinase 3 (stromelysin 1, progelatinase) | collagen catabolism |
| NM_022718 | MMP25 (50) | 3.53 | 2.46 | 5.56 | 4.20 | Matrix metalloproteinase 25 | proteolysis |
| BC022313 | PRG1 (51) | 4.46 | 4.17 | 9.52 | 5.71 | proteoglycan 1, secretory granule | matrix |
| BG251467 | MSCP (52) | 2.57 | 2.21 | 5.81 | 3.21 | mitochondrial solute carrier protein | transporter |
| U73191 | KCNJ15 (53) | 11.24 | 4.39 | 17.67 | 24.45 | potassium inwardly-rectifying channel, subfamily J, member 15 | ion transport |

TABLE 1-continued

A common set of 66 genes with significant differential expression in the infliximab treatment responder
samples vs. non-responder samples at weeks 8 and 30 across 5 mg/kg and 10 mg/kg dose groups.

| Gene Bank# | Name (SEQ ID NO) | Ratio 1 | Ratio 2 | Ratio 3 | Ratio 4 | Description | Functional categories |
|---|---|---|---|---|---|---|---|
| AI631159 | SLC2A3 (54) | 4.27 | 2.40 | 6.33 | 7.04 | solute carrier family 2 (facilitated glucose transporter), member 3 | glucose transporter |
| AA778684 | SLC2A14 (55) | 3.40 | 2.35 | 4.95 | 4.55 | solute carrier family 2 (facilitated glucose transporter), member 14 | glucose transporter |
| AA650281 | FLJ23153 (56) | 3.80 | 2.67 | 4.69 | 6.29 | likely ortholog of mouse tumor necrosis-alpha-induced adipose-related protein | regulation of adiposity |
| NM_001995 | ACSL1 (57) | 4.35 | 2.55 | 6.33 | 6.10 | acyl-CoA synthetase long-chain family member 1 | fatty acid metabolism |
| NM_022977 | ACSL4 (58) | 2.74 | 2.03 | 3.61 | 2.78 | acyl-CoA synthetase long-chain family member 4 | fatty acid metabolism |
| NM_000167 | GK (59) | 2.29 | 2.22 | 2.18 | 2.74 | glycerol kinase | carbohydrate metabolism |
| X14174 | ALPL (60) | 2.65 | 2.49 | 4.05 | 6.10 | alkaline phosphatase, liver/bone/kidney | metabolism |
| NM_018371 | ChGn (61) | 2.61 | 2.07 | 2.66 | 4.42 | chondroitin beta 1,4 N-acetylgalactosaminyl-transferase | chondroitin sulfate biosynthesis |
| AK002174 | KLHL5 (62) | 2.47 | 2.28 | 2.26 | 3.08 | kelch-like 5 (*Drosophila*) | cytoskeleton organization and biogenesis |
| BF740152 | MYO1F (63) | 2.33 | 2.02 | 3.66 | 2.93 | myosin IF | cytoskeleton organization |
| BC005961 | PTHLH (64) | 8.70 | 3.16 | 4.55 | 7.09 | parathyroid hormone-like hormone | Hormone regulation |
| BG494007 | THRB (65) | 0.99 | 0.74 | 0.27 | 0.40 | thyroid hormone receptor, beta | hormone regulation |
| NM_020361 | CPA6 (66) | 2.03 | 0.69 | 0.42 | 0.14 | carboxypeptidase A6 | proteolysis and peptidolysis |

Each gene is presented by the ratio of normalized hybridization intensity of infliximab treatment responder samples to that of non-responder samples (Ratio 1, 5 mg/kg at week 8; Ratio 2, 10 mg/kg at week 8; Ratio 3, 5 mg/kg at week 30; Ratio 4, 10 mg/kg at week 30).

These results are novel findings in that clinical response outcome to infliximab treatment in moderate to severe UC can also be detected at the gene expression levels of a panel of selective genes. Furthermore, the panel of genes encompasses a multitude of pathogenic pathways underlying UC that are impacted by infliximab treatment. These include both innate and adaptive immune response genes, such as CSF receptors, NCF2, TLR2, TREM1 and IL-23A, IL-8Rβ, IL-11, IL-13Rα2, and IL-24. Various pro-inflammatory cytokines, such as IL-1β, IL-6, a number of TNFα-inducible genes and TNFRSF members were all significantly down regulated in infliximab responders when compared with non-responder samples. In addition, genes important for regulation of cell growth, proliferation, death and cell-cell signaling and those that affect matrix remodeling also showed differential expression in responder samples vs. non-responders samples. Therefore, a constellation of the expression changes in a panel of genes as represented in Table 1 can constitute a profile that can serve as a biomarker profile indicative of the response of a subject to treatment.

Real Time PCR (TaqMan) Confirmation:

In order to confirm the microarray finding by an independent means, Real Time PCR technology was employed. One microgram of total RNA in the volume of 50 yd was converted to cDNA in the presence of MultiScribe Reverse Transcriptase. The reaction was carried out by incubating for 10 minutes at 25° C. followed by 30 minutes at 48° C. Reverse Transcriptase was inactivated at 95° C. for 5 minutes. Twenty-five nanograms of cDNA per reaction was used in real time PCR with ABI 7900 system (Foster City, Calif.). In the presence of AmpliTaq Gold DNA polymerase (ABI biosystem, Foster City, Calif.), the reaction was incubated for 2 minutes at 50° C. followed by 10 minutes at 95° C. Then the reaction was run for 40 cycles at 15 seconds, at 95° C. and 1 minute, 60° C. per cycle. The housekeeping gene GAPDH (glyceraldehydes-3-phosphate dehydrogenase) was used to normalize gene expression. The Taqman results on a selected number of genes are consistent with the observation from the microarray analysis.

The present invention discloses the discovery of a panel of potential molecular biomarkers that is indicative of favorable outcome for the treatment of UC, The panel of identified genes represents a UC-related gene panel, which can be used as a tool to monitor the efficacy of any UC therapeutic, such as infliximab, and provide valuable information that guides dosing regimens.

A panel of genes identified as UC-related genes herein have demonstrated relevance to UC, IBD, and inflammation. As demonstrated by the present analysis, the panel as a whole provides a fingerprint for gauging the efficacy of a treatment of UC that leads to an improvement in the involvement and severity of disease lesions.

In summary, a panel of potential molecular biomarkers that is indicative of favorable outcome for the treatment of UC has been identified along with the direction in which they are modulated. This panel of biomarkers is particularly useful in guiding clinical development, as the change in expression of genes in this panel can appear prior to improvement of clinically measurable parameters, such as improvement in microscopic changes of the lesions, can be achieved and/or detected. Thus, the 88 identified genes represent a UC-related gene panel which can be used as a tool to monitor the efficacy of any UC therapeutic, such as anti-TNF antibody, and provide valuable information that guides dosing regimens.

A panel of genes identified as UC-related genes herein have demonstrated relevance to UC and Crohn's disease. As demonstrated by the present analysis, the panel as a whole provides a fingerprint for gauging the efficacy of a treatment of UC that leads to an improvement in the involvement and severity of UC in patients. A number of the genes, which are members of the UC-related gene panel, have been previously shown to be aberrantly expressed in UC patient samples. For example, increased levels of IL-1b, IL-tra, IL-8, superoxide dismutase, selectins, integrins, and various MMPs have been associated with UC. Thus, together, monitoring genes in this panel provides a method for evaluating drug candidates and in so far as the modulation of the expression of these genes predicts the clinical outcome of a UC therapy.

Although illustrated and described above with reference to certain specific embodiments, the present invention is nevertheless not intended to be limited to the details shown. Rather, the present invention is directed to the UC-related genes and gene products. Polynucleotides, antibodies, apparatus, and kits disclosed herein and uses thereof, and methods for controlling the levels of the UC-related biomarker genes, and various modifications may be made in the details within the scope and range of equivalents of the claims and without departing from the spirit of the invention.

REFERENCES

1. Okahara, S., Arimura, Y., Yabana, T., Kobayashi, K., Gotoh, A., Motoya, S., Smamura, A., Endo, T., and Imai, K. 2005. Inflammatory gene signature in ulcerative colitis with cDNA macroarray analysis. *Aliment Pharmacol Ther* 21:1091-1097.
2. Hanauer, S. B., Feagan, B. G., Lichtenstein, G. R., Mayer, L. F., Schreiber, S., Colombel, J. F., Rachmilewitz, D., Wolf, D. C., Olson, A., Bao, W., et al. 2002. Maintenance infliximab for Crohn's disease, the ACCENT I randomised trial. *Lancet* 359:1541-1549.
3. Rutgeerts, P., Feagan, B. G., Lichtenstein, G. R., Mayer, L. F., Schreiber, S., Colombel, J. F., Rachmilewitz, D., Wolf, D. C., Olson, A., Bao, W., et al. 2004. Comparison of scheduled and episodic treatment strategies of infliximab in Crohn's disease. *Gastroenterology* 126:402-413.
4. Sands, B. E., Anderson, F. H., Bernstein, C. N., Chey, W. Y., Feagan, B. G., Fedorak, R. N., Kamm, M A, Korzenik. J. R., Lashner, B. A., Onken, J. E., et al. 2004. Infliximab maintenance therapy for fistulizing Crohn's disease. *N Engl J Med* 350:876-885.
5. Sands, B. E., Blank, M. A., Patel, K., and van Deventer, S. J. 2004. Long-term treatment of rectovaginal fistulas in Crohn's disease: response to infliximab in the ACCENT II Study. *Clin Gastroenterol Hepatol* 2:912-920.
6. Mizoguchi, E., Mizoguchi, A., Takedatsu. H., Cario, E., de Jong, Y. P., Ooi, C. J., Xavier, R. J., Terhorst, C, Podolsky, D. K., and Bhan, A. K. 2002, Role of tumor necrosis factor receptor 2 (TNFR2) in colonic epithelial hyperplasia and chronic intestinal inflammation in mice. *Gastroenterology* 122:134-144.
7. Melgar, S., Yeung, M. M., Bas, A., Forsberg, G., Suhr, O., Oberg, A., Hammarstrom, S., Danielsson, A., and Hammarstrom, M. L. 2003, Over-expression of interleukin 10 in mucosal T cells of patients with active ulcerative colitis. *Clin. Exp Immunol* 134:127-137.
8. Leeb, S. N., Vogl, D., Gunckel, M., Kiessling, S., Falk, W., Goke, M., Scholmerich, J., Gelbmann, C. M., and Rogler, G. 2003. Reduced migration of fibroblasts in inflammatory bowel disease: role of inflammatory mediators and focal adhesion kinase. *Gastroenterology* 125:1341-1354.
9. Ten Hove, T., The Olle, F., Berkhout, M., Bruggeman, J. P., Vyth-Dreese, F. A., Slors, J. F., Van Deventer, S. J., and Te Velde, A. A. 2004. Expression of CD45RB functionally distinguishes intestinal T lymphocytes in inflammatory bowel disease. *J Leukoc Biol* 75:1010-1015.
10. Amasheh, S., Barmeyer, C., Koch, C. S., Tavalali, S., Mankertz, J., Epple, H. J., Gehring, M. M., Florian, P., Kroesen, A. J., Zeitz, M., et al. 2004. Cytokine-dependent transcriptional down-regulation of epithelial sodium channel in ulcerative colitis. *Gastroenterology* 128:1711-1720.
11. Murch, S. H., Lamkin, V. A., Savage, M. O., Walker-Smith, J. A., and MacDonald, T. T. 1991, Serum concentrations of tumour necrosis factor alpha in childhood chronic inflammatory bowel disease. *Gut* 32:913-917.
12. Murch, S. H., Braegger, C. P., Walker-Smith, J. A., and MacDonald, T. T. 1993. Location of tumour necrosis factor alpha by immunohistochemistry in chronic inflammatory bowel disease. *Gut* 34:1705-1709.
13. Braegger, C. P., Nicholls. S., Murch. S. H., Stephens, S., and MacDonald, T. T. 1992. Tumour necrosis factor alpha in stool as a marker of intestinal inflammation. *Lancet* 339:89-91.
14. Rutgeerts, P., Sandborn, W. J., Feagan, B. G., Reinisch, W., Olson, A., Johanns, J., Travers, S., Rachmilewitz, D., Hanauer, S. B., Lichtenstein, G. R., et al. 2005. Infliximab for induction and maintenance therapy for ulcerative colitis. *N Engl J Med* 353:2462-2476.
15. Pender, S. L., and MacDonald, T. T. 2004. Matrix metalloproteinases and the gut—new roles for old enzymes, *Curr Opin Pharmacol* 4:546-550.

What is claimed:

1. A method for determining the likelihood that a human subject with ulcerative colitis will respond to an anti-TNFα therapy, comprising:
   a) preparing a sample of mRNA from a specimen obtained from a colon biopsy of a human subject with ulcerative colitis treated with the anti-TNFα therapy;
   b) contacting the sample with a panel of nucleic acid probes that hybridize to the nucleic acid sequences of SEQ ID NOS: 8, 9, 28, 37, and 66;
   c) hybridizing the sample with the panel of nucleic probes to detect levels of the mRNAs in the sample encoded by the nucleic acid sequences of SEQ ID NOS: 8, 9, 28, 37, and 66;
   d) comparing the levels of the mRNAs in the sample encoded by the nucleic acid sequences of SEQ ID NOS: 8, 9, 28, 37, and 66 against a reference standard of mRNAs encoded by nucleic acid sequences of SEQ ID NOS: 8, 9, 28, 37, and 66; and
   e) determining the likelihood that the human subject will respond to the anti-TNFα therapy based on the comparison in step d).

2. The method of claim 1, wherein the anti-TNFα therapy is an anti-TNFα antibody.

3. The method of claim 2, wherein the anti-TNFα antibody is infliximab.

4. The method of claim 1, wherein the determining step comprises performing a statistical comparison of the levels of the mRNAs in the sample from the subject to a reference standard to determine the likelihood that the subject will respond to the anti-TNFα therapy.

5. The method of claim 1, wherein the levels of the mRNAs in the sample are determined using RT-PCR.

6. The method of claim 1, wherein the specimen is obtained from the subject about 8 weeks after commencement of treatment with the anti-TNFα therapy.

7. The method of claim 6, wherein the anti-TNFα therapy is infliximab.

8. The method of claim 1, wherein the specimen is obtained from the subject about 30 weeks after commencement of treatment with the anti-TNFα therapy.

9. The method of claim 8, wherein the anti-TNFα therapy is infliximab.

10. The method of claim 1, wherein the determining step further comprises determining the likelihood that the subject will respond to the anti-TNFα therapy if there is about a two fold change in the levels of mRNAs in the sample encoded by the nucleic acid sequences of SEQ ID NOS: 8, 9, 28, 37, and 66 as compared to the reference standard of mRNAs encoded by the nucleic acid sequences of SEQ ID NO: 8, 9, 28, 37 and 66.

11. The method of claim 1, further comprising the step of continuing treatment with the anti-TNFα therapy if the subject is determined likely to respond to the therapy.

12. The method of claim 1, further comprising the step of discontinuing treatment with the anti-TNFα therapy if the subject is determined not likely to respond to the therapy.

* * * * *

SEQUENCE LISTING

<160> NUMBER OF SEQ ID NOS: 66

<210> SEQ ID NO 1
<211> LENGTH: 1498
<212> TYPE: DNA
<213> ORGANISM: Homo sapiens

<400> SEQUENCE: 1

| | | | | | |
|---|---|---|---|---|---|
| accaaacctc | ttcgaggcac | aaggcacaac | aggctgctct | gggattctct | tcagccaatc | 60 |
| ttcattgctc | aagtgtctga | agcagccatg | gcagaagtac | ctgagctcgc | cagtgaaatg | 120 |
| atggcttatt | acagtggcaa | tgaggatgac | ttgttctttg | aagctgatgg | ccctaaacag | 180 |
| atgaagtgct | ccttccagga | cctggaccte | tgccctctgg | atggcggcat | ccagctacga | 240 |
| atctccgacc | accactacag | caagggcttc | aggcaggccg | cgtcagttgt | tgtggccatg | 300 |
| gacaagctga | ggaagatgct | ggttccctgc | ccacagacct | tccaggagaa | tgacctgagc | 360 |
| accttctttc | ccttcatctt | tgaagaagaa | cctatcttct | tcgacacatg | ggataacgag | 420 |
| gcttatgtgc | acgatgcacc | tgtacgatca | ctgaactgca | cgctccggga | ctcacagcaa | 480 |
| aaaagcttgg | tgatgtctgg | tccatatgaa | ctgaaagctc | tccacctcca | gggacaggat | 540 |
| atggagcaac | aagtggtgtt | ctccatgtcc | tttgtacaag | gagaagaaag | taatgacaaa | 600 |
| atacctgtgg | ccttgggcct | caaggaaaag | aatctgtacc | tgtcctgcgt | gttgaaagat | 660 |
| gataagccca | ctctacagct | ggagagtgta | gatcccaaaa | attacccaaa | gaagaagatg | 720 |
| gaaaagcgat | ttgtcttcaa | caagatagaa | atcaataaca | agctggaatt | tgagtctgcc | 780 |
| cagttcccca | actggtacat | cagcacctct | caagcagaaa | acatgcccgt | cttcctggga | 840 |
| gggaccaaag | gcggccagga | tataactgac | ttcaccatgc | aatttgtgtc | ttcctaaaga | 900 |
| gagctgtacc | cagagagtcc | tgtgctgaat | gtggactcaa | tccctagggc | tggcagaaag | 960 |
| ggaacagaaa | ggttttgag | tacggctata | gcctggactt | tcctgttgtc | tacaccaatg | 1020 |
| cccaactgcc | tgccttaggg | tagtgctaag | aggatctcct | gtccatcagc | caggacagtc | 1080 |
| agctctctcc | tttcagggcc | aatccccagc | ccttttgttg | agccaggcct | ctctcacctc | 1140 |
| tcctactcac | ttaaagcccg | cctgacagaa | accacggcca | catttggttc | taagaaaccc | 1200 |
| tctgtcattc | gctcccacat | tctgatgagc | aaccgcttcc | ctatttattt | atttatttgt | 1260 |
| ttgtttgttt | tattcattgg | tctaatttat | tcaaggggg | caagaagtag | cagtgtctgt | 1320 |
| aaaagagcct | agtttttaat | agctatgaa | tcaattcaat | ttggactggt | gtgctctctt | 1380 |
| taaatcaagt | cctttaatta | agactgaaaa | tatataagct | cagattattt | aaatgggaat | 1440 |
| atttataaat | gagcaaatat | catactgttc | aatggttctg | aaataaactt | cactgaag | 1498 |

<210> SEQ ID NO 2
<211> LENGTH: 1386
<212> TYPE: DNA
<213> ORGANISM: Homo sapiens
<220> FEATURE:
<221> NAME/KEY: unsure
<222> LOCATION: (491)(1182)
<223> OTHER INFORMATION: Wherein n can be a, c, t, or g

<400> SEQUENCE: 2

| | | | | | |
|---|---|---|---|---|---|
| tgccgaccct | ctgggagaaa | atccagcaag | atgcaagcct | tcagaatctg | ggatgttaac | 60 |
| cagaagacct | tctatctgag | gaacaaccaa | ctagttgccg | gatacttgca | aggaccaaat | 120 |
| gtcaatttag | aagaaaagat | agatgtggta | cccattgagc | tcatgctct | gttcttggga | 180 |

| | |
|---|---|
| atccatggag ggaagatgtg cctgtcctgt gtcaagtctg gtgatgagac cagactccag | 240 |
| ctggaggcag ttaacatcac tgacctgagc gagaacagaa agcaggacaa gcgcttcgcc | 300 |
| ttcatccgct cagacagtgg ccccacacca gtttgtgagg tctgcgctgc ccggtttggt | 360 |
| tcctctgcac agcgatggaa ggaaggcaag agcaagcatg taccgctgaa acacaagat | 420 |
| aactgcataa gtaatgactt tcagtgcaga ttcatagcta acccataaac tgctggggca | 480 |
| aaaatcatct nggaaggctc tgaacctcag aaaggattca caagcgatc tgccgaccct | 540 |
| ctgggagaaa atccagcaag atgcaagcct tcagaatctg ggatgttaac cagaagacct | 600 |
| tctatctgag aacaaccaa ctagttgccg gatacttgca aggaccaaat gtcaatttag | 660 |
| aagaaaagat agatgtggta cccattgagc ctcatgctct gttcttggga atccatggag | 720 |
| ggaagatgtg cctgtcctgt gtcaagtctg gtgatgagac cagactccag ctggaggcag | 780 |
| ttaacatcac tgacctgagc gagaacagaa agcaggacaa gcgcttcgcc ttcatccgct | 840 |
| cagacagtgg ccccacacca gtttgtgagg tctgcgctgc cagtgatgtt aactgcctcc | 900 |
| agctggagtc tggtctcatc accagacttg acacaggaca ggcacatctt ccctccatgg | 960 |
| attcccaaga acagagcatg aggctcaatg gtaccacat ctatcttttc ttctaaattg | 1020 |
| acatttggtc cttgcaagta tccggcaact agttggttgt tcctcagata aaggtcttc | 1080 |
| tggttaacat cccagattct gaaggcttgc atcttgctgg attttctccc agagggtcgg | 1140 |
| cagatcgtct tgtgaatcct ttctgaggtt cagagccttc cnagatgatt tttgccccag | 1200 |
| cagtttatgg gttagctatg aatctgcact gaaagtcatt acttatgcag ttatcttgtg | 1260 |
| ttttcagcgg tacatgcttg ctcttgcctt cttggctttg atgattagtt ttataatccc | 1320 |
| cccttttgagt cagcattgtc ttcacctctt cctcctcctc cacctccttc ttcatacaag | 1380 |
| tcagct | 1386 |

<210> SEQ ID NO 3
<211> LENGTH: 1131
<212> TYPE: DNA
<213> ORGANISM: Homo sapiens

<400> SEQUENCE: 3

| | |
|---|---|
| cattctgccc tcgagcccac cgggaacgaa agagaagctc tatctcccct ccaggagccc | 60 |
| agctatgaac tccttctcca caagcgcctt cggtccagtt gccttctccc tggggctgct | 120 |
| cctggtgttg cctgctgcct tccctgcccc agtaccccca ggagaagatt ccaaagatgt | 180 |
| agccgcccca cacagacagc cactcacctc ttcagaacga attgacaaac aaattcggta | 240 |
| catcctcgac ggcatctcag ccctgagaaa ggagacatgt aacaagagta acatgtgtga | 300 |
| aagcagcaaa gaggcactgg cagaaaacaa cctgaacctt ccaaagatgg ctgaaaaaga | 360 |
| tggatgcttc caatctggat tcaatgagga gacttgcctg gtgaaaatca tcactggtct | 420 |
| tttggagttt gaggtatacc tagagtacct ccagaacaga tttgagagta gtgaggaaca | 480 |
| agccagagct gtgcagatga gtacaaaagt cctgatccag ttcctgcaga aaaggcaaa | 540 |
| gaatctagat gcaataacca cccctgaccc aaccacaaat gccagcctgc tgacgaagct | 600 |
| gcaggcacag aaccagtggc tgcaggacat gacaactcat ctcattctgc gcagctttaa | 660 |
| ggagttcctg cagtccagcc tgagggctct tcggcaaatg tagcatgggc acctcagatt | 720 |
| gttgttgtta atgggcattc cttcttctgg tcagaaacct gtccactggg cacagaactt | 780 |
| atgttgttct ctatggagaa ctaaaagtat gagcgttagg acactatttt aattattttt | 840 |
| aatttattaa tatttaaata tgtgaagctg agttaattta tgtaagtcat atttatattt | 900 |

-continued

```
ttaagaagta ccacttgaaa cattttatgt attagttttg aaataataat ggaaagtggc      960
tatgcagttt gaatatcctt tgtttcagag ccagatcatt tcttggaaag tgtaggctta     1020
cctcaaataa atggctaact tatacatatt tttaaagaaa tatttatatt gtatttatat     1080
aatgtataaa tggtttttat accaataaat ggcattttaa aaaattcagc a              1131
```

<210> SEQ ID NO 4
<211> LENGTH: 2859
<212> TYPE: DNA
<213> ORGANISM: Homo sapiens

<400> SEQUENCE: 4

```
cattcagaga cagaaggtgg atagacaaat ctccaccttc agactggtag gctcctccag       60
aagccatcag acaggaagat gtgaaaatcc ccagcactca tcccagaatc actaagtggc      120
acctgtcctg ggccaaagtc ccaggacaga cctcattgtt cctctgtggg aatacctccc      180
cagggggca tcctggattt cccccttgca acccaggtca gaagtttcat cgtcaaggtt       240
gtttcatctt ttttttcctg tctaacagct ctgactacca cccaaccttg aggcacagtg      300
aagacatcgg tggccactcc aataacagca ggtcacagct gctcttctgg aggtgtccta      360
caggtgaaaa gcccagcgac ccagtcagga tttaagttta cctcaaaaat ggaagatttt      420
aacatggaga gtgacagctt tgaagatttc tggaaaggtg aagatcttag taattacagt      480
tacagctcta ccctgccccc ttttctacta gatgccgccc catgtgaacc agaatccctg      540
gaaatcaaca gtatttttgt ggtcattatc tatgccctgg tattcctgct gagcctgctg      600
ggaaactccc tcgtgatgct ggtcatctta tacagcaggg tcggccgctc cgtcactgat      660
gtctacctgc tgaacctagc cttggccgac ctactctttg ccctgacctt gcccatctgg      720
gccgcctcca aggtgaatgg ctggattttt ggcacattcc tgtgcaaggt ggtctcactc      780
ctgaaggaag tcaacttcta tagtggcatc ctgctactgg cctgcatcag tgtggaccgt      840
tacctggcca ttgtccatgc cacacgcaca ctgacccaga gcgctactt ggtcaaattc      900
atatgtctca gcatctgggg tctgtccttg ctcctggccc tgcctgtctt acttttccga      960
aggaccgtct actcatccaa tgttagccca gcctgctatg aggacatggg caacaataca     1020
gcaaactggc ggatgctgtt acggatcctg cccccagtcct ttggcttcat cgtgccactg     1080
ctgatcatgc tgttctgcta cggattcacc ctgcgtacgc tgtttaaggc ccacatgggg     1140
cagaagcacc gggccatgcg ggtcatcttt gctgtcgtcc tcatcttcct gctctgctgg     1200
ctgcccctaca acctggtcct gctggcagac accctcatga ggacccaggt gatccaggag     1260
acctgtgagc gccgcaatca catcgaccgg gctctggatg ccaccgagat tctgggcatc     1320
cttcacagct gcctcaaccc cctcatctac gccttcattg ccagaagtt cgccatgga      1380
ctcctcaaga ttctagctat acatggcttg atcagcaagg actccctgcc caagacagc      1440
aggccttcct tgttggctc ttcttcaggg cacacttcca ctactctcta agacctcctg     1500
cctaagtgca gccccgtggg gttcctccct tctcttcaca gtcacattcc aagcctcatg     1560
tccactggtt cttcttggtc tcagtgtcaa tgcagccccc attgtggtca caggaagtag     1620
aggaggccac gttcttacta gtttcccttg catggtttag aaagcttgcc ctggtgcctc     1680
acccctgcc ataattacta tgtcatttgc tggagctctg cccatcctgc ccctgagccc     1740
atggcactct atgttctaag aagtgaaaat ctacactcca gtgagacagc tctgcatact     1800
cattaggatg gctagtatca aaagaaagaa aatcaggctg ccaacggggg tgaaccctg      1860
tctctactaa aaatacaaaa aaaaaaaaaa attagccggg cgtggtggtg agtgcctgta     1920
```

| | |
|---|---|
| atcacagcta cttgggaggc tgagatggga gaatcacttg aacccgggag gcagaggttg | 1980 |
| cagtgagccg agattgtgcc cctgcactcc agcctgagcg acagtgagac tctgtctcag | 2040 |
| tccatgaaga tgtagaggag aaactggaac tctcgagcgt tgctgggggg gattgtaaaa | 2100 |
| tggtgtgacc actgcagaag acagtatggc agctttcctc aaaacttcag acatagaatt | 2160 |
| aacacatgat cctgcaattc cacttatagg aattgaccca caagaaatga agcagggac | 2220 |
| ttgaacccat atttgtacac caatattcat agcagcttat tcacaagacc caaaaggcag | 2280 |
| aagcaaccca aatgttcatc aatgaatgaa tgaatggcta agcaaaatgt gatatgtacc | 2340 |
| taacgaagta tccttcagcc tgaaagagga atgaagtact catacatgtt acaacacgga | 2400 |
| cgaaccttga aaactttatg ctaagtgaaa taagccagac atcaacagat aaatagttta | 2460 |
| tgattccacc tacatgaggt actgagagtg aacaaattta cagagacaga aagcagaaca | 2520 |
| gtgattacca gggactgagg ggaggggagc atgggaagtg acggtttaat gggcacaggg | 2580 |
| tttatgttta ggatgttgaa aaagttctgc agataaacag tagtgatagt tgtaccgcaa | 2640 |
| tgtgacttaa tgccactaaa ttgacactta aaaatggttt aaatggtcaa tttgttatg | 2700 |
| tatattttat atcaatttaa aaaaaaacct gagccccaaa aggtatttta atcaccaagg | 2760 |
| ctgattaaac caaggctaga accacctgcc tatatttttt gttaaatgat ttcattcaat | 2820 |
| atcttttttt taataaacca tttttacttg ggtgtttat | 2859 |

```
<210> SEQ ID NO 5
<211> LENGTH: 2354
<212> TYPE: DNA
<213> ORGANISM: Homo sapiens

<400> SEQUENCE: 5
```

| | |
|---|---|
| gctcagggca catgcctccc ctcccaggc cgcggcccag ctgaccctcg gggctccccc | 60 |
| ggcagcggac agggaagggt taaaggcccc cggctccctg cccctgccc tggggaaccc | 120 |
| ctggccctgt ggggacatga actgtgtttg ccgcctggtc ctggtcgtgc tgagcctgtg | 180 |
| gccagataca gctgtcgccc ctgggccacc acctggcccc cctcgagttt cccccagaccc | 240 |
| tcgggccgag ctggacagca ccgtgctcct gacccgctct ctcctggcgg acacgcggca | 300 |
| gctggctgca cagctgaggg acaaattccc agctgacggg gaccacaaac tggattccct | 360 |
| gcccaccctg gccatgagtg cggggggcact gggagctcta cagctcccag gtgtgctgac | 420 |
| aaggctgcga gcggacctac tgtcctacct gcggcacgtg cagtggctgc gccgggcagg | 480 |
| tggctcttcc ctgaagaccc tggagcccga gctgggcacc ctgcaggccc gactggaccg | 540 |
| gctgctgcgc cggctgcagc tcctgatgtc ccgcctggcc ctgccccagc accccggga | 600 |
| cccgccggcg cccccgctgg cgccccctc ctcagcctgg gggggcatca gggccgccca | 660 |
| cgccatcctg ggggggctgc acctgacact tgactgggcc gtgagggggac tgctgctgct | 720 |
| gaagactcgg ctgtgacccg gggcccaaag ccaccaccgt ccttccaaag ccagatctta | 780 |
| tttatttatt tatttcagta ctgggggcga aacagccagg tgatccccc gccattatct | 840 |
| ccccctagtt agagacagtc cttccgtgag gcctgggggg catctgtgcc ttatttatac | 900 |
| ttatttattt caggagcagg ggtgggaggc aggtggactc ctgggtcccc gaggaggagg | 960 |
| ggactgggt cccggattct tgggtctcca agaagtctgt ccacagactt ctgccctggc | 1020 |
| tcttccccat ctaggcctgg gcaggaacat atattattta tttaagcaat tacttttcat | 1080 |
| gttggggtgg ggacggaggg gaaagggaag cctgggtttt tgtacaaaaa tgtgagaaac | 1140 |
| ctttgtgaga cagagaacag ggaattaaat gtgtcataca tatccacttg agggcgattt | 1200 |

```
gtctgagagc tggggctgga tgcttgggta actggggcag ggcaggtgga ggggagacct    1260
ccattcaggt ggaggtcccg agtgggcggg gcagcgactg ggagatgggt cggtcaccca    1320
gacagctctg tggaggcagg gtctgagcct tgcctggggc cccgcactgc atagggcctt    1380
ttgtttgttt tttgagatgg agtctcgctc tgttgcctag gctggagtgc agtgaggcaa    1440
tctgaggtca ctgcaacctc cacctcccgg gttcaagcaa ttctcctgcc tcagcctccc    1500
gattagctgg gatcacaggt gtgcaccacc atgcccagct aattatttat ttcttttgta    1560
tttttagtag agacagggtt tcaccatgtt ggccaggctg gtttcgaact cctgacctca    1620
ggtgatcctc ctgcctcggc ctcccaaagt gctgggatta caggtgtgag ccaccacacc    1680
tgacccatag gtcttcaata aatatttaat ggaaggttcc acaagtcacc ctgtgatcaa    1740
cagtacccgt atgggacaaa gctgcaaggt caagatggtt cattatggct gtgttcacca    1800
tagcaaactg gaaacaatct agatatccaa cagtgagggt taagcaacat ggtgcatctg    1860
tggatagaac gccacccagc cgcccggagc agggactgtc attcagggag ctaaggaga    1920 gaggcttgct tgggatatag aaagatatcc tgacattggc caggcatggt ggctcacgcc    1980
tgtaatcctg gcactttggg aggacgaagc gagtggatca ctgaagtcca agagttcgag    2040
accggcctgc gagacatggc aaaaccctgt ctcaaaaaag aaagaatgat gtcctgacat    2100
gaaacagcag gctacaaaac cactgcatgc tgtgatccca ttttgtgtt tttctttcta    2160 tatatggatt aaaacaaaaa tcctaagggg aaatacgcca aaatgttgac aatgactgtc    2220
tccaggtcaa aggagagagg tgggattgtg ggtgactttt aatgtgtatg attgtctgta    2280
ttttacagaa tttctgccat gactgtgtat tttgcatgac acattttaaa aataataaac    2340
actattttta gaat                                                      2354

<210> SEQ ID NO 6
<211> LENGTH: 1376
<212> TYPE: DNA
<213> ORGANISM: Homo sapiens

<400> SEQUENCE: 6
gtaagaacac tctcgtgagt ctaacggtct tccggatgaa ggctatttga agtcgccata      60
acctggtcag aagtgtgcct gtcggcgggg agagaggcaa tatcaaggtt ttaaatctcg     120
gagaaatggc tttcgtttgc ttggctatcg gatgcttata accttttctg ataagcacaa     180
catttggctg tacttcatct tcagacaccg agataaaagt taaccctcct caggattttg     240
agatagtgga tcccggatac ttaggttatc tctatttgca atggcaaccc ccactgtctc     300
tggatcattt taaggaatgc acagtggaat atgaactaaa ataccgaaac attggtagtg     360
aaacatggaa gaccatcatt actaagaatc tacattacaa agatgggttt gatcttaaca     420
agggcattga agcgaagata cacacgcttt taccatggca atgcacaaat ggatcagaag     480
ttcaaagttc ctgggcagaa actacttatt ggatatcacc acaaggaatt ccagaaacta     540
aagttcagga tatggattgc gtatattaca attggcaata tttactctgt tcttggaaac     600
ctggcatagg tgtacttctt gataccaatt acaacttgtt ttactggtat gagggcttgg     660
atcatgcatt acagtgtgtt gattacatca aggctgatgg acaaaatata ggatgcagat     720
ttccctattt ggaggcatca gactataaag atttctatat ttgtgttaat ggatcatcag     780
agaacaagcc tatcagatcc agttatttca cttttcagct tcaaaatata gttaaacctt     840
tgccgccagt ctatcttact tttactcggg agagttcatg tgaaattaag ctgaatggaa     900
gcataccttt gggaccctatt ccagcaaggt gttttgatta tgaaattgag atcagagaag     960
```

-continued

```
atgatactac cttggtgact gctacagttg aaaatgaaac atacaccttg aaaacaacaa   1020
atgaaacccg acaattatgc tttgtagtaa gaagcaaagt gaatatttat tgctcagatg   1080
acggaatttg gagtgagtgg agtgataaac aatgctggga aggtgaagac ctatcgaaga   1140
aaactttgct acgtttctgg ctaccatttg gtttcatctt aatattagtt atatttgtaa   1200
ccggtctgct tttgcgtaag ccaaacacct acccaaaaat gattccagaa ttttctgtg    1260 atacatgaag actttccata tcaagagaca tggtattgac tcaacagttt ccagtcatgg   1320
ccaaatgttc aatatgagtc tcaataaact gaattttct tgcgaatgtt gaaaaa        1376
```

<210> SEQ ID NO 7
<211> LENGTH: 1049
<212> TYPE: DNA
<213> ORGANISM: Homo sapiens

<400> SEQUENCE: 7

```
aaaacaacag gaagcagctt acaaactcgg tgaacaactg agggaaccaa accagagacg    60
cgctgaacag agagaatcag gctcaaagca agtggaagtg ggcagagatt ccaccaggac   120
tggtgcaagg cgcagagcca gccagatttg agaagaaggc aaaaagatgc tggggagcag   180
agctgtaatg ctgctgttgc tgctgccctg acagctcag  ggcagagctg tgcctggggg   240
cagcagccct gcctggactc agtgccagca gctttcacag aagctctgca cactggcctg   300
gagtgcacat ccactagtgg gacacatgga tctaagagaa gagggagatg aagagactac   360
aaatgatgtt ccccatatcc agtgtggaga tggctgtgac ccccaaggac tcagggacaa   420
cagtcagttc tgcttgcaaa ggatccacca gggtctgatt ttttatgaga agctgctagg   480
atcggatatt ttcacagggg agccttctct gctccctgat agccctgtgg gccagcttca   540
tgcctcccta ctgggcctca gccaactcct gcagcctgag ggtcaccact gggagactca   600
gcagattcca agcctcagtc ccagccagcc atggcagcgt ctccttctcc gcttcaaaat   660
ccttcgcagc ctccaggcct tgtggctgt agccgcccgg gtctttgccc atggagcagc    720
aaccctgagt ccctaaaggc agcagctcaa ggatggcact cagatctcca tggcccagca   780
aggccaagat aaatctacca ccccaggcac ctgtgagcca acaggttaat tagtccatta   840
attttagtgg gacctgcata tgttgaaaat taccaatact gactgacatg tgatgctgac   900
ctatgataag gttgagtatt tattagatgg aagggaaatt tgggggatta tttatcctcc   960
tggggacagt ttggggagga ttatttattg tatttatatt gaattatgta cttttttcaa   1020
taaagtctta tttttgtggc taaaaaaaa                                     1049
```

<210> SEQ ID NO 8
<211> LENGTH: 1975
<212> TYPE: DNA
<213> ORGANISM: Homo sapiens

<400> SEQUENCE: 8

```
cttgcctgca aacctttact tctgaaatga cttccacggc tgggacggga accttccacc    60
cacagctatg cctctgattg gtgaatggtg aaggtgcctg tctaactttt ctgtaaaaag   120
aaccagctgc ctccaggcag ccagccctca agcatcactt acaggaccag agggacaaga   180
catgactgtg atgaggagct gctttcgcca atttaacacc aagaagaatt gaggctgctt   240
gggaggaagg ccaggaggaa cacgagactg agagatgaat tttcaacaga ggctgcaaag   300
cctgtggact ttagccagac ccttctgccc tcctttgctg gcgacagcct tcaaatgca    360 gatggttgtg ctcccttgcc tgggttttac cctgcttctc tggagccagg tatcaggggc   420
```

```
ccagggccaa gaattccact ttgggccctg ccaagtgaag ggggttgttc cccagaaact      480
gtgggaagcc ttctgggctg tgaaagacac tatgcaagct caggataaca tcacgagtgc      540
ccggctgctg cagcaggagg ttctgcagaa cgtctcggat gctgagagct gttaccttgt      600
ccacaccctg ctggagttct acttgaaaac tgttttcaaa aactaccaca atagaacagt      660
tgaagtcagg actctgaagt cattctctac tctggccaac aactttgttc tcatcgtgtc      720
acaactgcaa cccagtcaag aaaatgagat gttttccatc agagacagtg cacacaggcg      780
gtttctgcta ttccggagag cattcaaaca gttggacgta aagcagctc tgaccaaagc       840 ccttgggaa gtggacattc ttctgacctg gatgcagaaa ttctacaagc tctgaatgtc        900
tagaccagga cctccctccc cctggcactg gtttgttccc tgtgtcattt caaacagtct      960
cccttcctat gctgttcact ggacacttca cgcccttggc catgggtccc attcttggcc     1020
caggattatt gtcaaagaag tcattcttta agcagcgcca gtgacagtca gggaaggtgc     1080
ctctggatgc tgtgaagagt ctacagagaa gattcttgta tttattacaa ctctatttaa     1140
ttaatgtcag tatttcaact gaagttctat ttatttgtga gactgtaagt tacatgaagg     1200
cagcagaata ttgtgcccca tgcttcttta cccctcacaa tccttgccac agtgtgggc      1260 agtggatggg tgcttagtaa gtacttaata aactgtggtg cttttttttgg cctgtctttg    1320 gattgttaaa aaacagagag ggatgcttgg atgtaaaact gaacttcaga gcatgaaaat     1380
cacactgtct tctgatatct gcagggacag agcattgggg tgggggtaag gtgcatctgt     1440
ttgaaaagta aacgataaaa tgtggattaa agtgcccagc acaaagcaga tcctcaataa     1500
acatttcatt tcccacccac actcgccagc tcaccccatc atcccttttcc cttggtgccc     1560 tcctttttt tttatcctag tcattcttcc ctaatcttcc acttgagtgt caagctgacc      1620
ttgctgatgg tgacattgca cctggatgta ctatccaatc tgtgatgaca ttccctgcta    1680
ataaaagaca acataactca agtctggcag actttcttct ctatttctgg atgaatgccc    1740
agtgagactg tgttgtacag ctagaaaagg ccttcttccc aatagcaagg ctgtgcatct    1800
agcctcaagc tctggctgaa cttttgtggtc gacatcaatc taaagataca gtgtctgact    1860
ataaccttgt tccaaaaacc taggcaaaga gtatatgtag gaggtgggat atcacttcca    1920
tgacataagt gctattgcag agccgtggcc acccaggaac tcctgactgc tttcc         1975
```

<210> SEQ ID NO 9
<211> LENGTH: 307
<212> TYPE: DNA
<213> ORGANISM: Homo sapiens
<220> FEATURE:
<221> NAME/KEY: unsure
<222> LOCATION: (60)
<223> OTHER INFORMATION: Wherein n can be a, c, t, or g

<400> SEQUENCE: 9

```
agttagaggc tgtacaaggc ccccactgcc tgtcggttgc ttggattccc tgacgtaagn       60
tggatattaa aaatctgtaa atcaggacag gtggtgcaaa tggcgctggg aggtgtacac      120
ggaggtctct gtaaaagcag acccacctcc cagcgccggg aagcccgtct tgggtcctcg      180
ctgctggctg ctccccctgg tggtggatcc tggaattttc tcacgcagga gccattgctc      240
tcctagaggg ggtctcagaa actgcgaggc cagttccttg gagggacatg actaatttat      300
cgatttt                                                                307
```

<210> SEQ ID NO 10
<211> LENGTH: 490
<212> TYPE: DNA

<213> ORGANISM: Homo sapiens

<400> SEQUENCE: 10

| | | | | | |
|---|---|---|---|---|---|
| ggatacccca | ttgtgaagcc | agggcccaac | tgtggatttg | aaaaactgg | cattattgat | 60 |
| tatggaatcc | gtctcaatag | gagtgaaaga | tgggatgcct | attgctacaa | cccacacgca | 120 |
| aaggagtgtg | gtggcgtctt | tacagatcca | aagcaaattt | ttaaatctcc | aggcttccca | 180 |
| aatgagtacg | aagataacca | aatctgctac | tggcacatta | gactcaagta | tggtcagcgt | 240 |
| attcacctga | gttttttaga | ttttgacctt | gaagatgacc | caggttgctt | ggctgattat | 300 |
| gttgaaatat | atgacagtta | cgatgatgtc | catggctttg | tgggaagata | ctgtggagat | 360 |
| gagcttccag | atgacatcat | cagtacagga | aatgtcatga | ccttgaagtt | tctaagtgat | 420 |
| gcttcagtga | cagctggagg | tttccaaatc | aaatatgttg | caatggatcc | tgtatccaaa | 480 |
| tccagtcaag | | | | | 490 |

<210> SEQ ID NO 11
<211> LENGTH: 380
<212> TYPE: DNA
<213> ORGANISM: Homo sapiens

<400> SEQUENCE: 11

| | | | | | |
|---|---|---|---|---|---|
| tactgcttgc | agtaattcaa | ctggaaatta | aaaaaaaaaa | actagactcc | attgtgcctt | 60 |
| actaaatatg | ggaatgtcta | acttaaatag | ctttgagatt | tcagctatgc | tagaggcttt | 120 |
| tattagaaag | ccatattttt | ttctgtaaaa | gttactaata | tatctgtaac | actattacag | 180 |
| tattgctatt | tatattcatt | cagatataag | atttgtacat | attatcatcc | tataaagaaa | 240 |
| cggtatgact | taattttaga | aagaaaatta | tattctgttt | attatgacaa | atgaaagaga | 300 |
| aaatatatat | ttttaatgga | aagtttgtag | cattttctta | ataggtactg | ccatattttt | 360 |
| ctgtgtggag | tattttata | | | | 380 |

<210> SEQ ID NO 12
<211> LENGTH: 3003
<212> TYPE: DNA
<213> ORGANISM: Homo sapiens

<400> SEQUENCE: 12

| | | | | | |
|---|---|---|---|---|---|
| tcggggagag | aagctggact | gcagctggtt | tcaggaactt | ctcttgacga | aagagagac | 60 |
| caaggaggcc | aagcagggc | tgggccagag | gtgccaacat | ggggaaactg | aggctcggct | 120 |
| cggaaaggtg | aagtaacttg | tccaagatca | caaagctggt | gaacatcaag | ttggtgctat | 180 |
| ggcaaggctg | ggaaactgca | gcctgacttg | ggctgccctg | atcatcctgc | tgctccccgg | 240 |
| aagtctggag | gagtgcgggc | acatcagtgt | ctcagccccc | atcgtccacc | tgggggatcc | 300 |
| catcacagcc | tcctgcatca | tcaagcagaa | ctgcagccat | ctggaccgg | agccacagat | 360 |
| tctgtggaga | ctgggagcag | agcttcagcc | cggggcagg | cagcagcgtc | tgtctgatgg | 420 |
| gacccaggaa | tctatcatca | ccctgccccca | cctcaaccac | actcaggcct | ttctctcctg | 480 |
| ctgcctgaac | tggggcaaca | gcctgcagat | cctggaccag | gttgagctgc | gcgcaggcta | 540 |
| ccctccagcc | atacccccaca | acctctcctg | cctcatgaac | ctcacaacca | gcagcctcat | 600 |
| ctgccagtgg | gagccaggac | ctgagaccca | cctacccacc | agcttcactc | tgaagagttt | 660 |
| caagagccgg | ggcaactgtc | agacccaagg | ggactccatc | ctggactgcg | tgcccaagga | 720 |
| cgggcagagc | cactgctgca | tcccacgcaa | acacctgctg | ttgtaccaga | atatgggcat | 780 |
| ctgggtgcag | gcagagaatg | cgctggggac | cagcatgtcc | ccacaactgt | gtcttgatcc | 840 |

```
catggatgtt gtgaaactgg agcccccat gctgcggacc atggacccca gccctgaagc      900
ggcccctccc caggcaggct gcctacagct gtgctgggag ccatggcagc caggcctgca      960
cataaatcag aagtgtgagc tgcgccacaa gccgcagcgt ggagaagcca gctgggcact     1020
ggtgggcccc ctccccttgg aggcccttca gtatgagctc tgcgggctcc tcccagccac     1080
ggcctacacc ctgcagatac gctgcatccg ctggcccctg cctggccact ggagcgactg     1140
gagcccagc  ctggagctga gaactaccga acgggccccc actgtcagac tggacacatg     1200
gtggcggcag aggcagctgg accccaggac agtgcagctg ttctggaagc cagtgcccct     1260
ggaggaagac agcggacgga tccaaggtta tgtggtttct ggagaccct  caggccaggc     1320
tgggccatc  ctgcccctct gcaacaccac agagctcagc tgcaccttcc acctgccttc     1380
agaagcccag gaggtggccc ttgtggccta taactcagcc gggacctctc gtcccactcc     1440
ggtggtcttc tcagaaagca gaggcccagc tctgaccaga ctccatgcca tggcccgaga     1500
ccctcacagc ctctgggtag ctgggagcc  cccaatcca tggcctcagg gctatgtgat     1560
tgagtggggc ctgggccccc ccagcgcgag caatagcaac aagacctgga ggatggaaca     1620
gaatgggaga gccacggggt ttctgctgaa ggagaacatc aggcccttt  agctctatga     1680
gatcatcgtg actcccttgt accaggacac catgggaccc tcccagcatg tctatgccta     1740
ctctcaagaa atggctccct cccatgcccc agagctgcat ctaaagcaca ttggcaagac     1800
ctgggcacag ctggagtggg tgcctgagcc ccctgagctg gggaagagcc cccttaccca     1860
ctacaccatc ttctggacca acgctcagaa ccagtccttc tccgccatcc tgaatgcctc     1920
ctcccgtggc tttgtcctcc atggcctgga gcccgccagt ctgtatcaca tccacctcat     1980
ggctgccagc caggctgggg ccaccaacag tacagtcctc accctgatga ccttgacccc     2040
agagggtcg  gagctacaca tcatcctggg cctgttcggc ctcctgctgt tgctcacctg     2100
cctctgtgga actgcctggc tctgttgcag ccccaacagg aagaatcccc tctggccaag     2160
tgtcccagac ccagctcaca gcagcctggg ctcctgggtg cccacaatca tggaggagga     2220
tgccttccag ctgccggcc  ttggcacgcc acccatcacc aagctcacag tgctggagga     2280
ggatgaaaag aagccggtgc cctggagtc  ccataacagc tcagagacct gtggcctccc     2340
cactctggtc cagacctatg tgctccaggg ggacccaaga gcagtttcca cccagccccc     2400
atcccagtct ggcaccagcg atcaggtcct ttatgggcag ctgctgggca gccccacaag     2460
cccagggcca gggcactatc tccgctgtga ctccactcag cccctcttgg cgggcctcac     2520
ccccagcccc aagtcctatg agaacctctg gttccaggcc agcccttggg gaccctggt      2580
aaccccagcc ccaagccagg aggacgactg tgtctttggg ccactgctca acttccccct     2640
cctgcagggga tccgggtcc atgggatgga ggcgctgggg agcttctagg cttcctggg      2700
gttcccttct tgggcctgcc tcttaaaggc ctgagctagc tggagaagag gggagggtcc     2760
ataagcccat gactaaaaac taccccagcc caggctctca ccatctccag tcaccagcat     2820
ctccctctcc tcccaatctc cataggctgg gcctcccagg cgatctgcat actttaagga     2880
ccagatcatg ctccatccag ccccacccaa tggccttttg tgcttgtttc ctataacttc     2940
agtattgtaa actagttttt ggtttgcagt ttttgttgtt gtttatagac actcttgggt     3000
gta                                                                    3003
```

<210> SEQ ID NO 13
<211> LENGTH: 468
<212> TYPE: DNA
<213> ORGANISM: Homo sapiens -continued

```
<400> SEQUENCE: 13
gatttacaaa ggtcctccca ttgcaaagca gtgtttgtcc taatttatat attgtttttc    60
tagttcattt tgtgtttcca acttttcatg taaaatttta attattttg aatgtgtgga    120 tgtgagactg aggtgccttt tggtactgaa attcttttc catgtacctg aagtgttact    180
tttgtgatat aggaaatcct tgtatatata ctttattggt ccctaggctt cctattttgt    240
taccttgctt tctctatggc atccaccatt ttgattgttc tacttttatg atatgttttc    300
ataagtggtt aagcaagtat tctcgttact tttgctctta aatccctatt cattacagca    360
atgttggtgg tcaaagaaaa tgataaacaa cttgaatgtt caatggtcct gaaatacata    420
acaacatttt agtacattgt aaagtagaat cctctgttca taatgaac                468

<210> SEQ ID NO 14
<211> LENGTH: 846
<212> TYPE: DNA
<213> ORGANISM: Homo sapiens

<400> SEQUENCE: 14
atgtggttct tgacaactct gctcctttgg gttccagttg atgggcaagt ggacaccaca    60
aaggcagtga tcactttgca gcctccatgg gtcagcgtgt tccaagagga aaccgtaacc    120
ttgcactgtg aggtgctcca tctgcctggg agcagctcca cacagtggtt tctcaatggc    180
acagccactc agacctcgac ccccagctac agaatcacct ctgccagtgt caatgacagt    240
ggtgaataca ggtgccagag aggtctctca gggcgaagtg accccataca gctgaaaatc    300
cacagaggct ggctactact gcaggtctcc agcagagtct tcatggaagg agaacctctg    360
gccttgaggt gtcatgcgtg gaaggataag ctggtgtaca atgtgcttta ctatcgaaat    420
ggcaaagcct ttaagttttt ccactggaat tctaacctca ccattctgaa aaccaacata    480
agtcacaatg gcacctacca ttgctcaggc atgggaaagc atcgctacac atcagcagga    540
atatcacaat acactgtgaa aggcctccag ttaccaactc ctgtctggtt tcatgtcctt    600
ttctatctgg cagtgggaat aatgttttta gtgaacactg ttctctgggt gacaatacgt    660
aaagaactga aaagaagaa aaagtggaat ttagaaatct ctttggattc tggtcatgag    720
aagaaggtaa tttccagcct tcaagaagac agacatttag aagaagagct gaaatgtcag    780
gaacaaaaag aagaacagct gcaggaaggg gtgcaccgga aggagcccca gggggccacg    840
tagcag                                                             846

<210> SEQ ID NO 15
<211> LENGTH: 2411
<212> TYPE: DNA
<213> ORGANISM: Homo sapiens

<400> SEQUENCE: 15
gtctcttaaa acccactgga cgttggcaca gtgctgggat gactatggag acccaaatgt    60
ctcagaatgt atgtcccaga aacctgtggc tgcttcaacc attgacagtt ttgctgctgc    120
tggcttctgc agacagtcaa gctgctcccc caaaggctgt gctgaaactt gagccccgt    180 ggatcaacgt gctccaggag gactctgtga ctctgacatg ccagggggct cgcagccctg    240
agagcgactc cattcagtgg ttccacaatg gaatctcat tcccacccac acgcagccca    300
gctacaggtt caaggccaac aacaatgaca gcggggagta cacgtgccag actggccaga    360
ccagcctcag cgaccctgtg catctgactg tgctttccga atggctggtg ctccagaccc    420
ctcacctgga gttccaggag ggagaaacca tcatgctgag gtgccacagc tggaaggaca    480
```

| | |
|---|---:|
| agcctctggt caaggtcaca ttcttccaga atggaaaatc ccagaaattc tcccatttgg | 540 |
| atcccacctt ctccatccca caagcaaacc acagtcacag tggtgattac cactgcacag | 600 |
| gaaacatagg ctacacgctg ttctcatcca agcctgtgac catcactgtc caagtgccca | 660 |
| gcatgggcag ctcttcacca atggggatca ttgtggctgt ggtcattgcg actgctgtag | 720 |
| cagccattgt tgctgctgta gtggccttga tctactgcag gaaaaagcgg atttcagcca | 780 |
| attccactga tcctgtgaag gctgcccaat ttgagccacc tggacgtcaa atgattgcca | 840 |
| tcagaaagag acaacttgaa gaaaccaaca atgactatga acagctgac ggcggctaca | 900 |
| tgactctgaa ccccagggca cctactgacg atgataaaaa catctacctg actcttcctc | 960 |
| ccaacgacca tgtcaacagt aataactaaa gagtaacgtt atgccatgtg gtcatactct | 1020 |
| cagcttgctg agtggatgac aaaagaggg gaattgttaa aggaaatttt aaatggagac | 1080 |
| tggaaaaatc ctgagcaaac aaaaccacct ggcccttaga aatagcttta actttgctta | 1140 |
| aactacaaac acaagcaaaa cttcacgggg tcatactaca tacaagcata agcaaaactt | 1200 |
| aacttggatc atttctggta aatgcttatg ttagaaataa gacaaccca gccaatcaca | 1260 |
| agcagcctac taacatataa ttaggtgact agggactttc taagaagata cctaccccca | 1320 |
| aaaacaatt atgtaattga aaaccaaccg attgcctta ttttgcttcc acattttccc | 1380 |
| aataaatact tgcctgtgac attttgccac tggaacacta aacttcatga attgcgcctc | 1440 |
| agatttttcc tttaacatct tttttttttt tgacagagtc tcaatctgtt acccaggctg | 1500 |
| gagtgcagtg gtgctatctt ggctcactgc aaacccgcct cccaggttta agcgattctc | 1560 |
| atgcctcagc ctcccagtag ctgggattag aggcatgtgc catcataccc agctaatttt | 1620 |
| tgtattttt attttttttt tttagtagag acagggtttc gcaatgttgg ccaggccgat | 1680 |
| ctcgaacttc tggcctctag cgatctgccc gcctcggcct cccaaagtgc tgggatgacc | 1740 |
| agcatcagcc ccaatgtcca gcctctttaa catcttcttt cctatgccct ctctgtggat | 1800 |
| ccctactgct ggtttctgcc ttctccatgc tgagaacaaa atcacctatt cactgcttat | 1860 |
| gcagtcggaa gctccagaag aacaaagagc ccaattacca gaaccacatt aagtctccat | 1920 |
| tgttttgcct tgggatttga gaagagaatt agagaggtga ggatctggta tttcctggac | 1980 |
| taaattcccc ttggggaaga cgaagggatg ctgcagttcc aaaagagaag gactcttcca | 2040 |
| gagtcatcta cctgagtccc aaagctccct gtcctgaaag ccacagacaa tatggtccca | 2100 |
| aatgactgac tgcaccttct gtgcctcagc cgttcttgac atcaagaatc ttctgttcca | 2160 |
| catccacaca gccaatacaa ttagtcaaac cactgttatt aacagatgta gcaacatgag | 2220 |
| aaacgcttat gttacaggtt acatgagagc aatcatgtaa gtctatatga cttcagaaat | 2280 |
| gttaaaatag actaacctct aacaacaaat taaaagtgat tgtttcaagg tgatgcaatt | 2340 |
| attgatgacc tattttattt ttctataatg atcatatatt accttgtaa taaaacatta | 2400 |
| taaccaaaac a | 2411 |

<210> SEQ ID NO 16
<211> LENGTH: 1977
<212> TYPE: DNA
<213> ORGANISM: Homo sapiens

<400> SEQUENCE: 16

| | |
|---|---:|
| cactccagtg tggcatcatg tggcagctgc tcctcccaac tgctctgcta cttctagttt | 60 |
| cagctggcat gcggactgaa gatctcccaa aggctgtggt gttcctggag cctcaatggt | 120 |
| acagggtgct cgagaaggac agtgtgactc tgaagtgcca gggagcctac tcccctgagg | 180 |

-continued

| | |
|---|---:|
| acaattccac acagtggttt cacaatgaga acctcatctc aagccaggcc tcgagctact | 240 |
| tcattgacgc tgccacagtc gacgacagtg gagagtacag gtgccagaca aacctctcca | 300 |
| ccctcagtga cccggtgcag ctagaagtcc atgtcggctg gctgttgctc caggcccctc | 360 |
| ggtgggtgtt caaggaggaa gaccctattc acctgaggtg tcacagctgg aagaacactg | 420 |
| ctctgcataa ggtcacatat ttacagaatg gcaagacag gaagtatttt catcataatt | 480 |
| ctgacttcca cattccaaaa gccacactca agatagcgg ctcctacttc tgcaggggc | 540 |
| ttgttgggag taaaaatgtg tcttcagaga ctgtgaacat caccatcact caaggtttgg | 600 |
| cagtgtcaac catctcatca ttctctccac ctgggtacca agtctctttc tgcttggtga | 660 |
| tggtactcct ttttgcagtg gacacaggac tatatttctc tgtgaagaca aacatttgaa | 720 |
| gctcaacaag agactggaag gaccataaac ttaaatggag aaaggaccct caagacaaat | 780 |
| gaccccatc ccatgggagt aataagagca gtggcagcag catctctgaa catttctctg | 840 |
| gatttgcaac cccatcatcc tcaggcctct ctacaagcag caggaaacat agaactcaga | 900 |
| gccagatcct ttatccaact ctcgattttt ccttggtctc cagtggaagg gaaaagccca | 960 |
| tgatcttcaa gcagggaagc cccagtgagt agctgcattc ctagaaattg aagtttcaga | 1020 |
| gctacacaaa cactttttct gtcccaacca ttccctcaca gtaaaacaac aatacaggct | 1080 |
| agggatggta atcctttaaa catacaaaaa ttgctcgtat tataaattac ccagtttaga | 1140 |
| ggggaaaaaa gaaataatt attcctaaac aaatggataa gtagaattaa tgattgaggc | 1200 |
| aggaccctac agagtgtggg aactgctggg gatctagaga attcagtggg accaatgaaa | 1260 |
| gcatggctga gaaatagcag ggtagtccag gatagtctaa gggaggtgtt cccatctgag | 1320 |
| cccagagata agggtgtctt cctagaacat tagccgtagt ggaattaaca ggaaatcatg | 1380 |
| agggtgacgt agaattgagt cttccagggg actctatcag aactggacca tttccaagta | 1440 |
| tataacgatg agccctctaa tgctaggagt agcaaatggt cctaggaagg ggactgagga | 1500 |
| ttggggtggg ggtggggtgg aaaagaaagt acagaacaaa ccctgtgtca ctgtcccaag | 1560 |
| ttaagctaag tgaacagaac tatctcagca tcagaatgag aatgagaaag cctgagaaga | 1620 |
| aagaaccaac cacaagcaca caggaaggaa agcgcaggag gtgaaaatgc tttcttggcc | 1680 |
| agggtagtaa gaattagagg ttaatgcagg gactgtaaaa ccaccttttc tgcttcaatg | 1740 |
| tctagttcct gtatagcttt gttcattgca tttattaaac aaatgttgta taccaaatac | 1800 |
| taaatgtact actgagcttc actgagttac gctgtgaaac tttcaaatcc ttcttcagtc | 1860 |
| agttccaatg aggtggggat ggagaagaca attgttgctt atgaaaaaaa gctttagctg | 1920 |
| tctcctgttt tgtaagcttt cagtgcaaca tttcttggtt ccaataaagc attttac | 1977 |

<210> SEQ ID NO 17
<211> LENGTH: 1452
<212> TYPE: DNA
<213> ORGANISM: Homo sapiens

<400> SEQUENCE: 17

| | |
|---|---:|
| tcatccatcc gcagagcagg gcagtgggag gagacgccat gaccccatc ctcacggtcc | 60 |
| tgatctgtct cgggcaccte cccaagccca ccctctgggc tgagccaggc tctgtgatca | 120 |
| tccaggaag tcctgtgacc ctcaggtgtc agggagccct tcaggctgag gagtaccatc | 180 |
| tatataggga aaacaaatca gcatcctggg ttagacggat acaagagcct gggaagaatg | 240 |
| gccagttccc catcccatcc atcacctggg aacacgcagg gcggtatcac tgtcagtact | 300 |
| acagccacaa tcactcatca gagtacagtg accccctgga gctggtggtg acaggagcct | 360 |

| | |
|---|---:|
| acagcaaacc cacccctctca gctctgccca gccctgtggt gaccttagga gggaacgtga | 420 |
| ccctccagtg tgtctcacag gtggcatttg acggcttcat tctgtgtaag gaaggagaag | 480 |
| atgaacaccc acaacgcctg aactcccatt cccatgcccg tgggtggtcc tgggccatct | 540 |
| tctccgtggg ccccgtgagc ccgagtcgca ggtggtcgta caggtgctat gcttatgact | 600 |
| cgaactctcc ctatgtgtgg tctctaccca gtgatctcct ggagctcctg gtcccaggtg | 660 |
| tttctaagaa gccatcactc tcagtgcagc caggtcctat ggtggcccct ggggagagcc | 720 |
| tgaccctcca gtgtgtctct gatgtcggct acgacagatt tgttctgtat aaggagggag | 780 |
| aacgtgactt cctccagcgc cctggttggc agccccaggc tgggctctcc caggccaact | 840 |
| tcaccctggg ccctgtgagc ccctcccacg ggggccagta cagatgctac agtgcacaca | 900 |
| acctctcctc cgagtggtcg gcccccagtg acccctgga catcctgatc acaggacagt | 960 |
| tctatgacag accctctctc tcggtgcagc cggtccccac agtagcccca ggaaagaacg | 1020 |
| tgaccctgct gtgtcagtca cgggggcagt tccacacttt ccttctgacc aaggaggggg | 1080 |
| caggccatcc cccactgcat ctgagatcag agcaccaagc tcagcagaac caggctgaat | 1140 |
| tccgcatggg tcctgtgacc tcagcccacg tggggaccta cagatgctac agctcactca | 1200 |
| gctccaaccc ctacctgctg tctctcccca gtgaccccct ggagctcgtg gtctcagcat | 1260 |
| ccctaggcca acacccccag gattacacag tggagaatct catccgcatg ggtgtggctg | 1320 |
| gcttggtcct ggtggtcctc gggattctgc tatttgaggc tcagcacagc cagagaagcc | 1380 |
| tacaagatgc agccgggagg tgaacagcag agaggacaat gcatacttca gcgtggtgga | 1440 |
| gcctcaggga ca | 1452 |

<210> SEQ ID NO 18
<211> LENGTH: 2879
<212> TYPE: DNA
<213> ORGANISM: Homo sapiens

<400> SEQUENCE: 18

| | |
|---|---:|
| aaaaagctat ttaggtgaca ctatagaagg tacgcctgca ggtaaccggt ccggaattcc | 60 |
| cgggtcgacc cacgcgtccg ggggaagcca ctgctaccct catcaggaag gcagacaca | 120 |
| agaagcacca gttctatttg ctgctacatc ccggctctcg caccgagggc tcatccatcc | 180 |
| gcagagcagg gcagtgggag gagacgccat gaccccatc gtcacagtcc tgatctgtct | 240 |
| cgggctgagt ctgggccca ggacccgcgt gcagacaggg accatcccca gcccaccct | 300 |
| gtgggctgag ccagactctg tgatcaccca ggggagtccc gtcaccctca gttgtcaggg | 360 |
| gagccttgaa gcccaggagt accgtctata tagggagaaa aaatcagcat cttggattac | 420 |
| acggatacga ccagagcttg tgaagaacgg ccagttccac atcccatcca tcacctggga | 480 |
| acacacaggg cgatatggct gtcagtatta cagccgcgct cggtggtctg agctcagtga | 540 |
| cccccctggtg ctggtgatga caggagccta cccaaaaccc accctctcag cccagcccag | 600 |
| ccctgtggtg acctcaggag gaagggtgac cctccagtgt gagtcacagg tggcatttgg | 660 |
| cggcttcatt ctgtgtaagg aaggagaaga tgaacaccca caatgcctga actcccagcc | 720 |
| ccatgcccgt gggtcgtccc gcgccatctt ctccgtgggc cccgtgagcc gaatcgcag | 780 |
| gtggtcgcac aggtgctatg gttatgactg gaactctccc tatgtgtggt cttcacccag | 840 |
| tgatctcctg gagctcctgg tcccaggtgt ttctaagaag ccatcactct cagtgcagcc | 900 |
| gggtcctgtc atggcccctg gggaagcct gaccctccag tgtgtctctg atgtcggcta | 960 |
| tgacagattt gttctgtaca aggaggggga acgtgacctt cgccagctcc ctggccggca | 1020 |

```
gccccaggct gggctctccc aggccaactt caccctgggc cctgtgagcc gctcctacgg    1080
gggccagtac agatgctacg gtgcacacaa cctctcctct gagtgctcgg ccccagcga    1140 ccccctggac atcctgatca caggacagat ccgtggcaca cccttcatct cagtgcagcc    1200
aggccccaca gtggcctcag gagagaacgt gaccctgctg tgtcagtcat ggcggcagtt    1260
ccacactttc cttctgacca aggcgggagc agctgatgcc ccactccgtc taagatcaat    1320
acacgaatat cctaagtacc aggctgaatt ccccatgagt cctgtgacct cagcccacgc    1380
ggggacctac aggtgctacg gctcactcaa ctccgacccc tacctgctgt ctcaccccag    1440
tgagcccctg gagctcgtgg tctcaggacc tccatgggg tccagccccc cacccaccgg    1500
tcccatctcc acacctggcc ctgaggacca gcccctcacc ccactgggt cggatcccca    1560 aagtggtctg ggaaggcacc tgggggttgt gatcggcatc ttggtggccg tcgtcctact    1620
gctcctcctc ctcctcctcc tcttcctcat cctccgacat cgacgtcagg gcaaacactg    1680
gacatcgacc cagagaaagg ctgatttcca acatcctgca ggggctgtgg ggccagagcc    1740
cacagacaga ggcctgcagt ggaggtccag cccagctgcc gacgcccagg aagaaaacct    1800
ctatgctgcc gtgaaggaca cacagccga agatgggtg gagatggaca ctcgggctgc    1860
tgcatctgaa gccccccagg atgtgaccta cgcccagctg cacagcttga ccctcagacg    1920
gaaggcaact gagcctcctc catcccagga aagggaacct ccagctgagc ccagcatcta    1980
cgccaccctg gccatccact agcccggagg gtacgcagac tccacactca gtagaaggag    2040
actcaggact gctgaaggca cgggagctgc ccccagtgga caccaatgaa ccccagtcag    2100
cctggacccc taacaaagac catgaggaga tgctgggaac tttgggactc acttgattct    2160
gcagtcgaaa taactaatat ccctacattt tttaattaaa gcaacagact tctcaataat    2220
caatgagtta accgagaaaa ctaaaatcag aagtaagaat gtgctttaaa ctgaatcaca    2280
atataaatat tacacatcac acaatgaaat tgaaaaagta caaaccacaa atgaaaaaag    2340
tagaaacgaa aaaaaaaac taggaaatga atgacgttgg cttcgtata aggaattag    2400 aaaaagaata accaattatt ccaaatgaag gtgtaagaaa gggaataaga agaagaagag    2460
ttgctcatga ggaaaaacca aaacttgaaa attcaacaaa gccaatgaag ctcattcttg    2520
aaaatattaa ttacagtcat aaatcctaac tacattgagc aagagaaaga aagagcaggc    2580
acgcatttcc atatgggagt gagccagcag acagcccagc agatcctaca cacattttca    2640
caaactaacc ccagaacagg ctgcaaacct ataccaatat actagaaaat gcagattaaa    2700
tggatgaaat attcaaaact ggagtttaca taatgaacgt aagagtaatc agagaatctg    2760
actcatttta aatgtgtgtg tatgtgtgtg tatatatgg tgtgtgtgtg tgtgtgtgtg    2820
tgtgtgtgaa aaacattgac tgtaataaaa atgttcccat cgtaaaaaaa aaaaaaaaa    2879
```

<210> SEQ ID NO 19
<211> LENGTH: 2066
<212> TYPE: DNA
<213> ORGANISM: Homo sapiens

<400> SEQUENCE: 19

```
ccatgacgcc cgccctcaca gccctgctct gccttgggct gagtctgggc cccaggaccc      60
gcatgcaggc agggcccttc cccaaaccca ccctctgggc tgagccaggc tctgtgatca     120
gctgggggag ccccgtgacc atctggtgtc aggggagcct ggaggcccag gagtaccaac     180
tggataaaga gggaagccca gagccctggg acagaaataa cccactggaa cccaagaaca     240
aggccagatt ctccatccca tccatgacac agcaccatgc agggagatac cgctgccact     300
```

-continued

| | |
|---|---|
| attacagctc tgcaggctgg tcagagccca gcgaccccct ggagctggtg atgacaggat | 360 |
| tctacaacaa acccaccctc tcagccctgc ccagccctgt ggtggcctca gggggaata | 420 |
| tgaccctccg atgtggctca cagaagggat atcaccattt tgttctgatg aaggaaggag | 480 |
| aacaccagct cccccggacc ctggactcac agcagctcca cagtgggggg ttccaggccc | 540 |
| tgttccctgt gggccccgtg accccagcc acaggtggag gttcacatgc tattactatt | 600 |
| atacaaacac cccctgggtg tggtcccacc ccagtgaccc cctggagatt ctgccctcag | 660 |
| gcgtgtctag gaagccctcc ctcctgaccc tgcagggccc tgtcctggcc cctgggcaga | 720 |
| gcctgacccct ccagtgtggc tctgatgtcg gctacgacac atttgttctg tataaggagg | 780 |
| gggaacgtga cttcctccag cgccctggcc agcagcccca ggctgggctc tccaggcca | 840 |
| acttcacccct gggccctgtg agccgctcct acggggggcca gtacaggtgc tatggtgcac | 900 |
| acaacctctc ctccgagtgg tcggccccca gcgaccccct gaacatcctg atggcaggac | 960 |
| agatctatga caccgtctcc ctgtcagcac agccgggccc cacagtggcc tcaggagaga | 1020 |
| acgtgaccct gctgtgtcag tcatggtggc agtttgacac tttccttctg accaaagaag | 1080 |
| gggcagccca tccccactg cgtctgagat caatgtacgg agctcataag taccaggctg | 1140 |
| aattccccat gagtcctgtg acctcagccc acgcgggac ctacaggtgc tacggctcac | 1200 |
| gcagctccaa ccccccacctg ctgtctcacc ccagtgagcc cctggagctc gtggtctcag | 1260 |
| gacactctgg aggctccagc ctcccaccca cagggccgcc ctccacacct ggtctgggaa | 1320 |
| gatacctgga ggttttgatt ggggtctcgg tggccttcgt cctgctgctc ttcctcctcc | 1380 |
| tcttcctcct cctccgacgt cagcgtcaca gcaaacacag gacatctgac cagagaaaga | 1440 |
| ctgatttcca gcgtcctgca ggggctgcgg agacagagcc caaggacagg ggcctgctga | 1500 |
| ggaggtccag cccagctgct gacgtccagg aagaaaacct ctatgctgcc gtgaaggaca | 1560 |
| cacagtctga ggacagggtg gagctggaca gtcagcagag cccacacgat gaagaccccc | 1620 |
| aggcagtgac gtatgccccg gtgaaacact ccagtcctag gagagaaatg gcctctcctc | 1680 |
| cctcctcact gtctggggaa ttcctggaca caaaggacag acaggtggaa gaggacaggc | 1740 |
| agatggacac tgaggctgct gcatctgaag cctcccagga tgtgacctac gcccagctgc | 1800 |
| acagcttgac ccttagacgg aaggcaactg agcctcctcc atcccaggaa ggggaacctc | 1860 |
| cagctgagcc cagcatctac gccactctgg ccatccacta gcccgggggg tacgcagacc | 1920 |
| ccacactcag cagaaggaga ctcaggactg ctgaaggcac gggagctgcc cccagtggac | 1980 |
| accagtgaac cccagtcagc ctggacccct aacacagacc atgaggagac gctgggaact | 2040 |
| tgtgggactc acctgactca aagatg | 2066 |

<210> SEQ ID NO 20
<211> LENGTH: 2232
<212> TYPE: DNA
<213> ORGANISM: Homo sapiens

<400> SEQUENCE: 20

| | |
|---|---|
| tctctctctg cttctttcct tttctctctc atggtagggt tatgagtcag ttgccaaaag | 60 |
| gtggggacat ttcctgatgc atttgcaaca ctgagaagtt atcttaaggg aggctgggcc | 120 |
| ccattctact catctggccc agaaagtgaa caccttgggg gccactaagg cagccctgct | 180 |
| aggggagacg ctccaacctg tcttctctct gtctcctggc agctctcttg gcctcctagt | 240 |
| ttctacctaa tcatgtccct ggtggaggcc atcagcctct ggaatgaagg ggtgctggca | 300 |
| gcggacaaga aggactggaa gggagccctg gatgccttca gtgccgtcca ggaccccac | 360 |

```
tcccggattt gcttcaacat tggctgcatg tacactatcc tgaagaacat gactgaagca      420
gagaaggcct ttaccagaag cattaaccga gacaagcact tggcagtggc ttacttccaa      480
cgagggatgc tctactacca gacagagaaa tatgatttgg ctatcaaaga ccttaaagaa      540
gccttgattc agcttcgagg gaaccagctg atagactata agatcctggg gctccagttc      600
aagctgtttg cctgtgaggt gttatataac attgctttca tgtatgccaa gaaggaggaa      660
tggaaaaaag ctgaagaaca gttagcattg gccacgagca tgaagtctga gcccagacat      720
tccaaaatcg acaaggcgat ggagtgtgtc tggaagcaga agctatatga gccagtggtg      780
atccctgtgg gcaggctgtt tcgaccaaat gagagacaag tggctcagct ggccaagaag      840
gattacctag gcaaggcaac ggtcgtggca tctgtggtgg atcaagacag tttctctggg      900
tttgccccct gcaaccaca ggcagctgag cctccaccca gaccgaaaac cccagagatc       960
ttcagggctc tggaagggga ggctcaccgt gtgctatttg ggtttgtgcc tgagacaaaa      1020
gaagagctcc aggtcatgcc agggaacatt gtctttgtct tgaagaaggg caatgataac      1080
tgggccacgg tcatgttcaa cgggcagaag gggcttgttc cctgcaacta ccttgaacca      1140
gttgagctgc ggatccaccc tcagcagcag ccccaggagg aaagctctcc gcagtccgac      1200
atcccagctc ctcctagttc caaagcccct ggaagacccc agctgtcacc aggccagaaa      1260
caaaaagaag agcctaagga agtgaagctc agtgttccca tgccctacac actcaaggtg      1320
cactacaagt acacggtagt catgaagact cagcccgggc tcccctacag ccaggtccgg      1380
gacatggtgt ctaagaaact ggagctccgg ctggaacaaa ctaagctgag ctatcggcct      1440
cgggacagca atgagctggt gccccttca gaagacagca tgaaggatgc ctggggccag       1500
gtgaaaaact actgcctgac tctgtggtgt gagaacacag tgggtgacca aggctttcca      1560
gatgaaccca aggaaagtga aaagctgat gctaataacc agacaacaga acctcagctt       1620
aagaaaggca gccaagtgga ggcactcttc agttatgagg ctacccaacc agaggacctg      1680
gagtttcagg aagggggatat aatcctggtg ttatcaaagg tgaatgaaga atggctggaa      1740
ggggagtgca aagggaaggt gggcattttc cccaaagttt ttgttgaaga ctgcgcaact      1800
acagatttgg aaagcactcg gagagaagtc taggatgttt cacaaactac aaagctgaag      1860
aaaatgaagc cctattactt gtttgtaaga tttagcaccc ttctgctgta tactgtactg      1920
agacattaca gtttggaagt gttaactatt tattccctgt taaaatttaa cctactagac      1980
aatgatgtga gtacccagga tgatttcctg gggcacagtg ggtgaggaga tggggacagg      2040
tgaatggagg agttagggga gaggaaaagt ggatggaagt gtctggaaag ggcacgagag      2100
agtcttccag gtactgatcc tgtttcttgc tctgagtgct agctagccag ctgtgttcac      2160
actgtaaaca ttcatcaagc tgtacatttg gtgcactttt ctgtgtcata ccacaaaaaa      2220
aaaaaaaaaa aa                                                          2232

<210> SEQ ID NO 21
<211> LENGTH: 4465
<212> TYPE: DNA
<213> ORGANISM: Homo sapiens

<400> SEQUENCE: 21
caattgtcat acgacttgca gtgagcgtca ggagcacgtc caggaactcc tcagcagcgc       60
ctccttcagc tccacagcca gacgccctca gacagcaaag cctaccccg cgccgcgccc       120 tgcccgccgc tcggatgctc gcccgcgccc tgctgctgtg cgcggtcctg cgctcagcc       180 atacagcaaa tccttgctgt tcccacccat gtcaaaaccg aggtgtatgt atgagtgtgg      240
```

-continued

| | |
|---|---|
| gatttgacca gtataagtgc gattgtaccc ggacaggatt ctatggagaa aactgctcaa | 300 |
| caccggaatt tttgacaaga ataaaattat ttctgaaacc cactccaaac acagtgcact | 360 |
| acatacttac ccacttcaag ggattttgga acgttgtgaa taacattccc ttccttcgaa | 420 |
| atgcaattat gagttatgtc ttgacatcca gatcacattt gattgacagt ccaccaactt | 480 |
| acaatgctga ctatggctac aaaagctggg aagccttctc taacctctcc tattatacta | 540 |
| gagcccttcc tcctgtgcct gatgattgcc cgactccctt gggtgtcaaa ggtaaaaagc | 600 |
| agcttcctga ttcaaatgag attgtggaaa aattgcttct aagaagaaag ttcatccctg | 660 |
| atccccaggg ctcaaacatg atgtttgcat tctttgccca gcacttcacg catcagtttt | 720 |
| tcaagacaga tcataagcga gggccagctt tcaccaacgg gctgggccat ggggtggact | 780 |
| taaatcatat ttacggtgaa actctggcta gacagcgtaa actgcgcctt ttcaaggatg | 840 |
| gaaaaatgaa atatcagata attgatggag agatgtatcc tcccacagtc aaagatactc | 900 |
| aggcagagat gatctaccct cctcaagtcc ctgagcatct acggtttgct gtggggcagg | 960 |
| aggtctttgg tctggtgcct ggtctgatga tgtatgccac aatctggctg cgggaacaca | 1020 |
| acagagtatg cgatgtgctt aaacaggagc atcctgaatg gggtgatgag cagttgttcc | 1080 |
| agacaagcag gctaatactg ataggagaga ctattaagat tgtgattgaa gattatgtgc | 1140 |
| aacacttgag tggctatcac ttcaaactga aatttgaccc agaactactt ttcaacaaac | 1200 |
| aattccagta ccaaaatcgt attgctgctg aatttaacac cctctatcac tggcatcccc | 1260 |
| ttctgcctga cacctttcaa attcatgacc agaaatacaa ctatcaacag tttatctaca | 1320 |
| acaactctat attgctggaa catggaatta cccagtttgt tgaatcattc accaggcaaa | 1380 |
| ttgctggcag ggttgctggt ggtaggaatg ttccacccgc agtacagaaa gtatcacagg | 1440 |
| cttccattga ccagagcagg cagatgaaat accagtcttt taatgagtac cgcaaacgct | 1500 |
| ttatgctgaa gccctatgaa tcatttgaag aacttacagg agaaaaggaa atgtctgcag | 1560 |
| agttggaagc actctatggt gacatcgatg ctgtggagct gtatcctgcc cttctggtag | 1620 |
| aaaagcctcg gccagatgcc atctttggtg aaaccatggt agaagttgga gcaccattct | 1680 |
| ccttgaaagg acttatgggt aatgttatat gttctcctgc ctactggaag ccaagcactt | 1740 |
| ttggtggaga agtgggtttt caaatcatca acactgcctc aattcagtct ctcatctgca | 1800 |
| ataacgtgaa gggctgtccc tttacttcat tcagtgttcc agatccagag ctcattaaaa | 1860 |
| cagtcaccat caatgcaagt tcttcccgct ccggactaga tgatatcaat cccacagtac | 1920 |
| tactaaaaga acgttcgact gaactgtaga agtctaatga tcatatttat ttatttatat | 1980 |
| gaaccatgtc tattaattta attatttaat aatatttata ttaaactcct tatgttactt | 2040 |
| aacatcttct gtaacagaag tcagtactcc tgttgcggag aaaggagtca tacttgtgaa | 2100 |
| gactttatg tcactactct aaagattttg ctgttgctgt taagtttgga aaacagtttt | 2160 |
| tattctgttt tataaaccag agagaaatga gttttgacgt cttttttactt gaatttcaac | 2220 |
| ttatattata agaacgaaag taaagatgtt tgaatactta aacactatca caagatggca | 2280 |
| aaatgctgaa agttttttaca ctgtcgatgt ttccaatgca tcttccatga tgcattagaa | 2340 |
| gtaactaatg tttgaaattt taaagtactt ttggttattt ttctgtcatc aaacaaaaac | 2400 |
| aggtatcagt gcattattaa atgaatattt aaattagaca ttaccagtaa tttcatgtct | 2460 |
| acttttaaaa atcagcaatg aaacaataat ttgaaatttc taaattcata gggtagaatc | 2520 |
| acctgtaaaa gcttgtttga tttcttaaag ttattaaact tgtacatata ccaaaaagaa | 2580 |
| gctgtcttgg atttaaatct gtaaaatcag atgaaatttt actacaattg cttgttaaaa | 2640 |

```
tattttataa gtgatgttcc tttttcacca agagtataaa ccttttagt gtgactgtta        2700
aaacttcctt ttaaatcaaa atgccaaatt tattaaggtg gtggagccac tgcagtgtta      2760
tctcaaaata agaatatttt gttgagatat tccagaattt gtttatatgg ctggtaacat      2820
gtaaaatcta tatcagcaaa agggtctacc tttaaaataa gcaataacaa agaagaaaac      2880
caaattattg ttcaaattta ggtttaaact tttgaagcaa acttttttt atccttgtgc       2940
actgcaggcc tggtactcag attttgctat gaggttaatg aagtaccaag ctgtgcttga      3000
ataacgatat gttttctcag attttctgtt gtacagttta atttagcagt ccatatcaca      3060
ttgcaaaagt agcaatgacc tcataaaata cctcttcaaa atgcttaaat tcatttcaca     3120
cattaatttt atctcagtct tgaagccaat tcagtaggtg cattggaatc aagcctggct      3180
acctgcatgc tgttcctttt cttttcttct tttagccatt ttgctaagag acacagtctt    3240
ctcatcactt cgtttctcct attttgtttt actagtttta agatcagagt tcactttctt    3300
tggactctgc ctatattttc ttacctgaac ttttgcaagt tttcaggtaa acctcagctc    3360
aggactgcta tttagctcct cttaagaaga ttaaaagaga aaaaaaaagg ccctttttaaa   3420
aatagtatac acttattta gtgaaaagc agagaatttt atttatagct aattttagct     3480
atctgtaacc aagatggatg caaagaggct agtgcctcag agagaactgt acggggtttg    3540
tgactggaaa aagttacgtt cccattctaa ttaatgccct ttcttattta aaaacaaaac    3600
caaatgatat ctaagtagtt ctcagcaata ataataatga cgataatact tcttttccac   3660
atctcattgt cactgacatt taatggtact gtatattact taatttattg aagattatta   3720
tttatgtctt attaggacac tatggttata aactgtgttt aagcctacaa tcattgattt    3780
tttttgtta tgtcacaatc agtatatttt cttgggggtt acctctctga atattatgta    3840
aacaatccaa agaaatgatt gtattaagat ttgtgaataa atttttagaa atctgattgg    3900
catattgaga tatttaaggt tgaatgtttg tccttaggat aggcctatgt gctagcccac   3960
aaagaatatt gtctcattag cctgaatgtg ccataagact gacctttttaa aatgttttga   4020
gggatctgtg gatgcttcgt taattttgttc agccacaatt tattgagaaa atattctgtg  4080
tcaagcactg tgggttttaa tatttttaaa tcaaacgctg attacagata atagtatttta  4140
tataaataat tgaaaaaaat tttctttttgg gaagagggag aaaatgaaat aaatatcatt    4200
aaagataact caggagaatc ttcttttacaa ttttacgttt agaatgttta aggttaagaa  4260
agaaatagtc aatatgcttg tataaaacac tgttcactgt tttttttaaaa aaaaaaactt  4320
gatttgttat taacattgat ctgctgacaa aacctgggaa tttgggttgt gtatgcgaat   4380
gtttcagtgc ctcagacaaa tgtgtattta acttatgtaa aagataagtc tggaaataaa   4440
tgtctgttta ttttttgtact attta                                         4465
```

<210> SEQ ID NO 22
<211> LENGTH: 442
<212> TYPE: DNA
<213> ORGANISM: Homo sapiens

<400> SEQUENCE: 22

```
caattttcac atcttccaca aactccattt agggagaaat gtttaaatct ctggtataag       60
tttactccat accagagtaa actatatatt actctatata agcagtcttg caataactaa      120
tcaccaccat agaagaaaga aacagactgc aaggaacaga gttgagtgtc tggagtcatc      180
aaaggcatta aaaactccag taaaagctgg ggccgtagca aaaatcatga aaacacttc       240
aacgtgtcct ttcaatcatc caattaaatg tgggtagatt aatgaaaatg tattcatcca    300
```

-continued

| | |
|---|---:|
| atattaactc atctatagca ctttgagtat ctttgtagtt catgatatcc tatcctataa | 360 |
| tgtggaggta aatgatttta tatgcattgg gggtcatata taaaacttca atgtaatttc | 420 |
| actacaataa attgccttcc tt | 442 |

<210> SEQ ID NO 23
<211> LENGTH: 3417
<212> TYPE: DNA
<213> ORGANISM: Homo sapiens

<400> SEQUENCE: 23

| | |
|---|---:|
| cggaggcagc gagaaagcgc agccaggcgg ctgctcggcg ttctctcagg tgactgctcg | 60 |
| gagttctccc agtgtttggt gttgcaagca ggatccaaag gagacctata gtgactccca | 120 |
| ggagctctta gtgaccaagt gaaggtacct gtggggctca ttgtgcccat tgctcttttca | 180 |
| ctgctttcaa ctggtagttg tgggttgaag cactggacaa tgccacatac tttgtggatg | 240 |
| gtgtgggtct tgggggtcat catcagcctc tccaaggaag aatcctccaa tcaggcttct | 300 |
| ctgtcttgtg accgcaatgg tatctgcaag ggcagctcag gatctttaaa ctccattccc | 360 |
| tcagggctca cagaagctgt aaaaagcctt gacctgtcca acaacaggat cacctacatt | 420 |
| agcaacagtg acctacagag gtgtgtgaac ctccaggctc tggtgctgac atccaatgga | 480 |
| attaacacaa tagaggaaga ttcttttttct tccctgggca gtcttgaaca tttagactta | 540 |
| tcctataatt acttatctaa tttatcgtct tcctggttca gccccttttc ttctttaaca | 600 |
| ttcttaaact tactgggaaa tccttacaaa accctagggg aaacatctct tttttctcat | 660 |
| ctcacaaaat tgcaaatcct gagagtggga aatatggaca ccttcactaa gattcaaaga | 720 |
| aaagattttg ctggacttac cttccttgag gaacttgaga ttgatgcttc agatctacag | 780 |
| agctatgagc caaaaagttt gaagtcaatt cagaatgtaa gtcatctgat ccttcatatg | 840 |
| aagcagcata ttttactgct ggagattttt gtagatgtta caagttccgt ggaatgtttg | 900 |
| gaactgcgag atactgattt ggacactttc cattttcag aactatccac tggtgaaaca | 960 |
| aattcattga ttaaaaagtt tacatttaga aatgtgaaaa tcaccgatga aagtttgttt | 1020 |
| caggttatga aacttttgaa tcagatttct ggattgttag aattagagtt tgatgactgt | 1080 |
| acccttaatg gagttggtaa ttttagagca tctgataatg acagagttat agatccaggt | 1140 |
| aaagtggaaa cgttaacaat ccggaggctg catattccaa ggttttactt atttatgat | 1200 |
| ctgagcactt tatattcact tacagaaaga gttaaaagaa tcacagtaga aaacagtaaa | 1260 |
| gttttttctgg ttccttgttt actttcacaa catttaaaat cattagaata cttggatctc | 1320 |
| agtgaaaatt tgatggttga agaatacttg aaaaattcag cctgtgagga tgcctggccc | 1380 |
| tctctacaaa cttttaatttt aaggcaaaat catttggcat cattgaaaaa accggagag | 1440 |
| actttgctca ctctgaaaaa cttgactaac attgatatca gtaagaatag ttttcattct | 1500 |
| atgcctgaaa cttgtcagtg gccagaaaag atgaaatatt tgaacttatc cagcacacga | 1560 |
| atacacagtg taacaggctg cattcccaag acactggaaa ttttagatgt tagcaacaac | 1620 |
| aatctcaatt tattttcttt gaatttgccg caactcaaag aactttatat ttccagaaat | 1680 |
| aagttgatga ctctaccaga tgcctccctc ttacccatgt tactagtatt gaaaatcagt | 1740 |
| aggaatgcaa taactacgtt ttctaaggag caacttgact catttcacac actgaagact | 1800 |
| ttggaagctg gtggcaataa cttcatttgc tcctgtgaat tcctctcctt cactcaggag | 1860 |
| cagcaagcac tggccaaagt cttgattgat tggccagcaa attacctgtg tgactctcca | 1920 |
| tcccatgtgc gtggccagca ggttcaggat gtccgcctct cggtgtcgga atgtcacagg | 1980 |

```
acagcactgg tgtctggcat gtgctgtgct ctgttcctgc tgatcctgct cacggggtc     2040 ctgtgccacc gtttccatgg cctgtggtat atgaaaatga tgtgggcctg gctccaggcc    2100
aaaaggaagc ccaggaaagc tcccagcagg aacatctgct atgatgcatt tgtttcttac    2160
agtgagcggg atgcctactg ggtggagaac cttatggtcc aggagctgga gaacttcaat    2220
ccccccttca agttgtgtct tcataagcgg gacttcattc ctggcaagtg gatcattgac    2280
aatatcattg actccattga aaagagccac aaaactgtct tgtgctttc tgaaaacttt     2340 gtgaagagtg agtggtgcaa gtatgaactg gacttctccc atttccgtct ttttgatgag    2400
aacaatgatg ctgccattct cattcttctg gagcccattg agaaaaaagc cattccccag    2460
cgcttctgca agctgcggaa gataatgaac accaagacct acctggagtg gcccatggac    2520
gaggctcagc gggaaggatt tgggtaaat ctgagagctg cgataaagtc ctaggttccc      2580
atatttaaga ccagtctttg tctagttggg atctttatgt cactagttat agttaagttc    2640
attcagacat aattatataa aaactacgtg gatgtaccgt catttgagga cttgcttact    2700
aaaactacaa aacttcaaat tttgtctggg gtgctgtttt ataaacatat gccagattta    2760
aaaattggtt tttggttttt cttttttcta tgagataacc atgatcataa gtctattact    2820
gatatctgaa tatagtccct tggtatccaa gggaattggt tgcaggatcc tcgtggatat    2880
caaaattcat agatgatcaa gtcccttata gagtggcat agtatttgca tataacctgt     2940
gtacattctc ctgtatactt taaatcatct ctagattact tatgataccc aatacaatgt    3000
aaatactatg taaatagttg tactgtcttt ttatttatat tattattgtt attttttatt    3060
ttcaaaattt ttaaaacata cttttgatcc acagttggtt gacttcatgg atgcagaacc    3120
catggatata gagggccaac tgtaatctgt agcaactggc ttagttcatt aggaaacagc    3180
acaaatgaac ttaagattct caatgactgt gtcattcttt cttcctgcta agagactcct    3240
ctgtggccac aaaaggcatt ctctgtccta cctagctgtc acttctctgt gcagctgatc    3300
tcaagagcaa caaggcaaag tatttggggc actccccaaa acttgttgct attcctagaa    3360
aaaagtgctg tgtatttcct attaaacttt acaggatgag aaaaaaaaaa aaaaaaa      3417
```

<210> SEQ ID NO 24
<211> LENGTH: 948
<212> TYPE: DNA
<213> ORGANISM: Homo sapiens

<400> SEQUENCE: 24

```
attgtggtgc cttgtagctg tcccgggagc cctcagcagc agttggagct ggtgcacagg      60
aaggatgagg aagaccaggc tctggggct gctgtggatg ctctttgtct cagaactccg      120
agctgcaact aaattaactg aggaaaagta tgaactgaaa gaggggcaga ccctggatgt     180
gaaatgtgac tacacgctag agaagtttgc cagcagccag aaagcttggc agataataag    240
ggacggagag atgcccaaga ccctggcatg cacagagagg ccttcaaaga attcccatcc    300
agtccaagtg gggaggatca tactagaaga ctaccatgat catggtttac tgcgcgtccg    360
aatggtcaac cttcaagtgg aagattctgg actgtatcag tgtgtgatct accagcctcc    420
caaggagcct cacatgctgt tcgatcgcat ccgcttggtg gtgaccaagg tttttcagg     480 gacccctggc tccaatgaga attctaccca gaatgtgtat aagattcctc ctaccaccac    540
taaggccttg tgcccactct ataccagccc cagaactgtg acccaagctc cacccaagtc    600
aactgccgat gtctccactc ctgactctga aatcaacctt acaaatgtga cagatatcat    660 caggggttccg gtgttcaaca ttgtcattct cctggctggt ggattcctga gtaagagcct    720
```

```
ggtcttctct gtcctgtttg ctgtcacgct gaggtcattt gtaccctagg cccacgaacc      780
cacgagaatg tcctctgact tccagccaca tccatctggc agttgtgcca agggaggagg      840
gaggaggtaa aaggcaggga gttaataaca tgaattaaat ctgtaatcac cagctatttc      900
taaagtcagc gtctcacctt aaaaaaaaaa aaaaaaaaa aaaaaaa                     948

<210> SEQ ID NO 25
<211> LENGTH: 383
<212> TYPE: DNA
<213> ORGANISM: Homo sapiens
<220> FEATURE:
<221> NAME/KEY: unsure
<222> LOCATION: (147)(154)(155)(159)(172)(228)
<223> OTHER INFORMATION: Wherein n can be a, c, t, or g

<400> SEQUENCE: 25
acctcagccc taacggtggt ggagaaccca aaggggagtt gctggaagcc atcaaacgtg       60
actttggttc ctttgacaag tttaaggaga agctgacggc tgcatctgtt ggtgtccaag      120
gctcaggttg gggttggctt ggtttcnaat aagnnaacng gggacactta cnaaattgct     180
gcttgtccaa atcaggatcc actgcaagga acaacaggcc ttattccnac tgctggggat     240
tgatgtgtgg gagcacgctt actaccttca gtataaaaat gtcaggcctg attatctaaa     300
agctatttgg aatgtaatca actgggagaa tgtaactgaa agatacatgg cttgcaaaaa     360
gtaaaccacg atcgttatgc tga                                             383

<210> SEQ ID NO 26
<211> LENGTH: 3834
<212> TYPE: DNA
<213> ORGANISM: Homo sapiens

<400> SEQUENCE: 26
cctgagacag aggcagcagt gatacccacc tgagagatcc tgtgtttgaa caactgcttc       60
ccaaaacgga aagtatttca agcctaaacc tttgggtgaa agaactcttt gaagtcatga      120
ttgcttcaca gtttctctca gctctcactt tggtgcttct cattaaagag agtggagcct      180
ggtcttacaa cacctccacg gaagctatga cttatgatga ggccagtgct tatttgtcagc     240 aaaggtacac acacctggtt gcaattcaaa acaaagaaga gattgagtac ctaaactcca     300
tattgagcta ttcaccaagt tattactgga ttggaatcag aaaagtcaac aatgtgtggg     360
tctgggtagg aacccagaaa cctctgacag aagaagccaa gaactgggct ccaggtgaac     420
ccaacaatag gcaaaaagat gaggactgcg tggagatcta catcaagaga gaaaaagatg     480
tgggcatgtg gaatgatgag aggtgcagca agaagaagct tgccctatgc tacacagctg     540
cctgtaccaa tacatcctgc agtggccacg gtgaatgtgt agagaccatc aataattaca     600
cttgcaagtg tgaccctggc ttcagtggac tcaagtgtga gcaaattgtg aactgtacag     660
ccctggaatc ccctgagcat ggaagcctgg tttgcagtca cccactggga aacttcagct     720
acaattcttc ctgctctatc agctgtgata ggggttacct gccaagcagc atggagacca     780
tgcagtgtat gtcctctgga gaatggagtg ctcctattcc agcctgcaat gtggttgagt     840
gtgatgctgt gacaaatcca gccaatgggt tcgtggaatg tttccaaaac cctggaagct     900
tcccatggaa cacaacctgt acatttgact gtgaagaagg atttgaacta atgggagccc     960
agagccttca gtgtacctca tctgggaatt gggacaacga gaagccaacg tgtaaagctg    1020
tgacatgcag ggccgtccgc cagcctcaga atggctctgt gaggtgcagc cattcccctg    1080
ctggagagtt caccttcaaa tcatcctgca acttcacctg tgaggaaggc ttcatgttgc    1140
```

```
agggaccagc ccaggttgaa tgcaccactc aagggcagtg gacacagcaa atcccagttt   1200
gtgaagcttt ccagtgcaca gccttgtcca accccgagcg aggctacatg aattgtcttc   1260
ctagtgcttc tggcagtttc cgttatgggt ccagctgtga gttctcctgt gagcagggtt   1320
ttgtgttgaa gggatccaaa aggctccaat gtggccccac aggggagtgg gacaacgaga   1380
agcccacatg tgaagctgtg agatgcgatg ctgtccacca gccccgaagg gtttggtga    1440 ggtgtgctca ttcccctatt ggagaattca cctacaagtc ctcttgtgcc ttcagctgtg   1500
aggagggatt tgaattatat ggatcaactc aacttgagtg cacatctcag ggacaatgga   1560
cagaagaggt tccttcctgc caagtggtaa aatgttcaag cctggcagtt ccgggaaaga   1620
tcaacatgag ctgcagtggg gagcccgtgt tggcactgt gtgcaagttc gcctgtcctg    1680
aaggatggac gctcaatggc tctgcagctc ggacatgtgg agccacagga cactggtctg   1740
gcctgctacc tacctgtgaa gctcccactg agtccaacat tcccttggta gctggacttt   1800
ctgctgctgg actctcccctc ctgacattag caccatttct cctctggctt cggaaatgct   1860
tacggaaagc aaagaaattt gttcctgcca gcagctgcca aagccttgaa tcagacggaa   1920
gctaccaaaa gccttcttac atcctttaag ttcaaaagaa tcagaaacag gtgcatctgg   1980
ggaactagag ggatacactg aagttaacag agacagataa ctctcctcgg gtctctggcc   2040
cttcttgcct actatgccag atgcctttat ggctgaaacc gcaacaccca tcaccacttc   2100
aatagatcaa agtccagcag gcaaggacgg ccttcaactg aaaagactca gtgttccctt   2160
tcctactctc aggatcaaga aagtgttggc taatgaaggg aaaggatatt ttcttccaag   2220
caaaggtgaa gagaccaaga ctctgaaatc tcagaattcc ttttctaact ctcccttgct   2280
cgctgtaaaa tcttggcaca gaaacacaat attttgtggc tttctttctt ttgcccttca   2340
cagtgtttcg acagctgatt acacagttgc tgtcataaga atgaataata attatccaga   2400
gtttagagga aaaaaatgac taaaaatatt ataacttaaa aaaatgacag atgttgaatg   2460
cccacaggca aatgcatgga gggttgttaa tggtgcaaat cctactgaat gctctgtgcg   2520
agggttacta tgcacaattt aatcactttc atccctatgg gattcagtgc ttcttaaaga   2580
gttcttaagg attgtgatat ttttacttgc attgaatata ttataatctt ccatacttct   2640
tcattcaata caagtgtggt agggacttaa aaaacttgta aatgctgtca actatgatat   2700
ggtaaaagtt acttattcta gattaccccc tcattgttta ttaacaaatt atgttacatc   2760 tgtttttaaat ttatttcaaa aagggaaact attgtcccct agcaaggcat gatgttaacc   2820
agaataaagt tctgagtgtt tttactacag ttgttttttg aaaacatggt agaattggag   2880
agtaaaaact gaatggaagg tttgtatatt gtcagatatt ttttcagaaa tatgtggttt   2940
ccacgatgaa aaacttccat gaggccaaac gttttgaact aataaaagca taaatgcaaa   3000
cacacaaagg tataatttta tgaatgtctt tgttggaaaa gaatacagaa agatggatgt   3060
gctttgcatt cctacaaaga tgtttgtcag atgtgatatg taaacataat tcttgtatat   3120
tatggaagat tttaaattca aatagaaac tcaccatgta aaagagtcat ctggtagatt    3180
tttaacgaat gaagatgtct aatagttatt ccctatttgt tttcttctgt atgttagggt   3240
gctctggaag agaggaatgc ctgtgtgagc aagcatttat gtttatttat aagcagattt   3300
aacaattcca aaggaatctc cagttttcag ttgatcactg gcaatgaaaa attctcagtc   3360
agtaattgcc aaagctgctc tagccttgag gagtgtgaga atcaaaactc tcctacactt   3420
ccattaactt agcatgtgtt gaaaaaaaaa gtttcagaga agttctggct gaacactggc   3480
aacgacaaag ccaacagtca aaacagagat gtgataagga tcagaacagc agaggttctt   3540
```

```
ttaaagggc   agaaaaactc   tgggaaataa   gagagaacaa   ctactgtgat   caggctatgt        3600
atggaataca   gtgttatttt   ctttgaaatt   gtttaagtgt   tgtaaatatt   tatgtaaact        3660
gcattagaaa   ttagctgtgt   gaaataccag   tgtggtttgt   gtttgagttt   tattgagaat        3720
tttaaattat   aacttaaaat   attttataat   ttttaaagta   tatatttatt   taagcttatg        3780
tcagacctat   ttgacataac   actataaagg   ttgacaataa   atgtgcttat   gttt              3834
```

<210> SEQ ID NO 27
<211> LENGTH: 2448
<212> TYPE: DNA
<213> ORGANISM: Homo sapiens

<400> SEQUENCE: 27

```
aaggggaggg   aaaaggggag   gaggaggagg   atgtgagact   gggttagaga   aatgaaagaa         60
agcaaggctt   tctgttgaca   ttcagtgcag   tctacctgca   gcacagcaca   ctccctttgg        120
gcaaggacct   gagacccttg   tgctaagtca   agaggctcaa   tgggctgcag   aagaactaga        180
gaaggaccaa   gcaaagccat   gatatttcca   tggaaatgtc   agagcaccca   gagggactta        240
tggaacatct   tcaagttgtg   ggggtggaca   atgctctgtt   gtgatttcct   ggcacatcat        300
ggaaccgact   gctggactta   ccattattct   gaaaaaccca   tgaactggca   aagggctaga        360
agattctgcc   gagacaatta   cacagattta   gttgccatac   aaaacaaggc   ggaaattgag        420
tatctggaga   agactctgcc   tttcagtcgt   tcttactact   ggataggaat   ccggaagata        480
ggaggaatat   ggacgtgggt   gggaaccaac   aaatctctta   ctgaagaagc   agagaactgg        540
ggagatggtg   agcccaacaa   caagaagaac   aaggaggact   gcgtggagat   ctatatcaag        600
agaaacaaag   atgcaggcaa   atggaacgat   gacgcctgcc   acaaactaaa   ggcagccctc        660
tgttacacag   cttcttgcca   gccctggtca   tgcagtggcc   atggagaatg   tgtagaaatc        720
atcaataatt   acacctgcaa   ctgtgatgtg   gggtactatg   gccccagtg    tcagtttgtg        780 attcagtgtg   agcctttgga   ggccccagag   ctgggtacca   tggactgtac   tcacccttg         840 ggaaacttca   gcttcagctc   acagtgtgcc   ttcagctgct   ctgaaggaac   aaacttaact        900
gggattgaag   aaaccacctg   tggaccattt   ggaaactggt   catctccaga   accaacctgt        960
caagtgattc   agtgtgagcc   tctatcagca   ccagatttgg   ggatcatgaa   ctgtagccat       1020
cccctggcca   gcttcagctt   tacctctgca   tgtaccttca   tctgctcaga   aggaactgag       1080
ttaattggga   agaagaaaac   catttgtgaa   tcatctggaa   tctggtcaaa   tcctagtcca       1140
atatgtcaaa   aattggacaa   aagtttctca   atgattaagg   agggtgatta   taacccctc        1200 ttcattccag   tggcagtcat   ggttactgca   ttctctgggt   tggcatttat   catttggctg       1260
gcaaggagat   taaaaaaagg   caagaaatcc   aagagaagta   tgaatgaccc   atattaaatc       1320
gcccttggtg   aaagaaaatt   cttggaatac   taaaaatcat   gagatccttt   aaatccttcc       1380
atgaaacgtt   ttgtgtggtg   gcacctccta   cgtcaaacat   gaagtgtgtt   tccttcagtg       1440
catctgggaa   gatttctacc   tgaccaacag   ttccttcagc   ttccatttcg   cccctcattt       1500
atccctcaac   cccagcccca   caggtgttta   tacagctcag   cttttttgtct   tttctgagga       1560 gaaacaaata   agaccataaa   gggaaaggat   tcatgtggaa   tataaagatg   gctgactttg       1620 ctcttcttg    actcttgttt   tcagtttcaa   ttcagtgctg   tacttgatga   cagacacttc       1680
taaatgaagt   gcaaatttga   tacatatgtg   aatatggact   cagttttctt   gcagatcaaa       1740
tttcacgtcg   tcttctgtat   actgtggagg   tacactctta   tagaaagttc   aaaaagtcta       1800
cgctctcctt   tctttctaac   tccagtgaag   taatggggtc   ctgctcaagt   tgaaagagtc       1860
```

```
ctatttgcac tgtagcctcg ccgtctgtga attggaccat cctatttaac tggcttcagc    1920
ctccccacct tcttcagcca cctctctttt tcagttggct gacttccaca cctagcatct    1980
catgagtgcc aagcaaaagg agagaagaga gaaatagcct gcgctgtttt ttagtttggg    2040
ggttttgctg tttccttttta tgagacccat tcctatttct tatagtcaat gtttcttta     2100 tcacgatatt attagtaaga aacatcact gaaatgctag ctgcaagtga catctctttg     2160
atgtcatatg gaagagttaa aacaggtgga gaaattcctt gattcacaat gaaatgctct    2220
cctttcccct gccccagac cttttatcca cttacctaga ttctacatat tctttaaatt    2280
tcatctcagg cctccctcaa ccccaccact tcttttataa ctagtccttt actaatccaa    2340
cccatgatga gctcctcttc ctggcttctt actgaaaggt taccctgtaa catgcaattt    2400
tgcatttgaa taaagcctgc ttttaagtg ttaaaaaaaa aaaaaaaa                 2448

<210> SEQ ID NO 28
<211> LENGTH: 291
<212> TYPE: DNA
<213> ORGANISM: Homo sapiens

<400> SEQUENCE: 28
ggtcttgggt tcctgtatgg tggaagctgg gtgagccaag acagggctg gctcctctgc       60 ccccgctgac gcttcccttg ccgttggctt tggatgtctt tgctgcagtc ttctctctgg     120
ctcaggtgtg ggtgggaggg gcccacagga agctcagcct tctcctccca aggtttgagt    180
ccctccaaag ggcagtgggt ggaggaccgg gagctttggg tgaccagcca ctcaaaggaa    240 cttctctggtc ccttcagtat cttcaaggtt tggaaactgc aaatgtcccc t             291

<210> SEQ ID NO 29
<211> LENGTH: 1670
<212> TYPE: DNA
<213> ORGANISM: Homo sapiens

<400> SEQUENCE: 29
attgagagtg gctctaacaa gtgccatttt tccttgttag cttttcatttc tcagcccttt      60 acaagattaa aatagtctgc agtttaatct ctccaaagct ttacggacag tgattctgtc    120
ctaaacaaga cagtgactcc aggatttctg aagactattg tggaagaagc atccattaag    180
gccaagctat aacatcagaa atggtgaatg aatacaagaa aattcttttg ctgaaaggat    240
ttgagctcat ggatgattat cattttacat caattaagtc cttactggcc tatgatttag    300
gactaactac aaaaatgcaa gaggaataca acagaattaa gattacagat ttgatggaaa    360
aaaagttcca aggcgttgcc tgtctagaca aactaataga acttgccaaa gatatgccat    420
cacttaaaaa ccttgttaac aatcttcgaa agagaagtc aaaagttgct aagaaaatta    480
aaacacaaga aaaagctcca gtgaaaaaaa taaaccagga agaagtgggt cttgcggcac    540
ctgcacccac cgcaagaaac aaactgacat cggaagcaag agggaggatt cctgtagctc    600
agaaaagaaa aactccaaac aaagaaaaga ctgaagccaa aaggaataag gtgtcccaag    660
agcagagtaa gccccaggt ccctcaggag ccagcacatc tgcagctgtg atcatcccc     720 cactacccca gacctcatca tcaactccat ccaacacttc gtttactccg aatcaggaaa    780
cccaggccca acggcaggtg gatgcaagaa gaaatgttcc ccaaaacgac ccagtgacag    840
tggtggtact gaaagcaaca gcgccatttta aatacgagtc cccagaaaat gggaaaagca    900
caatgtttca tgctacagtg gccagtaaga ctcaatattt ccatgtgaaa gtcttcgaca    960
tcaacttgaa agagaaattt gtaaggaaga aggtcattac catatctgat tactctgaat    1020
```

| | |
|---|---|
| gtaaaggagt aatggaaata aaggaagcat catctgtgtc tgactttaat caaaattttg | 1080 |
| aggtcccaaa cagaattatc gaaatagcaa ataaaactcc caagatcagt caactttaca | 1140 |
| agcaagcatc tggaacaatg gtgtatgggt tgtttatgtt acaaaagaaa agcgtacaca | 1200 |
| agaagaacac aatttatgaa atacaggata atacaggatc catggatgta gtggggagtg | 1260 |
| gaaaatggca caatatcaag tgtgagaaag gagataaact tcgactcttc tgccttcaac | 1320 |
| tgagaacagt tgaccgcaag ctgaaactgg tgtgtggaag tcacagcttc atcaaggtca | 1380 |
| tcaaggccaa gaaaacaag gaaggaccaa tgaatgttaa ttgaaatatg aaagctgaaa | 1440 |
| tgcaacaaac aacttccgct taaaacaatt aagttgttaa taactgtgat tttgtaaatt | 1500 |
| tcagtaattc atttaaatga tgtttcagta gatatattct agcatattaa gagcttttat | 1560 |
| aactgagtta tagattagtt tgcttctgg aataaaattt tcttcttata ctcttccttt | 1620 |
| tttttagata ttacattttg cttttatgac attcacgagg caaaaaaccg | 1670 |

<210> SEQ ID NO 30
<211> LENGTH: 355
<212> TYPE: DNA
<213> ORGANISM: Homo sapiens

<400> SEQUENCE: 30

| | |
|---|---|
| atggaatatc atcctgattt agaaaatttg gatgaagatg gatatactca attcacttc | 60 |
| gactctcaaa gcaataccag gatagctgtt gtttcagaga aagggattta tagtaaaaca | 120 |
| agtgtcttcc caacctgata attcatttg gataggcctt tctcggcccc agactgaggt | 180 |
| accatggctc tgggaggatg gatcaacatt ctcttctaac ttatttcaga tcagaaccac | 240 |
| agctacccaa gaaaacccat ctccaaattg tgtatggatt cacgtgtcag tcatttatga | 300 |
| ccaactgtgt agtgtgccct catatagtat ttgtgagaag aagttttcaa tgtaa | 355 |

<210> SEQ ID NO 31
<211> LENGTH: 1404
<212> TYPE: DNA
<213> ORGANISM: Homo sapiens

<400> SEQUENCE: 31

| | |
|---|---|
| ggcagtgcag ctgtgggaac ctctccacgc gcacgaactc agccaacgat ttctgataga | 60 |
| tttttgggag tttgaccaga gatgcaaggg gtgaaggagc gcttcctacc gttagggaac | 120 |
| tctggggaca gagcgccccg gccgcctgat ggccgaggca gggtgcgacc caggacccag | 180 |
| gacggcgtcg ggaaccatac catggcccgg atccccaaga ccctaaagtt cgtcgtcgtc | 240 |
| atcgtcgcgg tcctgctgcc agtcctagct tactctgcca ccactgcccg gcaggaggaa | 300 |
| gttccccagc agacagtggc cccacagcaa cagaggcaca gcttcaaggg ggaggagtgt | 360 |
| ccagcaggat ctcatagatc agaacatact ggagcctgta acccgtgcac agagggtgtg | 420 |
| gattacacca acgcttccaa caatgaacct tcttgcttcc catgtacagt ttgtaaatca | 480 |
| gatcaaaaac ataaaagttc ctgcaccatg accagagaca cagtgtgtca gtgtaaagaa | 540 |
| ggcaccttcc ggaatgaaaa ctcccccgag atgtgccgga gtgtagcag gtgccctagt | 600 |
| ggggaagtcc aagtcagtaa ttgtacgtcc tgggatgata ccagtgtgt tgaagaattt | 660 |
| ggtgccaatg ccactgtgga aaccccagct gctgaagaga caatgaacac cagcccgggg | 720 |
| actcctgccc cagctgctga agagacaatg aacaccagcc cagggactcc tgccccagct | 780 |
| gctgaagaga caatgaccac cagcccgggg actcctgccc cagctgctga agagacaatg | 840 |
| accaccagcc cggggactcc tgccccagct gctgaagaga caatgaccac cagcccgggg | 900 |

| | |
|---|---|
| actcctgcct cttctcatta cctctcatgc accatcgtag ggatcatagt tctaattgtg | 960 |
| cttctgattg tgtttgtttg aaagacttca ctgtggaaga aattccttcc ttacctgaaa | 1020 |
| ggttcaggta ggcgctggct gagggcgggg ggcgctggac actctctgcc ctgcctccct | 1080 |
| ctgctgtgtt cccacagaca gaaacgcctg cccctgcccc aagtcctggt gtctccagcc | 1140 |
| tggctctatc ttcctccttg tgatcgtccc atccccacat cccgtgcacc ccccaggacc | 1200 |
| ctggtctcat cagtccctct cctggagctg ggggtccaca catctcccag ccaagtccaa | 1260 |
| gagggcaggg ccagttcctc ccatcttcag gcccagccag gcaggggca gtcggctcct | 1320 |
| caactgggtg acaagggtga ggatgagaag tggtcacggg atttattcag ccttggtcag | 1380 |
| agcagaaaaa aaaaaaaaaa aaaa | 1404 |

<210> SEQ ID NO 32
<211> LENGTH: 885
<212> TYPE: DNA
<213> ORGANISM: Homo sapiens

<400> SEQUENCE: 32

| | |
|---|---|
| agcctacgca cgaaagtgac tagggaggaa ggatattata aagtgatgca aacagaaatt | 60 |
| ccaccagcct ccatgtatca tcatgtgtca taactcagtc aagctcagtg agcattctca | 120 |
| gcacattgcc tcaacagctt caaggtgagc cagctcaaga cttttgctctc caccaggcag | 180 |
| aagatgacag actgtgaatt tggatatatt tacaggctgg ctcaggacta tctgcagtgc | 240 |
| gtcctacaga taccaaacc tggatcaggt ccaagcaaaa cgtccagagt gctacaaaat | 300 |
| gttgcgttct cagtccaaaa agaagtggaa agaatctga agtcatgctt ggacaatgtt | 360 |
| aatgttgtgt ccgtagacac tgccagaaca ctattcaacc aagtgatgga aaaggagttt | 420 |
| gaagacggca tcattaactg gggaagaatt gtaaccatat ttgcatttga aggtattctc | 480 |
| atcaagaaac ttctacgaca gcaaattgcc ccggatgtgg ataccataa ggagatttca | 540 |
| tattttgttg cggagttcat aatgaataac acaggagaat ggataaggca aaacggaggc | 600 |
| tgggaaaatg gctttgtaaa gaagtttgaa cctaaatctg gctggatgac ttttctagaa | 660 |
| gttacaggaa agatctgtga aatgctatct ctcctgaagc aatactgttg accagaaagg | 720 |
| acactccata ttgtgaaacc ggcctaattt ttctgactga tatggaaacg attgccaaca | 780 |
| catacttcta cttttaaata aacaactttg atgatgtaac ttgaccttcc agagttatgg | 840 |
| aaattttgtc cccatgtaat gaataaattg tatgtatttt tctct | 885 |

<210> SEQ ID NO 33
<211> LENGTH: 569
<212> TYPE: DNA
<213> ORGANISM: Homo sapiens
<220> FEATURE:
<221> NAME/KEY: unsure
<222> LOCATION: (118)(120)(180)(395)(413)(416)(417)
<223> OTHER INFORMATION: Wherein n can be a, c, t, or g

<400> SEQUENCE: 33

| | |
|---|---|
| tggggcgcct atgatggaga ccctcagccc ctagggactc catcttttga ccttgaagtc | 60 |
| tcgctcaaac attcccctaa aagaacgggg gtgagggaga atggaaggca aaagagngn | 120 |
| aaaaagcaaa taacttcgg aatcggacaa cttaaagtct cgatatgagc ctcggattgn | 180 |
| attcgaactc ctgggttcta gacccagctc tgctactaac ttgtctgacc ttccccattt | 240 |
| ataaactgtt gtgggtgaga ggtgggacta ggtgaactct gagagccctg cactcggcgc | 300 |
| ggacgaggga tttaggggaa agtgtgctgt attccccgcg agccttcccc agcggccccg | 360 |

```
cctccccggg tgaatcccecg gcggccagcg cagcncaggc agcgatcctg gcngcnnccg      420
gggccggcag cttcctggaa agttacttct tgttggagcc ggcaataggc aaagtgtgtt      480
ctgtgaaatc cgcagagccg agattgacta cgttccggga atgagagggc tgtgtcattc      540
ccctcattgc ctgctgcatt gacggcgta                                        569

<210> SEQ ID NO 34
<211> LENGTH: 4654
<212> TYPE: DNA
<213> ORGANISM: Homo sapiens

<400> SEQUENCE: 34
gaattcctgc cactcttcct gcaacggccc aggagctcag agctccacat ctgaccttct       60
agtcatgacc aggaccaggg cagcactcct cctgttcaca gccttagcaa cttctctagg      120
tttcaacttg gacacagagg agctgacagc cttccgtgtg gacagcgctg ggtttggaga      180
cagcgtggtc cagtatgcca actcctgggt ggtggttgga gccccccaaa agataacagc      240
tgccaaccaa acgggtggcc tctaccagtg tggctacagc actggtgcct gtgagcccat      300
cggcctgcag gtgcccccgg aggccgtgaa catgtccctg gcctgtccc tggcgtctac       360 caccagccct tcccagctgc tggcctgcgg ccccaccgtg caccacgagt gcgggaggaa      420
catgtacctc accggactct gcttcctcct gggcccacc cagctcaccc agaggctccc       480
ggtgtccagg caggagtgcc aagacagga gcaggacatt gtgttcctga tcgatggctc      540
aggcagcatc tcctcccgca actttgccac gatgatgaac ttcgtgagag ctgtgataag      600
ccagttccag agacccagca cccagttttc cctgatgcag ttctccaaca attccaaac      660 acacttcact ttcgaggaat tcaggcgcac gtcaaacccc ctcagcctgt ggcttctgt      720 tcaccagctg caagggttta catacacggc caccgccatc caaaatgtcg tgcaccgatt      780
gttccatgcc tcatatgggg cccgtaggga tgccaccaaa attctcattg tcatcactga      840
tgggaagaaa aaggcgaca gcctggatta taaggatgtc atccccatgg ctgatgcagc      900
aggcatcatc cgctatgcaa ttggggttgg attagcttttt caaaacagaa attcttggaa      960
agaattaaat gacattgcat cgaagccctc ccaggaacac atatttaaag tggaggactt     1020
tgatgctctg aaagatattc aaaaccaact gaaggagaag atctttgcca ttgagggtac     1080
ggagaccaca agcagtagct ccttcgaatt ggagatggca caggagggct tcagcgctgt     1140
gttcacacct gatggccccg ttctggggc tgtggggagc ttcacctggt ctggaggtgc     1200
cttcctgtac ccccaaata tgagccctac cttcatcaac atgtctcagg agaatgtgga     1260
catgagggac tcttacctgg ttactccac cgagctggcc ctctggaaag gggtgcagag     1320
cctggtcctg ggggccccc gctaccagca caccggaag gctgtcatct tcacccaggt     1380
gtccaggcaa tggaggatga aggccgaagt cacggggact cagatcggct cctacttcgg     1440
ggcctccctc tgctccgtgg acgtagacac cgacggcagc accgacctgg tcctcatcgg     1500 ggcccccat tactacgagc agacccgagg gggccaggtg tctgtgtgtc ccttgcccag     1560
ggggtggaga aggtggtggt gtgatgctgt tctctacggg gagcagggcc acccctgggg     1620
tcgctttggg gcggctctga cagtgctggg ggatgtgaat gggacaagc tgacagacgt     1680 ggtcatcggg gccccaggag aggaggagaa ccggggtgct gtctacctgt ttcacggagt     1740
cttgggaccc agcatcagcc cctcccacag ccagcggatc gcgggctccc agctctcctc     1800
caggctgcag tattttgggc aggcactgag cgggggtcaa gacctcaccc aggatggact     1860
ggtggacctg gctgtggggg ccggggcca ggtgctcctg ctcaggacca gacctgtgct     1920
```

```
ctgggtgggg gtgagcatgc agttcatacc tgccgagatc cccaggtctg cgtttgagtg   1980 tcggagcag gtggtctctg agcagaccct ggtacagtcc aacatctgcc tttacattga   2040
caaacgttct aagaacctgc ttgggagccg tgacctccaa agctctgtga ccttggacct   2100
ggccctcgac cctggccgcc tgagtccccg tgccaccttc caggaaacaa agaaccggag   2160
tctgagccga gtccgagtcc tcgggctgaa ggcacactgt gaaaacttca acctgctgct   2220
cccgagctgc gtgaggact ctgtgacccc cattaccttg cgtctgaact tcacgctggt   2280
gggcaagccc ctccttgcct tcagaaacct gcggcctatg ctggccgcac tggctcagag   2340
atacttcacg gcctccctac cctttgagaa gaactgtgga gccgaccata tctgccagga   2400
caatctcggc atctccttca gcttcccagg cttgaagtcc ctgctggtgg ggagtaacct   2460
ggagctgaac gcagaagtga tggtgtggaa tgacggggaa gactcctacg aaccaccat   2520 caccttctcc caccccgcag gactgtccta ccgctacgtg gcagagggcc agaaacaagg   2580
gcagctgcgt tccctgcacc tgacatgtga cagcgcccca gttgggagcc agggcacctg   2640
gagcaccagc tgcagaatca accacctcat cttccgtggc ggcgcccaga tcaccttctt   2700
ggctaccttt gacgtctccc ccaaggctgt cctgggagac cggctgcttc tgacagccaa   2760
tgtgagcagt gagaacaaca ctcccaggac cagcaagacc accttccagc tggagctccc   2820
ggtgaagtat gctgtctaca ctgtggttag cagccacgaa caattcacca aatacctcaa   2880
cttctcagag tctgaggaga aggaaagcca tgtggccatg cacagatacc aggtcaataa   2940
cctgggacag agggacctgc ctgtcagcat caacttctgg gtgcctgtgg agctgaacca   3000
ggaggctgtg tggatggatg tggaggtctc ccaccccag aacccatccc ttcggtgctc   3060
ctcagagaaa atcgcacccc cagcatctga cttcctggcg cacattcaga gaatcccgt   3120 gctggactgc tccattgctg gctgcctgcg gttccgctgt gacgtcccct ccttcagcgt   3180
ccaggaggag ctggatttca ccctgaaggg caacctcagc tttggctggg tccgccagat   3240
attgcagaag aaggtgtcgg tcgtgagtgt ggctgaaatt acgttcgaca catccgtgta   3300
ctcccagctt ccaggacagg aggcatttat gagagctcag acgacaacgg tgctggagaa   3360
gtacaaggtc cacaacccca ccccctcat cgtaggcagc tccattgggg gtctgttgct   3420
gctggcactc atcacagcgg tactgtacaa agttggcttc ttcaagcgtc agtacaagga   3480
aatgatggag gaggcaaatg gacaaattgc cccagaaaac gggacacaga cccccagccc   3540
gcccagtgag aaatgatccc tctttgcctt ggacttcttc tcccgcgatt ttccccactt   3600
acttaccctc acctgtcagg ctgacgggga ggaaccactg caccaccgag agaggctggg   3660
atgggcctgc ttcctgtctt tgggagaaaa cgtcttgctt gggaagggc ctttgtcttg   3720 tcaaggttcc aactggaaac ccttaggaca gggtccctgc tgtgttcccc aaaaggactt   3780
gacttgcaat ttctacctag aaatacatgg acaataccc caggcctcag tctcccttct   3840
cccatgaggc acgaatgatc tttcttttcct ttccttttt tttttttct ttctttttt   3900 tttttttttg agacggagtc tcgctctgtc acccaggctg gagtgcaatg gcgtgatctc   3960
ggctcgctgc aacctccgcc tcccgggttc aagtaattct gctgtctcag cctcctgcgt   4020
agctgggact acaggcacac gccacctcgc ccggcccgat ctttctaaaa tacagttctg   4080
aatatgctgc tcatccccac ctgtcttcaa cagctcccca ttaccctcag acaatgtct   4140 gaactctcca gcttcgcgtg agaagtcccc ttccatccca gagggtgggc ttcagggcgc   4200
acagcatgag agcctctgtg cccccatcac cctcgtttcc agtgaattag tgtcatgtca   4260
gcatcagctc agggcttcat cgtggggctc tcagttccga ttccccaggc tgaattggga   4320
```

-continued

| | |
|---|---|
| gtgagatgcc tgcatgctgg gttctgcaca gctggcctcc cgcggttggg tcaacattgc | 4380 |
| tggcctggaa gggaggagcg ccctctaggg agggacatgg ccccggtgcg gctgcagctc | 4440 |
| accagcccca ggggcagaag agacccaacc acttcctatt ttttgaggct atgaatatag | 4500 |
| tacctgaaaa aatgccaagc actagattat ttttttaaaa agcgtacttt aaatgtttgt | 4560 |
| gttaatacac attaaaacat cgcacaaaaa cgatgcatct accgctcctt gggaaataat | 4620 |
| ctgaaaggtc taaaaataaa aaagccttct gtgg | 4654 |

<210> SEQ ID NO 35
<211> LENGTH: 1633
<212> TYPE: DNA
<213> ORGANISM: Homo sapiens

<400> SEQUENCE: 35

| | |
|---|---|
| tgctccctga cagccacaaa cctacagcac tgactgcatt cagagaggaa cctgcaaaca | 60 |
| aaacttcaca gaaaactttt tgttcttgtt ccagagaatt tgctgaagag gagaaggaaa | 120 |
| aaaaaaacac caaaaaaaaa aataaaaaaa tccacacaca caaaaaacct gcgcgtgagg | 180 |
| ggggaggaaa agcagggcct tttaaaaagg caatcacaac aacttttgct gccaggatgc | 240 |
| ccttgctttg gctgagagga tttctgttgg caagttgctg gattatagtg aggagttccc | 300 |
| ccaccccagg atccgagggg cacagcgcgg ccccgactg tccgtcctgt gcgctggccg | 360 |
| ccctcccaaa ggatgtaccc aactctcagc cagagatggt ggaggccgtc aagaagcaca | 420 |
| ttttaaacat gctgcacttg aagaagagac ccgatgtcac ccagccggta cccaaggcgg | 480 |
| cgcttctgaa cgcgatcaga aagcttcatg tgggcaaagt cggggagaac gggtatgtgg | 540 |
| agatagagga tgacattgga aggagggcag aaatgaatga acttatggag cagacctcgg | 600 |
| agatcatcac gtttgccgag tcaggaacag ccaggaagac gctgcacttc gagatttcca | 660 |
| aggaaggcag tgacctgtca gtggtggagc gtgcagaagt ctggctcttc ctaaaagtcc | 720 |
| ccaaggccaa caggaccagg accaaagtca ccatccgcct cttccagcag cagaagcacc | 780 |
| cgcagggcag cttggacaca ggggaagagg ccgaggaagt gggcttaaag ggggagagga | 840 |
| gtgaactgtt gctctctgaa aaagtagtag acgctcggaa gagcacctgg catgtcttcc | 900 |
| ctgtctccag cagcatccag cggttgctgg accagggcaa gagctccctg gacgttcgga | 960 |
| ttgcctgtga gcagtgccag gagagtggcg ccagcttggt tctcctgggc aagaagaaga | 1020 |
| agaaagaaga ggaggggaa gggaaaaaga agggcggagg tgaaggtggg gcaggagcag | 1080 |
| atgaggaaaa ggagcagtcg cacagaccctt tcctcatgct gcaggccgg cagtctgaag | 1140 |
| accaccctca tcgccggcgt cggcggggct tggagtgtga tggcaaggtc aacatctgct | 1200 |
| gtaagaaaca gttctttgtc agtttcaagg acatcggctg gaatgactgg atcattgctc | 1260 |
| cctctggcta tcatgccaac tactgcgagg gtgagtgccc gagccatata gcaggcacgt | 1320 |
| ccgggtcctc actgtccttc cactcaacag tcatcaacca ctaccgcatg cggggccata | 1380 |
| gccccttgc caacctcaaa tcgtgctgtg tgcccaccaa gctgagaccc atgtccatgt | 1440 |
| tgtactatga tgatggtcaa acatcatca aaaggacat tcagaacatg atcgtggagg | 1500 |
| agtgtgggtg ctcatagagt tgcccagccc aggggaaag ggagcaagag ttgtccagag | 1560 |
| aagacagtgg caaaatgaag aaattttaa ggtttctgag ttaaccagaa aaatagaaat | 1620 |
| taaaacaaa aca | 1633 |

<210> SEQ ID NO 36
<211> LENGTH: 879
<212> TYPE: DNA

<213> ORGANISM: Homo sapiens

<400> SEQUENCE: 36

```
gcggagtctc caactgggag agctgcagct gccgagagga ggagaacgct gaggtcggtc      60
ggaccaacgg acgcgctgac cgctgccaac tgcagctcgc gctgcctcct gctcgcgccg     120
tgccactaag gtcactcccg cctccgagag cccagagccg agatggaaac ggtccaggag     180
ctgatccccc tggccaagga gatgatggcc cagaagcgca aggggaagat ggtgaagctg     240
tacgtgctgg gcagcgtgct ggccctcttc ggcgtggtgc tcggcctgat ggagactgtg     300
tgcagcccct tcacggccgc cagacgtctg cgggaccagg aggcagccgt ggcggagctg     360
caggccgccc tggagcgaca ggctctccag aagcaagccc tgcaggagaa aggcaagcag     420
caggacacgg tcctcggcgg ccgggccctg tccaaccggc agcacgcctc ctaggaactg     480
tgggagacca gcggagtggg agggagacgc agtagacaga gacagaccga aaggaaggg     540
agagacagag ggggcgcgcg cacaggagcc tgactccgct gggagagtgc aggagcacgt     600
gctgtttttt atttggactt aacttcagag aaaccgctga catctagaac tgacctacca     660
caagcatcca ccaaaggagt ttgggattga gttttgctgc tgtgcagcac tgcattgtca     720
tgacatttcc aacactgtgt gaattatcta aatgcgtcta ccattttgca ctagggagga     780
aggataaatg cttttatgt tattattatt aattattaca atgaccacca ttttgcattt     840
tgaaataaaa aacttttat accaaaaaaa aaaaaaaaa                             879
```

<210> SEQ ID NO 37
<211> LENGTH: 556
<212> TYPE: DNA
<213> ORGANISM: Homo sapiens
<220> FEATURE:
<221> NAME/KEY: unsure
<222> LOCATION: (84)(85)(86)(87)(88)(89)(91)(92)(93)(94)(95)(97)(98)
      (99)(100)(101)(102)(103)(104)(105)(106)(107)(108)(109)(110)(112)
<223> OTHER INFORMATION: Wherein n can be a, c, t, or g

<400> SEQUENCE: 37

```
gaggttaatt gaattcctgg gttgaaaaac taacttgttt ttgttttcca aaattagctg      60
aaatcttgta aaccatgcct tccnnnnnna nnnnnnannn nnnnnnnnnn tnaaaatatg     120
gcaccataaa aaagtcatgt agtaatagag catatgcttt tttagaacca ggttaaaagc     180
tgtttgttat ctaatagagt aaaagttact gaggtcaaca gatagacagg tctggcataa     240
tatatgccca gtcataatag tctaattata ttcttttgac aacagacagc attcatcaga     300
gcactaattc gaatgagagt tttggctatc aagatgtgtt gattctaaat attattgaat     360
gagacctgat taaagtctga ctttcctggc cccagtgttt tgcaggttgg ctatttccat     420
tatcagccca tcactccata aagttcttag ctgcaccaag tgattggtga acaaggacaa     480
caacaaaagc agcatacatt gtatggattt atctcaacgc tattgtttaa tggctgtgtt     540
taatgtgatc tatctg                                                    556
```

<210> SEQ ID NO 38
<211> LENGTH: 996
<212> TYPE: DNA
<213> ORGANISM: Homo sapiens

<400> SEQUENCE: 38

```
tgcgccccac tcctgctcct cttgctgctg ccgccgctgc tgctcacgcc ccgcgctggg      60
gacgccgccg tgatcaccgg ggcttgtgac aaggactccc aatgtggtgg aggcatgtgc     120
tgtgctgtca gtatctgggt caagagcata aggatttgca cacctatggg caaactggga     180
```

```
gacagctgcc atccactgac tcgtaaaaac aattttggaa atggaaggca ggaaagaaga    240
aagaggaaga gaagcaaaag gaaaaggag gttccatttt ttgggcggag gatgcatcac    300
acttgcccat gtctgccagg cttggcctgt ttacggactt catttaaccg atttatttgt    360
ttagcccaaa agtaatcgct ctggagtaga aaccaaatgt gaatagccac atcttacctg    420
taaagtctta cttgtgattg tgccaaacaa aaaatgtgcc agaaagaaat gctcttgctt    480 cctcaactt  ccaagtaaca ttttatctt  tgatttgtaa atgattttt  ttttttttat    540 cgaaagagaa ttttacttt  ggatagaaat atgaagtgta aggcattatg gaactggttc    600
ttatttccct gttgtgttt  tggtttgatt tggcttttt  cttaaatgtc aaaaacgtac    660
ccatttcaca aaaatgaggg aaataagaat ttgatatttt gttagaaaaa ctttttttt     720 ttttctcac  caccccaagc cccatttgtg ccctgccgca caaatacacc tacagctttt    780
ggtcccttgc ctcttccacc tcaaagaatt tcaaggctct taccttactt tattttttgtc   840 catttctctt ccctcctctt gcattttaaa gtggagggtt tgtctctttg agtttgatgg    900
cagaatcact gatgggaatc cagcttttg  ctggcattta aatagtgaaa agagtgtata    960
tgtgaacttg acactccaaa ctcctgtcat ggcacg                              996

<210> SEQ ID NO 39
<211> LENGTH: 5855
<212> TYPE: DNA
<213> ORGANISM: Homo sapiens

<400> SEQUENCE: 39
agttgcctgc gcgccctcgc cggaccggcg gctccctagt tgcgccccga ccaggccctg     60
cccttgctgc cggctcgcgc gcgtccgcgc cccctccatt cctgggcgca tcccagctct    120
gccccaactc gggagtccag gcccgggcgc cagtgcccgc ttcagctccg gttcactgcg    180
cccgccggac gcgcgccgga ggactccgca gccctgctcc tgaccgtccc cccaggctta    240
acccggtcgc tccgctcgga ttcctcggct gcgctcgctc gggtggcgac ttcctccccg    300 cgcccctcc  ccctcgccat gaagaagtcc attggaatat taagcccagg agttgctttg    360
gggatggctg gaagtgcaat gtcttccaag ttcttcctag tggctttggc catattttc     420 tccttcgccc aggttgtaat tgaagccaat tcttggtggt cgctaggtat gaataaccct    480
gttcagatgt cagaagtata tattataggg gcacagcctc tctgcagcca actggcagga    540
ctttctcaag gacagaagaa actgtgccac ttgtatcagg accacatgca gtacatcgga    600
gaaggcgcga agacaggcat caaagaatgc cagtatcaat tccgacatcg aaggtggaac    660
tgcagcactg tggataacac ctctgttttt gcagggtga  tgcagatagg cagccgcgag    720
acggccttca catacgcggt gagcgcagca ggggtggtga acgccatgag ccgggcgtgc    780
cgcgagggcg agctgtccac ctgcggctgc agccgcgccg cgcgcccaa  ggacctgccg    840 cgggactggc tctgggcgg  ctgcggcgac aacatcgact atggctaccg ctttgccaag    900
gagttcgtgg acgcccgcga gcgggagcgc atccacgcca agggctccta cgagagtgct    960
cgcatcctca tgaacctgca caacaacgag gccggccgca ggacggtgta caacctggct   1020
gatgtggcct gcaagtgcca tggggtgtcc ggctcatgta gcctgaagac atgctggctg   1080
cagctggcag acttccgcaa ggtgggtgat gccctgaagg agaagtacga cagcgcggcg   1140
gccatgcggg tcaacagccc gggcaagttg gtacaggtca acagccgctt caactcgccc   1200
accacacaag acctggtcta catcgacccc agccctgact actgcgtgcg caatgagagc   1260
accggctcgc tgggcacgca gggccgcctg tgcaacaaga cgtcggaggg catggatggc   1320
```

```
tgcgagctca tgtgctgcgg ccgtggctac gaccagttca agaccgtgca gacggagcgc    1380
tgccactgca agttccactg gtgctgctac gtcaagtgca agaagtgcac ggagatcgtg    1440
gaccagtttg tgtgcaagta gtgggtgcca cccagcactc agccccgctc ccaggacccg    1500
cttatttata gaaagtacag tgattctggt ttttggtttt tagaaatatt ttttattttt    1560
ccccaagaat tgcaaccgga accattttt ttcctgttac catctaagaa ctctgtggtt    1620
tattattaat attataatta ttatttggca ataatggggg tgggaaccaa gaaaaatatt    1680
tattttgtgg atctttgaaa aggtaataca agacttcttt tgatagtata gaatgaaggg    1740
gaaataacac atacctaac ttagctgtgt ggacatggta cacatccaga aggtaaagaa    1800
atacattttc tttttctcaa atatgccatc atatgggatg ggtaggttcc agttgaaaga    1860
gggtggtaga atctattca caattcagct tctatgacca aaatgagttg taaattctct    1920
ggtgcaagat aaaaggtctt gggaaaacaa aacaaaacaa aacaaacctc ccttccccag    1980
cagggctgct agcttgcttt ctgcattttc aaaatgataa tttacaatgg aaggacaaga    2040
atgtcatatt ctcaaggaaa aaaggtatat cacatgtctc attctcctca aatattccat    2100
ttgcagacag accgtcatat tctaatagct catgaaattt gggcagcagg gaggaaagtc    2160
cccagaaatt aaaaaattta aaactcttat gtcaagatgt tgatttgaag ctgttataag    2220
aattaggatt ccagattgta aaaagatccc caaatgattc tggacactag attttttgt    2280 ttggggaggt tggcttgaac ataaatgaaa atatcctgtt attttcttag ggatacttgg    2340
ttagtaaatt ataatagtaa aataataca tgaatcccat tcacaggttc tcagcccaag    2400
caacaaggta attgcgtgcc attcagcact gcaccagagc agacaaccta tttgaggaaa    2460
aacagtgaaa tccaccttcc tcttcacact gagccctctc tgattcctcc gtgttgtgat    2520
gtgatgctgg ccacgtttcc aaacggcagc tccactgggt ccccttttggt tgtaggacag    2580 gaaatgaaac attaggagct ctgcttggaa aacagttcac tacttaggga ttttttgtttc    2640 ctaaaacttt tattttgagg agcagtagtt ttctatgttt taatgacaga acttggctaa    2700
tggaattcac agaggtgttg cagcgtatca ctgttatgat cctgtgttta gattatccac    2760
tcatgcttct cctattgtac tgcaggtgta ccttaaaact gttcccagtg tacttgaaca    2820
gttgcattta taagggggga aatgtggttt aatggtgcct gatatctcaa agtcttttgt    2880
acataacata tatatatata tacatatata taaatataaa tataaatata tctcattgca    2940
gccagtgatt tagatttaca gtttactctg gggttatttc tctgtctaga gcattgttgt    3000
ccttcactgc agtccagttg ggattattcc aaaagttttt tgagtcttga gcttgggctg    3060
tggccctgct gtgatcatac cttgagcacg acgaagcaac cttgtttctg aggaagcttg    3120
agttctgact cactgaaatg cgtgttgggt tgaagatatc ttttttcttt tctgcctcac    3180 cccttttgtct ccaacctcca tttctgttca ctttgtggag agggcattac ttgttcgtta    3240
tagacatgga cgttaagaga tattcaaaac tcagaagcat cagcaatgtt tctcttttct    3300
tagttcattc tgcagaatgg aaacccatgc ctattagaaa tgacagtact tattaattga    3360
gtccctaagg aatattcagc ccactacata gatagctttt ttttttttt ttttaataag    3420 gacacctctt tccaaacagt gccatcaaat atgttcttat ctcagactta cgttgtttta    3480
aaagtttgga aagatacaca tctttcatac cccccttagg caggttggct ttcatatcac    3540
ctcagccaac tgtggctctt aatttattgc ataatgatat tcacatcccc tcagttgcag    3600
tgaattgtga gcaaaagatc ttgaaagcaa aaagcactaa ttagtttaaa atgtcacttt    3660
tttggttttt attatacaaa aaccatgaag tactttttt atttgctaaa tcagattgtt    3720
```

```
ccttttagt gactcatgtt tatgaagaga gttgagttta acaatcctag cttttaaaag    3780
aaactattta atgtaaaata ttctacatgt cattcagata ttatgtatat cttctagcct    3840
ttattctgta cttttaatgt acatatttct gtcttgcgtg atttgtatat ttcactggtt    3900
taaaaaacaa acatcgaaag gcttatgcca aatggaagat agaatataaa ataaaacgtt    3960
acttgtatat tggtaagtgg tttcaattgt ccttcagata attcatgtgg agattttgg    4020 agaaaccatg acggatagtt taggatgact acatgtcaaa gtaataaaag agtggtgaat    4080
tttaccaaaa ccaagctatt tggaagcttc aaaaggtttc tatatgtaat ggaacaaaag    4140
gggaattctc ttttcctata tatgttcctt acaaaaaaaa aaaaaaaaga aatcaagcag    4200
atggcttaaa gctggttata ggattgctca cattctttta gcattatgca tgtaacttaa    4260
ttgttttaga gcgtgttgct gttgtaacat cccagagaag aatgaaaagg cacatgcttt    4320
tatccgtgac cagatttta gtccaaaaaa atgtattttt ttgtgtgttt accactgcaa    4380
ctattgcacc tctctatttg aatttactgt ggaccatgtg tggtgtctct atgccctttg    4440
aaagcagttt ttataaaaag aaagcccggg tctgcagaga atgaaaactg gttggaaact    4500
aaaggttcat tgtgttaagt gcaattaata caagttattg tgcttttcaa aaatgtacac    4560
ggaaatctgg acagtgctgc acagattgat acattagcct ttgcttttc tctttccgga    4620 taaccttgta acatattgaa acctttaag gatgccaaga atgcattatt ccacaaaaaa    4680
acagcagacc aacatataga gtgttttaaa tagcatttct gggcaaattc aaactcttgt    4740
ggttctagga ctcacatctg tttcagtttt tcctcagttg tatattgacc agtgttcttt    4800
attgcaaaaa catatacccg atttagcagt gtcagcgtat ttttcttct catcctggag    4860 cgtattcaag atcttcccaa tacaagaaaa ttaataaaaa atttatatat aggcagcagc    4920
aaaagagcca tgttcaaaat agtcattatg ggctcaaata gaaagaagac ttttaagttt    4980
taatccagtt tatctgttga gttctgtgag ctactgacct cctgagactg gcactgtgta    5040
agttttagtt gcctacccta gctcttttct cgtacaattt tgccaatacc aagtttcaat    5100 ttgttttac aaaacattat tcaagccact agaattatca aatatgacgc tatagcagag    5160
taaatactct gaataagaga ccggtactag ctaactccaa gagatcgtta gcagcatcag    5220
tccacaaaca cttagtggcc cacaatatat agagagatag aaaaggtagt tataacttga    5280
agcatgtatt taatgcaaat aggcacgaag gcacaggtct aaaatactac attgtcactg    5340
taagctatac ttttaaaata tttatttttt ttaaagtatt ttctagtctt ttctctctct    5400
gtggaatggt gaaagagaga tgccgtgttt tgaaagtaag atgatgaaat gaattttaa    5460 ttcaagaaac attcagaaac ataggaatta aaacttagag aaatgatcta atttccctgt    5520
tcacacaaac tttacacttt aatctgatga ttggatattt tattttagtg aaacatcatc    5580
ttgttagcta actttaaaaa atggatgtag aatgattaaa ggttggtatg attttttttt    5640
aatgtatcag tttgaaccta gaatattgaa ttaaaatgct gtctcagtat tttaaaagca    5700
aaaaaggaat ggaggaaaat tgcatcttag accattttta tatgcagtgt acaatttgct    5760
gggctagaaa tgagataaag attatttatt tttgttcata tcttgtactt ttctattaaa    5820
atcattttat gaaatccaaa aaaaaaaaaa aaaaa                              5855
```

<210> SEQ ID NO 40
<211> LENGTH: 1240
<212> TYPE: DNA
<213> ORGANISM: Homo sapiens

<400> SEQUENCE: 40

```
gagctcgcag cgcgcggccc ctgtcctccg gcccgagatg aatcctgcgg cagaagccga      60
gttcaacatc ctcctggcca ccgactccta caaggttact cactataaac aatatccacc     120
caacacaagc aaagtttatt cctactttga atgccgtgaa agaagacag aaaactccaa      180
attaaggaag gtgaaatatg aggaaacagt attttatggg ttgcagtaca ttcttaataa    240
gtacttaaaa ggtaaagtag taaccaaaga gaaaatccag gaagccaaag atgtctacaa    300
agaacatttc caagatgatg tctttaatga aagggatgg aactacattc ttgagaagta     360
tgatgggcat cttccaatag aaataaaagc tgttcctgag ggctttgtca ttcccagagg    420
aaatgttctc ttcacggtgg aaaacacaga tccagagtgt tactggctta caaattggat    480
tgagactatt cttgttcagt cctggtatcc aatcacagtg ccacaaatt ctagagagca     540
gaagaaaata ttggccaaat atttgttaga aacttctggt aacttagatg gtctggaata    600
caagttacat gattttggct acagaggagt ctcttcccaa gagactgctg cataggagc    660
atctgctcac ttggttaact tcaaaggaac agatacagta gcaggacttg ctctaattaa    720
aaaatattat ggaacgaaag atcctgttcc aggctattct gttccagcag cagaacacag    780
taccataaca gcttggggga agaccatga aaaagatgct tttgaacata ttgtaacaca     840
gttttcatca gtgcctgtat ctgtggtcag cgatagctat gacatttata atgcgtgtga    900
gaaaatatgg ggtgaagatc taagacattt aatagtatcg agaagtacac aggcaccact    960
aataatcaga cctgattctg gaaaccctct tgacactgtg ttaaaggttt tggagatttt   1020
aggtaagaag tttcctgtta ctgagaactc aaagggttac aagttgctgc caccttatct   1080
tagagttatt caaggggatg gagtagatat taatacctta caagaggtat gtgttttata   1140
ttaaaagttt caataaggca tttccttataa ttaagttttgt ttatgtttga taaagaacac   1200
aatataaata caaaaaaaaa aaaaaaaaa aaaaaaaaa                             1240

<210> SEQ ID NO 41
<211> LENGTH: 6771
<212> TYPE: DNA
<213> ORGANISM: Homo sapiens

<400> SEQUENCE: 41 gggggtctg ctctgtgcgg tgaagcttct cttcttggca cctgcctggc atcggaagag      60
ggcccttct ccctccctgg gcttttatgt ggacactgta atgcctcagt tttcttttctt    120
tctttttgtt tttgacacag ggtctcactc tatcacccaa gctggagtgc agtggcacca    180
tcttagctca ccgcagcctc aaactcccca gctcgggtga ttcttcctgc ctcagcctcc    240
tgagtagtag cagctgggac cacagacgtc tgccaccaag cccagctgca ccgccagttc   300
cggggagggc cctgggccag cggctgtccg ccccccctcc tttataaagt cctggcctcg    360
ggacagcccg cacagctgcc cagcctgcgc agacgggaca gccctgtccc actcactctt    420
tccctgctg ctcctgccgg cagctcagct ggaaccatgg gaggccgcgt ctttctcgtc    480
tttctcgcat tctgtgtctg gctgactctg ccgggagctg aaacccagga ctccaggggc    540
tgtgcccggt ggtgccctca ggactcctcg tgtgtcaatg ccaccgcctg tcgctgcaat    600
ccagggttca gctcttttttc tgagatcatc accacccccca tggagacttg tgacgacatc    660
aacgagtgtg caacactgtc gaaagtgtca tgcgaaaat tctcggactg ctggaacaca    720
gagggagct acgactgcgt gtgcagccca ggatatgagc tgtttctgg ggcaaaaaca    780
ttcaagaatg agagcgagaa cacgtgtcaa gatgtggacg aatgtcagca gaacccaagg    840
ctctgtaaaa gctacggcac ctgcgtcaac accctcggca gctacacgtg ccagtgcctg    900
```

```
cctggcttca agctcaaacc tgaggacccg aagctctgca cagatgtgaa tgaatgcacc     960
tccggacaaa acccatgcca cagctccacc cactgcctca caacgtggg cagctatcag    1020
tgccgctgcc gcccgggctg gcaaccgatt ccggggtccc ccaatggccc aaacaatacc    1080
gtctgtgaag atgtggacga gtgcagctcc gggcagcatc agtgtgacag ctccaccgtc    1140
tgcttcaaca ccgtgggttc atacagctgc cgctgccgcc caggctggaa gcccagacac    1200
ggaatcccga ataaccaaaa ggacactgtc tgtgaagata tgactttctc cacctggacc    1260
ccgccccctg gagtccacag ccagacgctt cccgattct tcgacaaagt ccaggacctg    1320
ggcagagact acaagccagg cttggccaat aacaccatcc agagcatctt acaggcgctg    1380
gatgagctgc tggaggcccc tgggacctg gagaccctgc ccgcttaca gcagcactgt    1440
gtggccagtc acctgctgga tggcctagag gatgtcctca gaggcctgag caagaacctt    1500
tccaatgggc tgttgaactt cagttatcct gcaggcacag aattgtccct ggaggtgcag    1560
aagcaagtag acaggagtgt caccttgaga cagaatcagg cagtgatgca gctcgactgg    1620
aatcaggcac agaaatctgg tgacccaggc ccttctgtgg tgggccttgt ctccattcca    1680
gggatgggca gttgctggc tgaggcccct ctggtcctgg aacctgagaa gcagatgctt    1740
ctgcatgaga cacaccaggg cttgctgcag gacggctccc ccatcctgct ctcagatgtg    1800
atctctgcct ttctgagcaa caacgacacc caaaacctca gctccccagt taccttcacc    1860
ttctcccacc gttcagtgat cccgagacag aaggtgctct gtgtcttctg ggagcatggc    1920
cagaatggat gtggtcactg gccaccaca ggctgcagca aataggcac cagagacacc    1980
agcaccatct gccgttgcac ccacctgagc agctttgccg tcctcatggc ccactacgat    2040
gtgcaggagg aggatcccgt gctgactgtc atcacctaca tggggctgag cgtctctctg    2100
ctgtgcctcc tcctggcggc cctcacttt ctcctgtgta aagccatcca gaacaccagc    2160
acctcactgc atctgcagct ctcgctctgc ctcttcctgg cccacctcct cttcctcgtg    2220
gcaattgatc aaaccggaca caaggtgctg tgctccatca tcgccggtac cttgcactat    2280
ctctacctgg ccaccttgac ctggatgctg ctggaggccc tgtacctctt cctcactgca    2340
cggaacctga cggtggtcaa ctactcaagc atcaacagat tcatgaagaa gctcatgttc    2400
cctgtgggct acgagagtccc agctgtgaca gtggccattt ctgcagcctc caggcctcac    2460
ctttatggaa caccttcccg ctgctggctc caaccagaaa agggatttat atggggcttc    2520
cttggacctg tctgcgccat cttctctgtg aatttagttc tctttctggt gactctctgg    2580
attttgaaaa acagactctc ctccctcaat agtgaagtgt ccaccctccg gaacacaagg    2640
atgctggcat ttaaagcgac agctcagctg ttcatcctgg gctgcacgtg gtgtctgggc    2700
atcttgcagg tgggtccggc tgcccgggtc atggcctacc tcttcaccat catcaacagc    2760
ctgcagggtg tcttcatctt cctggtgtac tgcctcctca gccagcaggt ccgggagcaa    2820
tatgggaaat ggtccaaagg gatcaggaaa ttgaaaactg agtctgagat gcacacactc    2880
tccagcagtg ctaaggctga cacctccaaa cccagcacgg ttaactagaa aaatcttctg    2940
aataagatct tccctctttg cccgtggaaa atctgaacaa tctttgagcc atctagaggg    3000
gaaagaaaag actttgttct gtgtgtttca agaaattcac catgtcagca atatgaagga    3060
tgttatggaa ggcgtgctag gcattcaatt cctgcagaaa ccggaaatct tccatgccct    3120
gcaatgtgct catcaaactc tcagcatatg acggccagc tgtggcccat atcttggtca    3180
ctctgaagca caatatttat gaagctatag aacgttaaga cctctttcac agcctctcct    3240
tcctacaaag actcctccaa atcttaaaat gaagcaggaa aacgagccta agaggacttt    3300
```

```
cataccgaca acatctgaaa ggactagaat gttcacacca cgatctggat ttcttaattt    3360 tttgttttg  tttttgttgt tctctagttc tacgggtttg attatttagt catgtgaaaa    3420
atattgatta ctcacacata gatcaagaga gacacggctc ctgccttcat ggagctttta    3480
ggggaaaatg aagtggctct tgcagctaga gttgactcag aagccgaaat tcctagaaat    3540
caggtttcta ctgctaggca attgaagtat aaactatttt ataaacactg tcttctttcg    3600
tcttcacacc aacatgcaga aaagtttcta atctcagatc ggggatgtgc aacaaattcc    3660
atttcaaagg aatgacctgc aaaactccta aatattccaa gcaaatgccc ttaaccctgt    3720
ctgttatctg cttcccttga acagaaattc tacatgacca taaaacctcg aagatgggta    3780
tggcacagtt catgccctgt aatcctagca ctttgggagg gtgaggcagg aggatggctc    3840
aagcccagga gtttgagacc agtgtgggca acagagtgag aaccatctct acccaaaaaa    3900
aaaattaaaa attagccaag catggtgatg atataggagt taaggagaaa tcatttaggc    3960
aaatagcaag ggtaggaagt cctcagtaag gttttccatt taatgaaaag cagcccccaa    4020
aatcattttc ttttctaaca aagaacagcc tgtaaaatcg agctgcagac atagacaagc    4080
aagctggaag cttccacggg tgaatgccgg cagctgtgcc aataggaaaa agctacctag    4140
actaggcatg tccaaaatgg cggctccaag ttcccttctc tttgccagcc atgtgtacag    4200
taaaaagcag gcaacatagt gtcagccaaa gctcatttgc ataataagat tagggtgggg    4260
tggccagctc atatagggt aggccctagg taaatcagac accgccttct caagcctgtc     4320
tataaaatct ggtacactat gacgagggtc agatttccca ttcagacgcc cctctcccat    4380
gcaagagaaa gagctgttct ccttctctt tcttttgcct attaaacctc tgctcctggc      4440
caggcacagt ggctcacgcc tataatccca gcactttggg aggctgaggt ggtcagatca    4500
cctaaggtca ggagttcaag accagcctgg tcaacatggt gaaatcttgt ctctagtaaa    4560
aatacaaaaa tatatgaaat ctcacataga tgataatatt aagttccaaa agcaactcaa    4620
cctggtagat tctaatttt  tttgaggcag ggtcttgctt tgtcacccat gctggagtac     4680
aatggcacaa acactgctca ctgcagcctc gacctcccaa ggcctaagca atcctcctgc    4740
ctcagtcccc ctccaggtat ttgaaactac aggtgtgtac caccacaccg gctaattttt    4800
tgtatttttt gtagagacgt gggtctcact atgctgccca ggctcaggtc ttaatctcct    4860
gagctcaggc aatccgcagg cctcagcctc cctaagtgcg gggattacag gcttgagcca    4920
ctgcacctag cctctatttg ttttacaaaa gagaaattga gatcctgaat gttaagtgac    4980
ttgcctgagg ccatcccact aacaggagcc agggttagga ttcaaacccc atccaactgg    5040
tcccagagct ggagcttctt gcactgcccct acactaccta ccatctccat cctctgggca    5100 ccttttata  agaaccaaaa cattacagag cattgctttg tcaactcagc tgggaacatt    5160
tcccagtgca actcacattt ttcactgctc tgtgcctgtc cgtataagct caatgagtat    5220
tgatttaggg gctttggaga actttgaatg ctaccccca agtaaccatt gttggcaacc     5280
tggtacctct acttttagcc atttctcctt ctctataaat agtgcagaag taacccactt    5340
ggtaacaggc atccttgcca agcctccacc actaggtcag tgtaagaatt aaagaaagag    5400
gaaagaaaca caaaaagtgg cttgatggtt aagacaggtt tattttagag aaaacacacc    5460
tgagaggggc tgctggctga attaggttag agtcttttct acagactaag agtgtttaag    5520
gatttagggt gggagagttt cttagaggct tggactgctt ctgtgttttt tttgttgtgc    5580
ttatatggga gggagagtgg tgtgtttgct tttatacatt tttctgcagc tgtaggcata    5640
ccccccaagt ctgcttttag cttccctatt ttagtgcacc tggagggaaa ggaatgtgct    5700
```

```
tattaaggcc cactgtttta ctggggccca ttgtatgagg gtgaagtttg gcagttaccc      5760
aagagacttt tcctccacct tcctctgtgc ccgagctgtt ttatctgcat tttactgtct      5820 gcttttttg gctgcttata gttttttaaaa aagtaatttc cttaaatcca gaaggctaaa      5880
aatgaagctg aaacttaaag tggcggtgtt tgtccaaaat aacggggctc ctgctctgcc      5940
agtcagtacc ctcaagtcac tcctgatcct caacctccat gcctaaggct ggttcaagag      6000
accacataat atctgccttt tattacatac atgatgggtg catgggattc tgcgtgccct      6060
ttgcttgata tagactgcta aggtgagatg gggaatatca gagtcagctg ctgcttgagg      6120
aagcagaaca cacagctgga ggcttggaac atgtgggtcc ctatgagtgt agagcccata      6180
tccccataga gtctacctag agcaggggtc gccaaatgtt ttcttaaaga gcctgatagt      6240
gtatatgtta ggctttgtga gccaggtatt tacagcaact caattctacc actgtggtat      6300
gaaaacagct atagacaatc ataaatgaat gatcatggct atgttttaat aaaacttttac     6360 agacactgaa cttgaacttc cattgtgata tgaaaacagc tatagacaat cataaatgaa      6420
tgatcatggc tatgttttaa taaaacttta tggacactga gcttgaactt catatatcag      6480
tcatgtgaca caaaatatca ttcttctttt tatttgtttt cacccatttg aaaaatgtaa      6540
aaactattct tagctgtaca gaaacagatg gtgggtcaga tttgactcac tgcccatagt      6600
ttccagacca tgatgttcag gttcatggaa gcacttcact ctacactaat ttattcatcc      6660
attcatcaca tatgtgatga gcacatacag acacacctca gagatattgc aggctccact      6720
ccagatcacc acaataatgt gaatattgca ataaagcaag tcatacacat t               6771

<210> SEQ ID NO 42
<211> LENGTH: 2051
<212> TYPE: DNA
<213> ORGANISM: Homo sapiens

<400> SEQUENCE: 42
cgccactttg ctggagcatt cactaggcga ggcgctccat cggactcact agccgcactc        60
atgaatcggc accatctgca ggatcacttt ctggaaatag acaagaagaa ctgctgtgtg       120
ttccgagatg acttcattgc caaggtgttg ccgccggtgt tggggctgga gtttatcttt       180
gggcttctgg gcaatggcct tgccctgtgg attttctgtt tccacctcaa gtcctggaaa       240
tccagccgga ttttcctgtt caacctggca gtagctgact ttctactgat catctgcctg       300
ccgttcgtga tggactacta tgtgcggcgt tcagactgga actttgggga catcccttgc       360
cggctggtgc tcttcatgtt tgccatgaac cgccagggca gcatcatctt cctcacggtg       420
gtggcggtag acaggtattt ccgggtggtc catccccacc acgccctgaa caagatctcc       480
aattggacag cagccatcat ctcttgcctt ctgtgggca tcactgttgg cctaacagtc        540
cacctcctga gaagaagtt gctgatccag aatggccctg caaatgtgtg catcagcttc        600
agcatctgcc ataccttccg gtggcacgaa gctatgttcc tcctggagtt cctcctgccc      660
ctgggcatca tcctgttctg ctcagccaga attatctgga gcctgcggca gagacaaatg      720
gaccggcatg ccaagatcaa gagagccatc accttcatca tggtggtggc catcgtcttt      780
gtcatctgct tccttcccag cgtggttgtg cggatccgca tcttctggct cctgcacact      840
tcgggcacgc agaattgtga agtgtaccgc tcggtggacc tggcgttctt tatcactctc      900
agcttccacc tacatgaacag catgctggac ccgtggtgt actacttctc cagcccatcc      960
tttcccaact tcttctccac tttgatcaac cgctgcctcc agaggaagat gacaggtgag     1020
ccagataata accgcagcac gagcgtcgag ctcacagggg accccaacaa aaccagaggc     1080
```

```
gctccagagg cgttaatggc caactccggt gagccatgga gcccctctta tctgggccca   1140
acctcaaata accattccaa gaagggacat tgtcaccaag aaccagcatc tctggagaaa   1200
cagttgggct gttgcatcga gtaatgtcac tggactcggc ctaaggtttc ctggaacttc   1260
cagattcaga gaatctgatt tagggaaact gtggcagatg agtgggagac tggttgcaag   1320
gtgtgaccac aggaatcctg gaggaacaga gagtaaagct tctaggcatc tgaaacttgc   1380
ttcatctctg acgctcgcag gactgaagat gggcaaattg taggcgtttc tgctgagcag   1440
agttggagcc agatctctac ttgtgacttg ttggccttct tcccacatct gcctcagact   1500 gggggggggct cagctcctcg ggtgatatct agcctgcttg tgagctctag cagggataag   1560
gagagctgag attggaggga attgtgttgc tcctggagga agcccaggca tcattaaaca   1620
agccagtagg tcacctggct tccgtggacc aattcatctt tcagacaagc tttagagaaa   1680
tggactcagg gaagagactc acatgctttg gttagtatct gtgtttccgg tgggtgtaat   1740
aggggattag cccccagaagg gactgagcta acagtgtta ttatgggaaa ggaaatggca   1800
ttgctgcttt caaccagcga ctaatgcaat ccattcctct cttgtttata gtaatctaag   1860
ggttgagcag ttaaaacggc ttcaggatag aaagctgttt cccacctgtt tcgttttacc   1920
attaaaaggg aaacgtgcct ctgccccacg ggtagagggg gtgcacgttc ctcctggttc   1980
cttcgcttgt gtttctgtac ttaccaaaaa tctaccactt caataaattt tgataggaga   2040
caaaaaaaaa a                                                       2051

<210> SEQ ID NO 43
<211> LENGTH: 1334
<212> TYPE: DNA
<213> ORGANISM: Homo sapiens

<400> SEQUENCE: 43
aatcattaga gcctgagtca ctctccccag gagacccaga cctagaacta cccagagcaa     60
gaccacagct ggtgaacagt ccaggagcag acaagatgga gacaaattcc tctctcccca    120
cgaacatctc tggagggaca cctgctgtat ctgctggcta tctcttcctg gatatcatca    180
cttatctggt atttgcagtc acctttgtcc tcggggtcct gggcaacggg cttgtgatct    240
gggtggctgg attccggatg acacacacag tcaccaccat cagttacctg aacctggccg    300
tggctgactt ctgtttcacc tccactttgc cattcttcat ggtcaggaag gccatgggag    360
gacattggcc tttcggctgg ttcctgtgca aattcgtctt taccatagtg gacatcaact    420
tgttcggaag tgtcttcctg atcgccctca ttgctctgga ccgctgtgtt tgcgtcctgc    480
atccagtctg gacccagaac caccgcaccg tgagcctggc caagaaggtg atcattgggc    540
cctgggtgat ggctctgctc ctcacattgc cagttatcat tcgtgtgact acagtacctg    600
gtaaaacggg gacagtagcc tgcactttta acttttcgcc ctggaccaac gaccctaaag    660
agaggataaa tgtggccgtt gccatgttga cggtgagagg catcatccgg ttcatcattg    720
gcttcagcgc acccatgtcc atcgttgctc tcagttatgg gcttattgcc accaagatcc    780
acaagcaagg cttgattaag tccagtcgtc ccttacgggt cctctccttt gtcgcagcag    840
ccttttttct ctgctggtcc ccatatcagg tggtggccct tatagccaca gtcagaatcc    900
gtgagttatt gcaaggcatg tacaaagaaa ttggtattgc agtggatgtg acaagtgccc    960
tggccttctt caacagctgc ctcaacccca tgctctatgt cttcatgggc caggacttcc   1020
gggagaggct gatccacgcc cttccgccaa gtctggagag ggccctgacc gaggactcaa   1080
cccaaaccag tgacacagct accaattcta ctttaccttc tgcagaggtg gagttacagg   1140
```

| | |
|---|---:|
| caaagtgagg agggagctgg gggacacttt cgagctccca gctccagctt cgtctcacct | 1200 |
| tgagttaggc tgagccacag gcatttcctg cttattttag gattacccac tcatcagaaa | 1260 |
| aaaaaaaaaa agcctttgtg tcccctgatt tggggagaat aaacagatat gagtttaaaa | 1320 |
| aaaaaaaaaa aaaa | 1334 |

<210> SEQ ID NO 44
<211> LENGTH: 993
<212> TYPE: DNA
<213> ORGANISM: Homo sapiens

<400> SEQUENCE: 44

| | |
|---|---:|
| atgctgccgg actggaagag ctccttgatc ctcatggctt acatcatcat cttcctcact | 60 |
| ggcctccctg ccaacctcct ggccctgcgg gcctttgtgg ggcggatccg ccagcccag | 120 |
| cctgcacctg tgcacatcct cctgctgagc ctgacgctgg ccgacctcct cctgctgctg | 180 |
| ctgctgccct tcaagatcat cgaggctgcg tcgaacttcc gctggtacct gcccaaggtc | 240 |
| gtctgcgccc tcacgagttt tggcttctac agcagcatct actgcagcac gtggctcctg | 300 |
| gcgggcatca gcatcgagcg ctacctggga gtggcttttcc ccgtgcagta caagctctcc | 360 |
| cgccggcctc tgtatggagt gattgcagct ctggtggcct gggttatgtc ctttggtcac | 420 |
| tgcaccatcg tgatcatcgt tcaatacttg aacacgactg agcaggtcag aagtggcaat | 480 |
| gaaattacct gctacgagaa cttcaccgat aaccagttgg acgtggtgct gcccgtgcgg | 540 |
| ctggagctgt gcctggtgct cttcttcatc cccatggcag tcaccatctt ctgctactgg | 600 |
| cgttttgtgt ggatcatgct ctcccagccc cttgtgggg cccagaggcg cgccgagcc | 660 |
| gtggggctgg ctgtggtgac gctgctcaat tcctggtgt gcttcggacc ttacaacgtg | 720 |
| tcccacctgg tggggtatca ccagagaaaa agccctggt ggcggtcaat agccgtggtg | 780 |
| ttcagttcac tcaacgccag tctggacccc tgctcttct atttctcttc ttcagtggtg | 840 |
| cgcagggcat ttgggagagg gctgcaggtg ctgcggaatc agggctcctc cctgttggga | 900 |
| cgcagaggca agacacagc agaggggaca aatgaggaca ggggtgtggg tcaaggagaa | 960 |
| gggatgccaa gttcggactt cactacagag tag | 993 |

<210> SEQ ID NO 45
<211> LENGTH: 2681
<212> TYPE: DNA
<213> ORGANISM: Homo sapiens

<400> SEQUENCE: 45

| | |
|---|---:|
| gcagggtggg ggcaggccag ctcagcagag cctggggcca gagggccaga cagccacaga | 60 |
| gctcctggcg tgggcaaggc tggccaagga tggcgacgcc caggggcctg ggggccctgc | 120 |
| tcctgctcct cctgctcccg acctcaggtc aggaaaagcc caccgaaggg ccaagaaaca | 180 |
| cctgcctggg gagcaacaac atgtacgaca tcttcaactt gaatgacaag gctttgtgct | 240 |
| tcaccaagtg caggcagtcg ggcagcgact cctgcaatgt ggaaaacttg cagagatact | 300 |
| ggctaaaacta cgaggcccat ctgatgaagg aaggtttgac gcagaaggtg aacacgcctt | 360 |
| tcctgaaggc tttggtccag aacctcagcc caacactgc agaagacttc tatttctctc | 420 |
| tggagccctc tcaggttccg aggcaggtga tgaaggacga ggacaagccc cctgacagag | 480 |
| tgcgacttcc caagagcctt tttcgatccc tgccaggcaa caggtctgtg gtccgcttgg | 540 |
| ccgtcaccat tctggacatt ggtccaggga ctctcttcaa gggcccccgg ctcggcctgg | 600 |
| gagatggcag cggcgtgttg aacaatcgcc tggtgggttt gagtgtggga caaatgcatg | 660 |

```
tcaccaagct ggctgagcct ctggagatcg tcttctctca ccagcgaccg ccccctaaca      720
tgaccctcac ctgtgtattc tgggatgtga ctaaagggac cactggagac tggtcttctg      780
agggctgctc cacggaggtc agacctgagg ggaccgtgtg ctgctgtgac cacctgacct      840
ttttcgccct gctcctgaga cccaccttgg accagtccac ggtgcatatc ctcacacgca      900
tctcccaggc gggctgtggg gtctccatga tcttcctggc cttcaccatt attctttatg      960
cctttctgag gctttcccgg gagaggttca agtcagaaga tgccccaaag atccacgtgg     1020
ccctgggtgg cagcctgttc ctcctgaatc tggccttctt ggtcaatgtg gggagtggct     1080
caaaggggtc tgatgctgcc tgctgggccc gggggctgt cttccactac ttcctgctct     1140
gtgccttcac ctggatgggc cttgaagcct ccacctcta cctgctcgct gtcagggtct     1200
tcaacaccta cttcgggcac tacttcctga agctgagcct ggtgggctgg ggcctgcccg     1260
ccctgatggt catcggcact gggagtgcca acagctacgg cctctacacc atccgtgata     1320
gggagaaccg cacctctctg gagctatgct ggttccgtga agggacaacc atgtacgccc     1380
tctatatcac cgtccacggc tacttcctca tcaccttcct cttttggcatg tggtcctgg     1440 ccctggtggt ctggaagatc ttcacccctgt cccgtgctac agtggtcaag gagcggggga     1500
agaaccggaa gaaggtgctc accctgctgg gcctctcgag cctggtgggt gtgacatggg     1560
ggttggccat cttcacccccg ttgggcctct ccaccgtcta catctttgca cttttcaact     1620
ccttgcaagg tgtcttcatc tgctgctggt tcaccatcct ttacctccca agtcagagca     1680
ccacagtctc ctcctctact gcaagattgg accaggccca ctccgcatct caagaatagg     1740
aaggcacggc cctgcaatat ggactcagct ctggctctct gtgtgacctt gggcagctcc     1800
gtgcctctct ctgtactccc tcagtttcct tctctgtaca atgtggctgg ggagggagag     1860
gatgggacca ggttggacca cgtggcatca gaggtcccat ccagatccaa ctataggtcc     1920
aagagtccac gtaagcaggt ttgcaaggct ctaaagttcc tatagtcctg agacccctg     1980 ccagcaaaga gtgacagtca cctccatgcc ctgccctcat tgcaaagccc tcactcacct     2040
tctggtctca gcaagggagg agagtctgtt gctggcatag ccctggaagg agcccccagc     2100
ctctcccctc ctcctccttg tcactggcct cccacaactc cccttctggc tgcctgtaac     2160
cttgaggggc attcaggagg ccagcgttcc ctcaggcact gggggtttgt tttgggggt     2220 gggagttgat cctcccaccc agtctgcccc tggtctctgc ccatccaatc agagcccacc     2280
ctcctggaag agaccccgt gttcagagtg ctggcagccc tgcacgtgtc cagggacact     2340
gcatttcaaa gaaccactga gtgggtgagc taccttgggc aaaccccca ctcctgactc     2400 tgactgccac gtgggtggcc cgacctctga cctgctgtca tcatagaggt agaaagcaaa     2460
caatctgggg ctcagcacac ctgggggtgc tcccactcat tcagtgtgtg gggcccctga     2520
gcagaggctg gcattgcca ctagaacctg agctcctaga gagcaaggac ctgggtggcc     2580
tcgcttactg ttccagccca ggccaagcac agggcctggc tcgtggcaaa ccttgaataa     2640
atatttgttg gctgaaaaaa aaaaaaaaaa aaaaaaaaaa a                         2681

<210> SEQ ID NO 46
<211> LENGTH: 3186
<212> TYPE: DNA
<213> ORGANISM: Homo sapiens

<400> SEQUENCE: 46
gcggccgcgg cggtgcagca gaggcgcctc gggcaggagg agggcggctt ctgcgagggc       60
agcctgaggt attaaaaagt gtcagcaaac tgcattgaat aacagacatc ctaagagggg      120
```

```
atatttttcca cctctataat gaagaaaagc aggagtgtga tgacggtgat ggctgatgat    180
aatgttaaag attattttga atgtagcttg agtaaatcct acagttcttc cagtaacaca    240
cttgggatcg acctctggag agggagaagg tgttgctcag gaaacttaca gttaccacca    300
ctgtctcaaa gacagagtga aagggcaagg actcctgagg gagatggtat ttccaggccg    360
accacactgc cttttgacaac gcttccaagc attgctatta caactgtaag ccaggagtgc    420
tttgatgtgg aaaatggccc ttccccaggt cggagtccac tggatcccca ggccagctct    480
tccgctgggc tggtacttca cgccacctt cctgggcaca gccagcgcag agagtcattt    540
ctctacagat cagacagcga ctatgacttg tcaccaaagg cgatgtcgag aaactcttct    600
cttccaagcg agcaacacgg cgatgacttg attgtaactc cttttgccca ggtccttgcc    660
agcttgcgaa gtgtgagaaa caacttcact atactgacaa accttcatgg tacatctaac    720
aagaggtccc cagctgctag tcagcctcct gtctccagag tcaacccaca agaagaatct    780
tatcaaaaat tagcaatgga aacgctggag gaattagact ggtgtttaga ccagctagag    840
accatacaga cctaccggtc tgtcagtgag atggcttcta acaagttcaa aagaatgctg    900
aaccgggagc tgacacacct ctcagagatg agccgatcag ggaaccaggt gtctgaatac    960
atttcaaata ctttcttaga caagcagaat gatgtggaga tcccatctcc tacccagaaa   1020
gacagggaga aaaagaaaaa gcagcagctc atgacccaga taagtggagt gaagaaatta   1080
atgcatagtt caagcctaaa caatacaagc atctcacgct ttggagtcaa cactgaaaat   1140
gaagatcacc tggccaagga gctggaagac ctgaacaaat ggggtcttaa catctttaat   1200
gtggctggat attctcacaa tagaccccta acatgcatca tgtatgctat attccaggaa   1260
agagacctcc taaagacatt cagaatctca tctgacacat ttataaccta catgatgact   1320
ttagaagacc attaccattc tgacgtggca tatcacaaca gcctgcacgc tgctgatgta   1380
gcccagtcga cccatgttct cctttctaca ccagcattag acgctgtctt cacagatttg   1440
gagatcctgg ctgccatttt tgcagctgcc atccatgacg ttgatcatcc tggagtctcc   1500
aatcagtttc tcatcaacac aaattcagaa cttgctttga tgtataatga tgaatctgtg   1560
ttggaaaatc atcaccttgc tgtgggtttc aaactgctgc aagaagaaca ctgtgacatc   1620
ttcatgaatc tcaccaagaa gcagcgtcag acactcagga agatggttat tgacatggtg   1680
ttagcaactg atatgtctaa acatatgagc ctgctggcag acctgaagac aatggtagaa   1740
acgaagaaag ttacaagttc aggcgttctt ctcctagaca actataccga tcgcattcag   1800
gtccttcgca acatggtaca ctgtgcagac ctgagcaacc ccaccaagtc cttggaattg   1860
tatcggcaat ggacagaccg catcatggag gaatttttcc agcagggaga caaagagcgg   1920 gagagggaa tggaaattag cccaatgtgt gataaacaca cagcttctgt ggaaaaatcc   1980
caggttggtt tcatcgacta cattgtccat ccattgtggg agacatgggc agatttggta   2040
cagcctgatg ctcaggacat tctcgatacc ttagaagata caggaactg gtatcagagc   2100 atgataccctc aaagtccctc accaccactg gacgagcaga acaggactg ccagggtctg   2160 atggagaagt ttcagtttga actgactctc gatgaggaag attctgaagg acctgagaag   2220
gagggagagg gacacagcta tttcagcagc acaaagacgc tttgtgtgat tgatccagaa   2280
aacagagatt ccctgggaga gactgacata gacattgcaa cagaagacaa gtcccccgtg   2340
gatacataat cccctctcc ctgtggagat gaacattcta tccttgatga gcatgccagc   2400
tatgtggtag ggccagccca ccatgggggc caagacctgc acaggacaag gccacctgg   2460 cctttcagtt acttgagttt ggagtcagaa agcaagacca ggaagcaaat agcagctcag   2520
```

| | | |
|---|---|---|
| gaaatcccac | ggttgacttg ccttgatggc aagcttggtg gagagggctg aagctgttgc | 2580 |
| tgggggccga | ttctgatcaa gacacatggc ttgaaaatgg aagacacaaa actgagagat | 2640 |
| cattctgcac | taagtttcgg gaacttatcc ccgacagtga ctgaactcac tgactaataa | 2700 |
| cttcatttat | gaatcttctc acttgtccct ttgtctgcca acctgtgtgc ctttttgta | 2760 |
| aaacattttc | atgtctttaa aatgcctgtt gaatacctgg agtttagtat caacttctac | 2820 |
| acagataagc | tttcaaagtt gacaaacttt tttgactctt tctggaaaag ggaagaaaa | 2880 |
| tagtcttcct | tctttcttgg gcaatatcct tcactttact acagttactt ttgcaaacag | 2940 |
| acagaaagga | tacacttcta accacatttt acttccttcc cctgttgtcc agtccaactc | 3000 |
| cacagtcact | cttaaaactt ctctctgttt gcctgcctcc aacagtactt ttaacttttt | 3060 |
| gctgtaaaca | gaataaaatt gaacaaatta gggggtagaa aggagcagtg gtgtcgttca | 3120 |
| ccgtgagagt | ctgcatagaa ctcagcagtg tgccctgctg tgtcttggac cctgcaatgc | 3180 |
| ggccgc | | 3186 |

<210> SEQ ID NO 47
<211> LENGTH: 2745
<212> TYPE: DNA
<213> ORGANISM: Homo sapiens

<400> SEQUENCE: 47

| | | |
|---|---|---|
| gcccagctg | ctgagaggag ttgcctgaga gtgacctttg catctgcctg tccagccagc | 60 |
| atggaaccaa | agcggatcag agagggctac cttgtgaaga aggggagcgt gttcaatacg | 120 |
| tggaaaccca | tgtgggttgt attgttagaa gatggaattg aattctataa gaagaaaagt | 180 |
| gacaacagcc | ccaaaggaat gatcccgctg aaagggagca ctctgactag cccttgtcaa | 240 |
| gactttggca | aaaggatgtt tgtgtttaag atcactacga ccaaacagca ggaccacttc | 300 |
| ttccaggcag | ccttcctgga ggagagagat gcctgggttc gggatatcaa taaggccatt | 360 |
| aaatgcattg | aaggaggcca gaaatttgcc aggaaatcta ccaggaggtc cattcgactg | 420 |
| ccagaaacca | ttgacttagg tgccttatat ttgtccatga agacactga aaaaggaata | 480 |
| aaagaactga | atctagagaa ggacaagaag attttaatc actgcttcac aggtaactgc | 540 |
| gtcattgatt | ggctggtatc caaccagtct gttaggaatc gccaggaagg cctcatgatt | 600 |
| gcttcatcgc | tgctcaatga ggggtatctg cagcctgctg gagacatgtc caagagtgca | 660 |
| gtggatggaa | ctgctgaaaa cccttttcctg gacaaccctg atgccttcta ctactttcca | 720 |
| gacagtgggt | tcttctgtga agagaattcc agtgatgatg atgtgattct gaaagaagaa | 780 |
| ttcagagggg | tcattatcaa gcagggatgt ttactgaagc aggggcatag aaggaaaaac | 840 |
| tggaaagtga | ggaagttcat cttgagagaa gaccctgcct acctgcacta ctatgaccct | 900 |
| gctggggcag | aagatcccct gggagcaatt cacttgagag ctgtgtggt gacttcagtg | 960 |
| gagagcaact | caaatggcag gaagagtgag gaagagaacc tttttgagat catcacagca | 1020 |
| gatgaagtgc | actatttctt gcaagcagcc accccaagg agcgcacaga gtggatcaaa | 1080 |
| gccatccaga | tggcctcccg aactgggaag taaagagact cctgcattcc tcctcccctc | 1140 |
| ctgagggaag | cccatggaca agctcagtcc aggacctgtc cacttctgtg acaaatcaac | 1200 |
| gggaaacagc | ccaggggtgg gaagttttca tttgcagggg ggtctgaatg taactcacca | 1260 |
| tgtggtgtgc | aaggttcccc tgcattgtat tgctcactgc agcccctctg ccctatcca | 1320 |
| tgaccccaa | gcagatataa caagctgtgc agcctcagta ggctgcttgc cctctccagc | 1380 |
| ctcagggcct | cttctggaaa atgaagaaat tcaactagta gattcctgag gtcccctag | 1440 |

```
cttaaaaaaa aaaaaatctg ccccatgatt ctaacactcg cagtagtgat agtgtatcta    1500
gttgttctgc tggtgtcctt ccttggctaa gtcttggcct tcagttatct tcaaatgtac    1560
cagaacctga gccaacgcct ccctgtgaaa ctgttgctga tctgtagtac agtaccagga    1620
agaaacctct tttgttctct ttagacatct tctacttgct cttggccttg agatcgtgta    1680
acaaaatgaa ggagggctct cttctttctt cctcatccta ctcaaaaact tcccgagagc    1740
agtggtggtt ttgagggttt tgacttctat tactttggc agcctggaaa gttgtgtctt     1800
ctgggaaaga gacccgggga ggccaggagt agctgagggt cctttctgtg cccttaaacc    1860
gcccagagga gccctattcc actctggttt taggctgatc tgagagggtc tccctttgtt    1920
cctttctgga gcatttctct aacgtttatt acaattagga gggggacccc acatctgtga    1980
gattctgttt catttgaggt ttacagaaaa aaaaaagtgg ccagatgtgt tccccccatg    2040
ggtgagaggc ctgggcaact gcctggtgaa tgtgtcttgc ggcagctgca gcaagtggag    2100
gggctgaact actggccagc tcactggatg atgggttaat acaacaactg cactgtaagg    2160
actcagagcc acacagaact tctgagaggg gctgttagca ttgcgcagca tcttcagttc    2220
tccagtaaat gatattgcgt tcgtgcctca gctttaagca caagtagcag cagctcctgc    2280
ttgagttctg agggcatcat ggccctatga ttaaccagag tgatctaacc tagactaaaa    2340
ttgggaactt atttgcaatt tttgaccctg accactaact agtgattctt ctccaaaatt    2400
gagaaagaca gcacccattg aaacagatat gtgtgtgaaa gtatattttt caattccaga    2460
tttttaattt taaggctcca ggaaagaaag gagagtagaa catttttcct cattttatca    2520
aatcctctct tgccctccct caattcccct gtaacattcc tgaagctgtt cccactccca    2580
gatggtttta tcaatagcct agaggtaaag aactgtcttt ttctctgatt ctttaataaa    2640
ttatctttat agaatatgca caagttttc tacactcagt gttaaagtat ttattaatgg     2700
gaagtcaact taatgttttg aaataaatat atgactctgt ttaat                   2745

<210> SEQ ID NO 48
<211> LENGTH: 1820
<212> TYPE: DNA
<213> ORGANISM: Homo sapiens

<400> SEQUENCE: 48
gcggcgacga cggcggcggc agcgctccaa ctggctcctc gctccgggct ccgccgtcga      60
gccgggagag agcctccgcc agcggccagg caccagccag acgacgccag cgaccccggc    120
ctctcggcgg caccgcgcta actcaggggc tgcataggca cccagagccg aactccaaga    180
tgggaggcaa gctcagcaag aagaagaagg gctacaatgt gaacgacgag aaagccaagg    240
agaaagacaa gaaggccgag ggcgcggcga cggaagagga ggggacccccg aaggagagtg   300 agccccaggc ggccgcagag cccgccgagg ccaaggaggg caaggagaag cccgaccagg    360
acgccgaggg caaggccgag gagaaggagg gcgagaagga cgcggcggct gccaaggagg    420
aggccccgaa ggcggagccc gagaagacgg agggcgcggc agaggccaag gctgagcccc    480
cgaaggcgcc cgagcaggag caggcggccc ccggccccgc tgcgggcggc gaggcccca    540 aagctgctga ggccgccgcg gcccggccg agagcgcggc ccctgccgcc ggggaggagc    600
ccagcaagga ggaagggaa cccaaaaaga ctgaggcgcc cgcagctcct gccgcccagg    660
agaccaaaag tgacggggcc ccagcttcag actcaaaacc cggcagctcg gaggctgccc    720
cctcttccaa ggagaccccc gcagccacgg aagcgcctag ttccacaccc aaggcccagg    780
gccccgcagc ctctgcagaa gagcccaagc cggtggaggc ccggcagct aattccgacc     840
```

```
aaaccgtaac cgtgaaagag tgacaaggac agcctatagg aaaaacaata ccacttaaaa      900
caatctcctc tctctctctc tctctctctc tctatctctc tctctatctc ctctctctct      960
ctcctctcct atctctcctc tctctctctc ctatactaac ttgtttcaaa ttggaagtaa     1020
tgatatgtat tgcccaagga aaaatacagg atgttgtccc atcaagggag ggaggggtg      1080 ggagaatcca aatagtattt ttgtggggaa atatctaata taccttcagt caactttacc     1140
aagaagtcct ggatttccaa gatccgcgtc tgaaagtgca gtacatcgtt tgtacctgaa     1200
actgccgcca catgcactcc tccaccgctg agagttgaat agcttttctt ctgcaatggg     1260
agttgggagt gatgcgtttg attctgccca cagggcctgt gccaaggcaa tcagatcttt     1320
atgagagcag tattttctgt gttttctttt taatttacag cctttcttat tttgatattt     1380
ttttaatgtt gtggatgaat gccagctttc agacagagcc cacttagctt gtccacatgg     1440
atctcaatgc caatcctcca ttcttcctct ccagatattt ttgggagtga caaacattct     1500
ctcatcctac ttagcctacc tagatttctc atgacgagtt aatgcatgtc cgtggttggg     1560
tgcacctgta gttctgttta ttggtcagtg gaaatgaaaa aaaaaaaaaa aaaaagtctg     1620
cgttcattgc agttccagtt tctcttccat tctgtgtcac agacaccaac acaccactca     1680
ttggaaaatg gaaaaaaaaa acaaaaaaaa aacaaaaaaa tgtacaatgg atgcattgaa     1740
attatatgta attgtataaa tggtgcaaca gtaataaagt taaacaatta aaagaaaaa      1800 aaaaaaaaaa aaaaaaaaa                                                  1820

<210> SEQ ID NO 49
<211> LENGTH: 1828
<212> TYPE: DNA
<213> ORGANISM: Homo sapiens

<400> SEQUENCE: 49
ctacaaggag gcaggcaaga cagcaaggca tagagacaac atagagctaa gtaaagccag       60
tggaaatgaa gagtcttcca atcctactgt tgctgtgcgt ggcagtttgc tcagcctatc      120
cattggatgg agctgcaagg ggtgaggaca ccagcatgaa ccttgttcag aaatatctag      180
aaaactacta cgacctcaaa aaagatgtga acagtttgt taggagaaag acagtggtc       240 ctgttgttaa aaaatccga gaaatgcaga agttccttgg attggaggtg acggggaagc      300
tggactccga cactctggag gtgatgcgca agcccaggtg tggagttcct gatgttggtc      360
acttcagaac ctttcctggc atcccgaagt ggaggaaaac ccaccttaca tacaggattg      420
tgaattatac accagatttg ccaaaagatg ctgttgattc tgctgttgag aaagctctga      480
aagtctggga gaggtgact ccactcacat tctccaggct gtatgaagga gaggctgata      540
taatgatctc tttttgcagtt agagaacatg gagacttta cccttttgat ggacctggaa      600
atgttttggc ccatgcctat gcccctgggc cagggattaa tggagatgcc cactttgatg     660
atgatgaaca atggacaaag gatacaacag ggaccaattt atttctcgtt gctgctcatg     720 aaaattggcca ctccctgggt ctcttttcact cagccaacac tgaagctttg atgtacccac     780
tctatcactc actcacagac ctgactcggt tccgcctgtc tcaagatgat ataaatggca      840
ttcagtccct ctatggacct ccccctgact cccctgagac cccctggta cccacggaac      900 ctgtccctcc agaacctggg acgccagcca actgtgatcc tgctttgtcc tttgatgctg      960
tcagcactct gagggggagaa atcctgatct ttaaagacag gcactttggg cgcaaatccc     1020
tcaggaagct tgaacctgaa ttgcatttga tctcttcatt ttggccatct cttccttcag     1080
gcgtggatgc cgcatatgaa gttactagca aggacctcgt tttcatttt aaaggaaatc     1140
```

```
aattctgggc tatcagagga aatgaggtac gagctggata cccaagaggc atccacaccc   1200
taggtttccc tccaaccgtg aggaaaatcg atgcagccat ttctgataag gaaaagaaca   1260
aaacatattt ctttgtagag gacaaatact ggagatttga tgagaagaga aattccatgg   1320
agccaggctt tcccaagcaa atagctgaag actttccagg gattgactca aagattgatg   1380
ctgtttttga agaatttggg ttcttttatt tctttactgg atcttcacag ttggagtttg   1440
acccaaatgc aaagaaagtg acacacactt tgaagagtaa cagctggctt aattgttgaa   1500
agagatatgt agaaggcaca atatgggcac tttaaatgaa gctaataatt cttcacctaa   1560
gtctctgtga attgaaatgt tcgttttctc ctgcctgtgc tgtgactcga gtcacactca   1620
agggaacttg agcgtgaatc tgtatcttgc cggtcatttt tatgttatta cagggcattc   1680
aaatgggctg ctgcttagct tgcaccttgt cacatagagt gatctttccc aagagaaggg   1740
gaagcactcg tgtgcaacag acaagtgact gtatctgtgt agactatttg cttatttaat   1800
aaagacgatt tgtcagttat tttatctt                                      1828

<210> SEQ ID NO 50
<211> LENGTH: 3105
<212> TYPE: DNA
<213> ORGANISM: Homo sapiens

<400> SEQUENCE: 50
gattcccggg cccacccgac ccagcggcgc gaccctggcc ctccgggacc ctccgctgac     60
tccaccgcgc acttcccggg acccccacac acatcccagc cctccggccg atccctccct    120
actcggtgcc gggtgccccc cgccctctcc aggcccggat ctcctccccc aggtccccgg    180
ggcggcccca gccaggcccc cttcgaaccc cgccggcggc ccgggctggg cgcaccatg     240 cggctgcggc tccggcttct ggcgctgctg cttctgctgc tggcaccgcc cgcgcgcgcc    300
ccgaagccct cggcgcagga cgtgagcctg gcgtggact ggctgactcg ctatggttac    360
ctgccgccac cccacccctgc ccaggcccag ctgcagagcc ctgagaagtt gcgcgatgcc    420
atcaaagtca tgcagaggtt cgcggggctg ccggagaccg gccgcatgga cccagggaca    480
gtggccacca tgcgtaagcc ccgctgctcc ctgcctgacg tgctgggggt ggcggggctg    540
gtcaggcggc gtcgccggta cgctctgagc ggcagcgtgt ggaagaagcg aaccctgaca    600
tggagggtac gttccttccc ccagagctcc cagctgagcc aggagaccgt gcgggtcctc    660
atgagctatg ccctgatggc ctggggcatg gagtcaggcc tcacatttca tgaggtggat    720
tccccccagg gccaggagcc cgacatcctc atcgactttg cccgcgcctt ccaccaggac    780
agctacccct cgacgggtt gggggcacc ctagcccatg ccttcttccc tggggagcac    840
cccatctccg gggacactca ctttgacgat gaggagacct ggacttttgg gtcaaaagac    900
ggcgagggga ccgacctgtt tgccgtggct gtccatgagt ttggccacgc cctgggcctg    960
ggccactcct cagcccccaa ctccattatg aggcccttct accagggtcc ggtgggcgac   1020
cctgacaagt accgcctgtc tcaggatgac cgcgatggcc tgcagcaact ctatgggaag   1080 gcgcccaaa cccatatga caagcccaca aggaaacccc tggctcctcc gccccagccc    1140
ccggcctcgc ccacacacag cccatccttc ccatccctg atcgatgtga gggcaatttt   1200
gacgccatcg ccaacatccg agggggaaact ttcttcttca aggcccctg gttctggcgc   1260 ctccagcccct ccggacagct ggtgtccccg cgaccgcac ggctgcaccg cttctgggag   1320
gggctgcccg cccaggtgag ggtggtgcag gccgcctatg ctcggcaccg agacggccga   1380
atcctcctct ttagcgggcc ccagttctgg gtgttccagg accggcagct ggagggcggg   1440
```

| | | |
|---|---|---|
| gcgcggccgc tcacggagct ggggctgccc ccgggagagg aggtggacgc cgtgttctcg | 1500 | |
| tggccacaga acgggaagac ctacctggtc cgcggccggc agtactggcg ctacgacgag | 1560 | |
| gcggcggcgc gcccggaccc cggctaccct cgcgacctga gcctctggga aggcgcgccc | 1620 | |
| ccctcccctg acgatgtcac cgtcagcaac gcaggtgaca cctacttctt caagggcgcc | 1680 | |
| cactactggc gcttcccaa gaacagcatc aagaccgagc cggacgcccc ccagcccatg | 1740 | |
| gggcccaact ggctggactg ccccgccccg agctctggtc ccgcgccccc caggcccccc | 1800 | |
| aaagcgaccc ccgtgtccga aacctgcgat tgtcagtgcg agctcaacca ggccgcagga | 1860 | |
| cgttggcctg ctcccatccc gctgctcctc ttgcccctgc tggtgggggg tgtagcctcc | 1920 | |
| cgctgatggg gggagccatc cagaccgaac agcgccccgc ctggccactg cgtctggcat | 1980 | |
| tcctgggtcg ttagaggaca ggcctgactg cgaagctgtg ccttgcccct ctcccacccg | 2040 | |
| cagtttctca ccccgttctg ctcccacaag gcccccctac agtcactgcc acactggtgg | 2100 | |
| ggacctggga cccagacccg gaaccagccc agatatcacc cctgaggacc catgcgccac | 2160 | |
| gtcctgggtg gtggaatcag tggctggagg gacgacccct gctctccagg ctgttaacct | 2220 | |
| tttccgttgc tcccccgcca cccacctcct cctcccagg ccacccaact tgggcacctc | 2280 | |
| cctgggccca gaactgcctt ccattcaatg gggaacccctt ctatccccaa gaaccccttc | 2340 | |
| cctgcttgca ccctggagag aacagcttga ctcccatcaa ctcaacgctg gtggaaagac | 2400 | |
| agggaccgaa ccctggctca ggcctggtca ttgcctcctc agcactccct cctgggaggc | 2460 | |
| cttagctcta gagtgagggg tgggtggaac ctggggcac ctcgttcacc ctgtccccac | 2520 | |
| tccccacagt tttaggatct aaatgattgc ctctggaact attcttctag actatcccac | 2580 | |
| atcagaatca ctgggaaatt taagtttgca gatcccacac tcaccctgaa tcctcactca | 2640 | |
| gggtggggtc aggaatctgc attttaacta gtcgcgggga ttgtgggggg cagtagctgg | 2700 | |
| ctgtttcgtg gcatttctgt ggctctgcag tgttcctcca ccccaggacc aatatgttca | 2760 | |
| ggccacaccg atggcctgaa ccccatgggt agagtcactt aggggccact tcctaagttg | 2820 | |
| ctgtccagcc tcagtgaccc cctagtgctt cctggagctg aggctgtggg cggctgtccc | 2880 | |
| agcaaccatg cgaggggttg ccccagttgc tcatacaaac agatcagcat gaggacagaa | 2940 | |
| ggcaggagac tttggtcagt tacctgggaa ttctgggctg ccaggaaacg atttgggcct | 3000 | |
| ctgtcagttt cttttccatg tatgaggagg gggaaatttg tatattagaa acttattcat | 3060 | |
| cccactcagg acaataaaaa cgaatgtaca aaaaaaaaa aaaaa | 3105 | |

<210> SEQ ID NO 51
<211> LENGTH: 1154
<212> TYPE: DNA
<213> ORGANISM: Homo sapiens

<400> SEQUENCE: 51

| | | |
|---|---|---|
| aatcaagaag ttggcgtgca gctgggagag ctagactaag ttggtcatga tgcagaagct | 60 | |
| actcaaatgc agtcggcttg tcctggctct tgccctcatc ctggttctgg aatcctcagt | 120 | |
| tcaaggtaag actcaggagt cttgttcccc agccatcttc tctgtaagcc ctgtggtcca | 180 | |
| tgcaagtcat tatattcatt ttaaggcata gaatgtataa tattgtgaga aggaggcaa | 240 | |
| agaagaagga tttggggtcg ctgaacccctt taatatgagt tctgttaagt ttggtaccaa | 300 | |
| gaaaaattaa actctgtggc gtgtgcagtc ttgtaaactc ttacaatgat tgaaatgtgc | 360 | |
| tattttggga tgaaaatgtg aggttttataa atttaaaag ctcaaaaaag gaatctagaa | 420 | |
| aatgactcct gtgcctgttg catggaggag atggcacctt tgactgttgg ggggtgtctg | 480 | |

```
cctaccccta agtgtctaca tcagccccaa gttttagtgc gctgtgacgg tgtcattgtt      540
attttaacac tgggagacgt tatattccaa ttggggtgaa tctgactgtg tgtattttct      600 tttcttttt  tttttttaaa gataaacttg gttcttactg aaaactcaat tatggttaga      660
catagttcat gtaaaacctc tcagatttta aagagaaggc caaataattt ggtatttgtg      720
ctcttgctca gagaagcatc atattcggaa atatcttcct aggtttatct accatttagt      780
gttgtttagt cagactgaaa caacttaaaa cctgtaatga ctaagacaat gaaaatgata      840
ggcttgtaag aaaaatacaa tttgttattc tttggcaaat aaggaatcat gtctaaataa      900
gacggaggtc atggcttgat agagagatgg ctgaacctat agtagaaaaa cactaggttc      960
cgccaaatgg taagggaaat gttgagtcac aatgacacac atgtcctaga tttgtttcgt     1020
caaagcgact tttggttgtc atgatcttac ttccggtgga ggttgcagtg agctgagatc     1080
atgccattgc actccaggct aggcaacaga gtgcaactcc gtcccaaaaa aaaaaaaaaa     1140
aaaaaaaaaa aaaa                                                       1154

<210> SEQ ID NO 52
<211> LENGTH: 562
<212> TYPE: DNA
<213> ORGANISM: Homo sapiens
      <220
<221> NAME/KEY: unsure
<222> LOCATION: (61)(113)(496)
<223> OTHER INFORMATION: Wherein n can be a, c, t, or g

<400> SEQUENCE: 52
atcccaaagc ccagtacaca agtatctacg gagccctcaa gaaaatcatg cggaccgaag       60
ncttctggag gcccttgcga ggcgtcaacg tcatgatcat gggtgcaggg ccngcccatg      120
ccatgtattt tgcctgctat gaaaacatga aaaggacttt aaatgacgtt ttccaccacc      180
aaggaaacag ccaccaccta gccaacggta ttttgaaagc gtttgtctgg agttagaaag      240
ttctcttctt caacacgtcc ctccccaggg tgttcctccc tgtgacccag ccgcctcgac      300
ttcggcccgc ttgctcacga ataaagaact cagagttgtg tgtgcaatgc acacccagac      360
acacgcacgc acacacacgc gcgcgcacac acatgctttt ttctgttccc ctccgctttc      420
tgaagcctgg ggagaaatca gtgacagagg tgttttggtt ttattgttat gtgggttttc      480
ttttgtattt tttttngttt gttttgtttt taaacattca aaagcaatta atgatcagac      540
ataggagaaa ccctgaatag aa                                              562

<210> SEQ ID NO 53
<211> LENGTH: 1613
<212> TYPE: DNA
<213> ORGANISM: Homo sapiens

<400> SEQUENCE: 53
cgggttctac ctgccttgaa gaagacacct gacctgcgga gtgagtgacc agtgtttcca       60
gagcctggca atggatgcca ttcacatcgg catgtccagc acccccctgg tgaagcacac      120
tgctggggct gggctcaagg ccaacagacc ccgcgtcatg tccaagagtg gcacagcaa      180 cgtgagaatt gacaaagtgg atggcatata cctactctac ctgcaagacc tgtggaccac      240
agttatcgac atgaagtgga gatacaaact caccctgttc gctgccactt ttgtgatgac      300
ctggttcctt tttggagtca tctactatgc catcgcgttt attcatgggg acttagaacc      360
cgatgagccc atttcaaatc ataccccctg catcatgaaa gtggactctc tcactggggc      420
gtttctcttt tccctggaat cccagacaac cattggctat ggagtccgtt ccatcacaga      480
```

```
ggaatgtcct catgccatct tcctgttggt tgctcagttg gtcatcacga ccttgattga    540
gatcttcatc accggaacct tcctggccaa aatcgccaga cccaaaaagc gggctgagac    600
catcaagttc agccactgtg cagtcatcac caagcagaat gggaagctgt gcttggtgat    660
tcaggtagcc aatatgagga agagcctctt gattcagtgc cagctctctg gcaagctcct    720
gcagacccac gtcaccaagg aggggagcg gattctcctc aaccaagcca ctgtcaaatt     780
ccacgtggac tcctcctctg agagcccctt cctcattctg cccatgacat tctaccatgt    840
gctggatgag acgagccccc tgagagacct cacaccccaa aacctaaagg agaaggagtt    900
tgagcttgtg gtcctcctca atgccactgt ggaatccacc agcgctgtct gccagagccg    960
aacatcttat atcccagagg aaatctactg gggttttgag tttgtgcctg tggtatctct   1020
ctccaaaaat ggaaaatatg tggctgattt cagtcagttt gaacagattc ggaaaagccc   1080
agattgcaca ttttactgtg cagattctga aaacagcaa ctcgaggaga agtacaggca    1140
ggaggatcag agggaaagag aactgaggac acttttatta aacagagca atgtctgatc    1200 acagggcgc catccaggtt taaccctgca agctgtttcc acatcagaac tcccttcaaa    1260
cacaaagatt gctgtgaaaa cgaaaatgtg tagacgcact ctcaaaaact gcacggacat   1320
acaaaatcaa tcttttcctt tgatcttgtg gctaaaccag catttctgtg tttgagagat   1380
ttcctgttag gtgcttcgtc tgaaagtgaa ctctcataat tcaaattgta taaaataaag   1440
ctacatttct aagagcttgg tgtagggcaa ttggaataat gtcctgttag ataaacagac   1500
atttagcaat gctgacatta aaggaaatg tatttctata caagattatt agctgtaata   1560
caagatattt atttaaccaa tgaccttatg gctgagagtt gaattgtggt tca          1613

<210> SEQ ID NO 54
<211> LENGTH: 545
<212> TYPE: DNA
<213> ORGANISM: Homo sapiens

<400> SEQUENCE: 54
ttttcctccc ttgggttctg atattgccgc actaggggat ataggagagg aaaagtaagg     60
tgcagttccc ccaacctcag acttaccagg aagcagatac atatgagtgt ggaagccgga    120
gggtgtttat gtaagagcac cttcctcact tccatacagc tctacgtggc aaattaactt    180
gagttttatt tattttatcc tctggtttaa ttacataatt ttttttttt tactttaagt     240 ttcaggatac atgtgccgaa tgtgcaggtt tgttacatag gtatatatat gccatgatgg    300
aaatatttat tttttttaagc gtaattttgc caaataataa aaacagaagg aaattgagat    360
tagagggagg tgtttaaaga gaggttatag agtagaagat ttgatgctgg agaggttaag    420
gtgcaataag aatttaggga gaaatgttgt tcattattgg agggtaaatg atgtggtgcc    480
tgaggtctgt acgttaccte ttaacaattt ctgtccttca gatggaaact ctttaacttc    540
tcgta                                                                545

<210> SEQ ID NO 55
<211> LENGTH: 521
<212> TYPE: DNA
<213> ORGANISM: Homo sapiens

<400> SEQUENCE: 55
tgttgttgct ttaggctcac ggcacgcttg cgtatgtctg ttaccatgtc actgtggtcc     60
tatgccgaat gccctcaggg gacttgaatc tttccaataa accaggttta gacagtatga    120
gtcaatgtgc agtgcagccc acacttgaga ggatgaatgt atgtgcactg tcactttgct    180
```

```
ctgggtggaa gtatgttatt gttgacttat tttctctgtg tttgttccta cagcccottt    240 ttcatatgtt gctcagtctc cctttcoctt cttggtgctt acacatctca gaccctttag    300
ccaaaccctt gccagtgaca gtattttggt tctcagttct cactgttccc tctgctcctg    360
gagcctttga ataaaaatgc acgtagctat ggagtggggt ttagctggaa aggtggcctt    420
ccaacttcac gtcaacttct ggctcctcag tttggcagta aggcagggaa gttgttttcc    480
tatttctcac tgagaagatt gtgaatattt ccatatggat t                        521
```

<210> SEQ ID NO 56
<211> LENGTH: 533
<212> TYPE: DNA
<213> ORGANISM: Homo sapiens
<220> FEATURE:
<221> NAME/KEY: unsure
<222> LOCATION: (154)(305)
<223> OTHER INFORMATION: Wherein n can be a, c, t, or g

<400> SEQUENCE: 56

```
gctcatagtc cgtcaccgaa aatagaaaat gccatccata ggtaaaatgc tgacctatag    60
aaaaaaatga actctacttt tatagcctag taaaaatgct ctacctgagt agttaaaagc    120
aattcatgaa gcctgaagct aaagagcact ctgntggttt tggcataata gctgcatttc    180
cagacctgac ctttggcccc aaccacaagt gctccaagcc ccaccagctg accaaagaaa    240
gcccaagttc tccttctgtc cttcccacaa cctccctgct cccaaaacta tgaaattaat    300
ttganccata ttaacacagc tgactcctcc agtttactta aggtagaaag aatgagttta    360
caacagatga aaataagtgc tttgggcgaa ctgtattcct tttaacagat ccaaactatt    420
ttacatttaa aaaaaaagtt aaactaaact tctttactgc tgatatgttt cctgtattct    480
agaaaaattt ttacactttc acattatttt tgtacacttt ccccatgtta agg           533
```

<210> SEQ ID NO 57
<211> LENGTH: 3822
<212> TYPE: DNA
<213> ORGANISM: Homo sapiens

<400> SEQUENCE: 57

```
tggctcagcc gcggcggtgg cggggcgca accagcgggc cgaggcggcg gcgccagcgg     60
cgccttaaat agcatccaga gccggcgcgg ggcagggagt gggctgcagt gacagccggc    120
ggcggagcgg ccggtccacg gaggagaatt cagcttagag aactatcaac acaggacaat    180
gcaagcccat gagctgttcc ggtattttcg aatgccagag ctggttgact tccgacagta    240
cgtgcgtact cttccgacca acacgcttat gggcttcgga gcttttgcag cactcaccac    300
cttctggtac gccacgagac ccaaaccoct gaagccgcca tgcgacctct ccatgcagtc    360
agtggaagtg gcgggtagtg gtggtgcacg aagatccgca ctacttgaca gcgacgagcc    420
cttggtgtat ttctatgatg atgtcacaac attatacgaa ggtttccaga ggggaataca    480
ggtgtcaaat aatggccctt gtttaggctc tcggaaacca gaccaaccct atgaatggct    540
ttcatataaa caggttgcag aattgtcgga gtgcataggc tcagcactga tccagaaggg    600
cttcaagact gccccagatc agttcattgg catctttgct caaaatagac ctgagtgggt    660
gattattgaa caaggatgct tgcttattc gatggtgatc gttccacttt atgataccct    720
tggaaatgaa gccatcacgt acatagtcaa caaagctgaa ctctctctgg tttttgttga    780
caagccagag aaggccaaac tcttattaga gggtgtagaa aataagttaa taccaggcct    840
taaaatcata gttgtcatgg atgcctacgg cagtgaactg gtggaacgag gccagaggtg    900
```

```
tggggtggaa gtcaccagca tgaaggcgat ggaggacctg ggaagagcca acagacggaa      960
gcccaagcct ccagcacctg aagatcttgc agtaatttgt ttcacaagtg aactacagg     1020 caaccccaaa ggagcaatgg tcactcaccg aaacatagtg agcgattgtt cagcttttgt    1080
gaaagcaaca gagaatacag tcaatccttg cccagatgat actttgatat ctttcttgcc    1140
tctcgcccat atgtttgaga gagttgtaga gtgtgtaatg ctgtgtcatg gagctaaaat    1200 cggattttc caaggagata tcaggctgct catggatgac ctcaaggtgc ttcaacccac     1260
tgtcttcccc gtggttccaa gactgctgaa ccggatgttt gaccgaattt tcggacaagc    1320
aaacaccacg ctgaagcgat ggctcttgga ctttgcctcc aagaggaaag aagcagagct    1380
tcgcagcggc atcatcagaa acaacagcct gtgggaccgg ctgatcttcc acaaagtaca    1440
gtcgagcctg ggcggaagag tccggctgat ggtgacagga gccgcccgg tgtctgccac     1500 tgtgctgacg ttcctcagag cagccctggg ctgtcagttt tatgaaggat acggacagac    1560
agagtgcact gccgggtgct gcctgaccat gcctggagac tggaccgcag ccatgttgg     1620 ggccccgatg ccgtgcaatt tgataaaact tgttgatgtg aagaaatga attacatggc     1680 tgccgagggc gagggcgagg tgtgtgtgaa agggccaaat gtatttcagg ctacttgaa     1740 ggacccagcg aaaacagcag aagctttgga caaagacggc tggttacaca caggggacat    1800
tggaaaatgg ttaccaaatg gcaccttgaa aattatcgac cggaaaaagc acatatttaa    1860
gctggcacaa ggagaataca tagcccctga aaagattgaa aatatctaca tgcgaagtga    1920
gcctgttgct caggtgtttg tccacggaga aagcctgcag gcatttctca ttgcaattgt    1980
ggtaccagat gttgagacat tatgttcctg ggcccaaaag agaggatttg aagggtcgtt    2040
tgaggaactg tgcagaaata aggatgtcaa aaaagctatc ctcgaagata tggtgagact    2100
tgggaaggat tctggtctga aaccatttga acaggtcaaa ggcatcacat gcaccctga     2160 attatttct atcgacaatg gccttctgac tccaacaatg aaggcgaaaa ggccagagct     2220
gcggaactat ttcaggtcgc agatagatga cctctattcc actatcaagg tttagtgtga    2280
agaagaaagc tcagaggaaa tggcacagtt ccacaatctc ttctcctgct gatggccttc    2340
atgttgttaa ttttgaatac agcaagtgta gggaaggaag cgttcgtgtt tgacttgtcc    2400 attcgggggtt cttctcatag gaatgctaga ggaaacagaa cactgcctta cagtcacctc    2460
atgttgcaga ccatgtttat ggtaatacac actttccaaa atgagcctta aaaattgtaa    2520
aggggatact ataaatgtgc taagttattt gagacttcct cagtttaaaa agtgggtttt    2580
aaatcttctg tctccctgtt tttctaatca aggggttagg actttgctat ctctgagatg    2640
tctgctactt gctgcaaatt ctgcagctgt ctgctgctct aaagagtaca gtgcactaga    2700
gggaagtgtt cccctttaaaa ataagaacaa ctgtcctggc tggagaatct cacaagcgga    2760
ccagagatct ttttaaatcc ctgctactgt cccttctcac aggcattcac agaacccttc    2820
tgattcgtaa gggttacgaa actcatgttc ttctccagtc ccctgtggtt tctgttggag    2880
cataaggttt ccagtaagcg ggagggcaga tccaactcag aaccatgcag ataaggagcc    2940
tctggcaaat gggtgctcat cagaacgcgt ggattctctt tcatggcaga atgctcttgg    3000
actcggttct ccaggcctga ttccccgact ccatccttt tcaggggtta tttaaaaatc     3060
tgccttagat tctatagtga agacaagcat ttcaagaaag agttacctgg atcagccatg    3120
ctcagctgtg acgcctgaat aactgtctac tttatcttca ctgaaccact cactctgtgt    3180
aaaggccaac agatttttaa tgtggttttc atatcaaaag atcatgttgg gattaacttg    3240
ccttttcccc caaaaaataa actctcaggc aagcatttct ttaaagctat taagggagta    3300
```

-continued

| | |
|---|---|
| tatacttgag tacttattga aatggacagt aataagcaaa tgttcttata atgctacctg | 3360 |
| atttctatga aatgtgtttg acaagccaaa attctaggat gtagaaatct ggaaagttca | 3420 |
| tttcctggga ttcacttctc cagggatttt ttaaagttaa tttgggaaat taacagcagt | 3480 |
| tcactttatt gtgagtcttt gccacatttg actgaattga gctgtcattt gtacatttaa | 3540 |
| agcagctgtt ttggggtctg tgagagtaca tgtattatat acaagcacaa cagggcttgc | 3600 |
| actaaagaat tgtcattgta ataacactac ttggtagcct aacttcatat atgtattctt | 3660 |
| aattgcacaa aaagtcaata atttgtcacc ttggggtttt gaatgtttgc tttaagtgtt | 3720 |
| ggctatttct atgttttata aaccaaaaca aaatttccaa aaacaatgaa ggaaaccaaa | 3780 |
| ataaatattt ctgcatttca ggtgaaaaaa aaaaaaaaaa aa | 3822 |

<210> SEQ ID NO 58
<211> LENGTH: 5356
<212> TYPE: DNA
<213> ORGANISM: Homo sapiens

<400> SEQUENCE: 58

| | |
|---|---|
| cgggattcgg ctggctctgc cacaccaccg cgcgccccg ctccgcccgc ccctccgggc | 60 |
| gcgtcttttc cgggctcgcg ctgagtcccg cctccgccgg ctgtccgggt gcgcgcgcgc | 120 |
| cgctgcggct ttttctctgg cctccgccgc gcgctcctcc tcgtcccagc gctagcgggc | 180 |
| acgcggttcc tttttgcgag cttccgagt gccaggcgcc ggccggctgc gaagacgcgg | 240 |
| tgggccgccc ctccgattga aatcacagaa gatattcgtg ttcttcttaa gagaaaaaga | 300 |
| ggacatttta gctttctcag ttgaaggcgt actttattgt cggcttccaa agattactaa | 360 |
| cttttatctg tatcactaag attgaactgc cttggctgta ctgctattct tactgctgct | 420 |
| tctattattg ccttcttcag cacaataagg ctttcaaaag ccaaagaata acaagaaata | 480 |
| agcaccattt tagaagcctt tccactatga aacttaagct aaatgtgctc accattattt | 540 |
| tgctgcctgt ccacttgtta ataacaatat acagtgccct tatatttatt ccatggtatt | 600 |
| ttcttaccaa tgccaagaag aaaaacgcta tggcaaagag aataaaagct aagcccactt | 660 |
| cagacaaacc tggaagtcca tatcgctctg tcacacactt cgactcacta gctgtaatag | 720 |
| acatccctgg agcagatact ctggataaat tatttgacca tgctgtatcc aagtttggga | 780 |
| agaaggacag ccttgggacc agggaaatcc taagtgaaga aaatgaaatg cagccaaatg | 840 |
| gaaaagtttt taagaagtta attcttggga attataaatg gatgaactat cttgaagtga | 900 |
| atcgcagagt gaataacttt ggtagtggac tcactgcact gggactaaaa ccaaagaaca | 960 |
| ccattgccat cttctgtgag accagggccg aatggatgat tgcagcacag acctgcttta | 1020 |
| agtacaactt tcctcttgtg actttatatg ccacacttgg caaagaagca gtagttcatg | 1080 |
| ggctaaatga atctgaggct tcctatctga ttaccagtgt tgaacttctg gaaagtaaac | 1140 |
| ttaagactgc attgttagat atcagttgtg ttaaacatat catttatgtg gacaataagg | 1200 |
| ctatcaataa agcagagtac cctgaaggat tgagattca cagcatgcaa tcagtagaag | 1260 |
| agttgggatc taacccagaa aacttgggca ttcctccaag tagaccaacg ccttcagaca | 1320 |
| tgccattgt tatgtatact agtggttcta ctggccgacc taagggagtg atgatgcatc | 1380 |
| atagcaattt gatagctgga atgacaggcc agtgtgaaaa aatacctgga ctgggaccga | 1440 |
| aggacacata tattggctac ttgccttttg ctcatgtgct agaactgaca gcagagatat | 1500 |
| cttgctttac ctatgctgc aggattggat attcttctcc gcttacactc tctgaccagt | 1560 |
| ccagcaaaat taaaaaagga agcaaaggag actgtactgt actgaagccc acacttatgg | 1620 |

```
ctgctgttcc ggaaatcatg gatagaattt ataagaatgt tatgagcaaa gtccaagaga    1680
tgaattatat tcagaaaact ctgttcaaga tagggtatga ttacaaattg gaacagatca    1740
aaaagggata tgatgcacct ctttgcaatc tgttactgtt taaaaaggtc aaggccctgc    1800
tgggagggaa tgtccgcatg atgctgtctg gaggggcccc gctatctcct cagacacacc    1860
gattcatgaa tgtctgcttc tgctgcccaa ttggccaggg ttatggactg acagaatcat    1920
gtggtgctgg gacagttact gaagtaactg actatactac tggcagagtt ggagcacctc    1980
ttatttgctg tgaaattaag ctaaaagact ggcaagaagg cggttataca attaatgaca    2040
agccaaaccc cagaggtgaa atcgtaattg gtggacagaa catctccatg ggatatttta    2100
aaaatgaaga gaaacagca gaagattatt ctgtggatga aaatggacaa aggtggtttt    2160
gcactggtga tattggagaa ttccatcccg atggatgttt acagattata gatcgtaaga    2220
aagatctagt gaagttacaa gcaggagagt atgtatctct tgggaaagta gaagctgcac    2280
tgaagaattg tccacttatt gacaacatct gtgcttttgc caaagtgat cagtcctatg    2340 tgatcagttt tgtggttcct aaccagaaaa ggttgacact tttggcacaa cagaaagggg    2400
tagaaggaac ttgggttgat atctgcaata atcctgctat ggaagctgaa atactgaaag    2460
aaattcgaga agctgcaaat gccatgaaat tggagcgatt tgaaattcca atcaaggttc    2520
gattaagccc agagccatgg accccctgaaa ctggtttggt aactgatgct ttcaaactga    2580
aaaggaagga gctgaggaac cattacctca aagacattga acgaatgtat gggggcaaat    2640
aaaatgttgt tgtcttattg acagttgtgc aggaggtagc ctggtggttt tcaacctcta    2700
gaattttaag cctttgttga actgttagaa tgtaaggtat atcattctaa agatagagta    2760
aaaagaaaac aaaaccaaaa gttattaaaa ttgttgtccg gtttacttta acttagtttt    2820
gcatagttct agtgcagctg aaattgaaaa gttatttccc tttagctgtg ttattataga    2880
gcagaaattc tgttttttaaa aattagccta agatatactt gttttttgtaa agaaaaatat    2940 ttaatgttga acaaaataaa ttggagttgg agtagaatgt agtttgagga aatttgcagc    3000
ttccaatgcc tcttgtcttc ctatttcaga agtttaaata ttaagcatga cagaaaatat    3060
gtattaacac tactcaaagc aaaagtgctg cagggctttta aaattctctt ccaaccattt    3120
atcttgaagg aaaaattcaa tagtaatata atacacaaaa tcaaataata ccttagaagg    3180
tattaagatt ataattgttg cataggttag atatagagtc attgtaatgt tgtgaataat    3240
tacagtgcct aaaataagaa tagaacaaca tatacaacac caaaaaatat ctagtaatat    3300
atttaaaggg aaattgagct gcttttttttg aaactttgag atctaaaaat aactgtaatt    3360
atttgaatga ctaagaggaa agtacatttt ttgaaatgct gaaaattgcc tttctgtgtt    3420
tattcaaact gaaaagctga gaccaagagc aaggaaggta aaagttaac aggcaaacat    3480 tttctcttag aaaaggtgat aaaatcataa gtatttggaa ttagaacct tgcacagcac    3540 tgaacctggg aaagagattt aaactctgaa tttatctttg ataacaggga ttgattttaa    3600
aatgtacatg tattaaatta catttgtaat ttaaggtctg tttgctgttg ctgatttttat    3660 tcttgatcag tagtttgcat ttcagaaagc ctttcatttt gctttaagtt tagcaaagcg    3720
gggttataat gaatgacttc cccaatatct tgcttgaact tacagtgatt aacttggatg    3780
agttttggga agttaaaggg aagaaaacac tgttatcatt ttttcctgtt tgggaagagc    3840
ttagaaactg gaaatactag atttgggaga agggcagagt tacttgataa gggacttgat    3900
gtttgtgcag taacttggga gtgtggtttc tttttgaatc tttaattaaa acctgggatt    3960
atatatccct gataaatatt cacacttgaa ccatagttac tgtaaaatgc aaaaaatctt    4020
```

```
aatactgtta ttctttgcac ttttctttaa tcattttta tatatatgca tatatatatg    4080
tgtgtgtgtg tgttgcttat gttgttttgt acagatgtgg gccaccattg caacaaaata    4140 cattctttt gctctaaaat atttatgaag aaaatactta aatgttatgt atatggtggt    4200
aataagggaa aaatcaagta ttataaacaa gaatgaaggt ttttgtaaag atttctgttc    4260
agcgttttgc aagtaaaat tttaggcaag ttttccctga agttatgtgt atgtgagtat    4320
tctcattctt cccaacttgc ctttgaagag tgaaatacca ttattatcaa gtagactact    4380
gttcagcttt tattccttcc ctggttgttt atcccttagg aatgagtttc ttagactttc    4440
ccaatatgtg atttttttc ccatttagaa tggtgatttt aaatgtgtga gtgcatgtac    4500
tatcttatct cagatatttg cacccccaat ctgcccccaa ctcccaaaag ctagaacact    4560
gccaactgat ctgttatagg tcctttagaa acacataatt aacacttaag gttgggtgct    4620
gctaattctt tgcaaaaatc caaatattgt taagggacca gggagatgcc actacccctt    4680
gattttccat ctaaaaatat acatgttat gtaaacaaat ctttccatat ccatagtgac    4740
ttttcaagta tttaagccta aagattttga tctcacattt ttatacctgt ttaaattgct    4800
cacagttatt acatacacat cagccatcaa ctaaagttgt actttaaaaa tttactacaa    4860
tatgtacatt tctaagtcaa acacttgtga cttttgcttt aattccatga atgttcctgc    4920
ctccttgata tttgtattta ttctttttt ctctagagta gaggtataat tgtgtgatat    4980
ttcagaaata cagataaatg attcaaaaag tcacagttaa ggagaatcat gtttctttga    5040
tcatgaataa ctgattagta agtcttgcct atattttcct gatagcatat gacaaatgtt    5100
tctaaggtaa caagatgaga acagataaag attgtgtggt gttttggatt tggagagaaa    5160
tattttaatt tttaaatgca gttacaaatt ataatgtatt catatttgta ctttctgtta    5220
aaatgcatga ttgcagaatt gtttagattt tgtgtttatt cttgatgaaa gctttgttt    5280 gttcttgttt ttaagtttgc actcaaatct taagaaataa atccacccat gttatcaaaa    5340
aaaaaaaaaa aaaaaa                                                    5356

<210> SEQ ID NO 59
<211> LENGTH: 3573
<212> TYPE: DNA
<213> ORGANISM: Homo sapiens

<400> SEQUENCE: 59
gcgttcagcg gacgcgcgcg gcctcgatct ctggactcgt cacctgcccc tcccctccc      60 gccgccgtca cccaggaaac cggccgcaat cgccggccga cctgaagctg gtttcatggc    120
agcctcaaag aaggcagttt tggggccatt ggtgggggcg gtggaccagg gcaccagttc    180
gacgcgcttt ttggttttca attcaaaaac agctgaacta cttagtcatc atcaagtaga    240
aataaaacaa gagttcccaa gagaaggatg ggtggaacag gaccctaagg aaattctaca    300
ttctgtctat gagtgtatag agaaaacatg tgagaaactt ggacagctca atattgatat    360
ttccaacata aaagctattg gtgtcagcaa ccagagggaa accactgtag tctgggacaa    420
gataactgga gagcctctct acaatgctgt ggtgtggctt gatctaagaa cccagtctac    480
cgttgagagt cttagtaaaa gaattccagg aaataataac tttgtcaagt ccaagacagg    540
ccttccactt agcacttact tcagtgcagt gaaacttcgt tggctccttg acaatgtgag    600
aaaagttcaa aaggccgttg aagaaaaacg agctcttttt gggactattg attcatggct    660
tatttggagt ttgacaggag gagtcaatgg aggtgtccac tgtacagatg taacaaatgc    720
aagtaggact atgcttttca acattcattc tttggaatgg gataaacaac tctgcgaatt    780
```

| | |
|---|---|
| ttttggaatt ccaatggaaa ttcttccaaa tgtccggagt tcttctgaga tctatggcct | 840 |
| aatgaaagct ggggccttgg aaggtgtgcc aatatctggg tgtttagggg accagtctgc | 900 |
| tgcattggtg ggacaaatgt gcttccagat tggacaagcc aaaaatacgt atggaacagg | 960 |
| atgtttctta ctatgtaata caggccataa gtgtgtattt tctgatcatg gccttctcac | 1020 |
| cacagtggct tacaaacttg gcagagacaa accagtatat tatgctttgg aaggttctgt | 1080 |
| agctatagct ggtgctgtta ttcgctggct aagagacaat cttggaatta taaagacctc | 1140 |
| agaagaaatt gaaaaacttg ctaaagaagt aggtacttct tatggctgct acttcgtccc | 1200 |
| agcattttcg gggttatatg caccttattg ggagcccagc gcaagaggga taatctgtgg | 1260 |
| actcactcag ttcaccaata aatgccatat tgcttttgct gcattagaag ctgtttgttt | 1320 |
| ccaaactcga gagattttgg atgccatgaa tcgagactgt ggaattccac tcagtcattt | 1380 |
| gcaggtagat ggaggaatga ccagcaacaa aattcttatg cagctacaag cagacattct | 1440 |
| gtatatacca gtagtgaagc cctcaatgcc cgaaaccact gcactgggtg cggctatggc | 1500 |
| ggcaggggct gcagaaggag tcggcgtatg gagtctcgaa cccgaggatt tgtctgccgt | 1560 |
| cacgatggag cggtttgaac ctcagattaa tgcggaggaa agtgaaattc gttattctac | 1620 |
| atggaagaaa gctgtgatga agtcaatggg ttgggttaca actcaatctc cagaaagtgg | 1680 |
| tattccataa aacctaccaa ctcatggatt cccaagatgt gagcttttta cataatgaaa | 1740 |
| gaacccagca attctgtctc ttaatgcaat gacactattc atagactttg attttattta | 1800 |
| taagccactt gctgcatgac cctccaagta gacctgtggc ttaaaataaa gaaaatgcag | 1860 |
| caaaaagaat gctatagaaa tatttggtgg ttttttttt ttttaaacat ccacagttaa | 1920 |
| ggttgggcca gctacctttg gggctgaccc cctccattgc cataacatcc tgctccattc | 1980 |
| cctctaagat gtaggaagaa ttcggatcct taccattgga atcttccatc gaacatactc | 2040 |
| aaacactttt ggaccaggat ttgagtctct gcatgacata tacttgatta aaaggttatt | 2100 |
| actaacctgt taaaaatcag cagctctttg cttttaacag acaccctaaa agtcttcttt | 2160 |
| tctacatagt tgaagacagc aacatcttca ctgaatgttt gaatagaaac ctctactaaa | 2220 |
| ttattaaaat agacatttag tgttctcaca gcttggatat ttttctgaaa agttatttgc | 2280 |
| caaaactgaa atccttcaga tgttttccat ggtcccacta attataatga ctttctgtct | 2340 |
| ggatcttata ggaaaagata cttctttttt tcttccatct ttccttttta tatttttac | 2400 |
| tttgtatgta aacatacat gcctatatat tttatacact gagggtagcc catttataaa | 2460 |
| ttaagagcac attatattca gaaggttcta acagggctgg tcttaagtga accactgtgt | 2520 |
| atataaatat gttggaaaac agctgtatac atttttgggc aacggttatg cataatattt | 2580 |
| accaggagaa ttttttctt aacaagccaa catttaaaat ttatgtttta tgtcaataaa | 2640 |
| agaaaatata ctttattgtg acttcaacta tatttcttat cccttacatt tttatttaat | 2700 |
| tgtcttagct taaaaaaga agaaactgtg gaatactaca gtaaatattg ttttcaaaca | 2760 |
| caagcaataa ttcaaatagt tattttctt ttgaattaat tttagacata ttttggatcc | 2820 |
| tattgagggg ataagaggat gtcaaaaaag ttaaatacct aagtagaaaa aaatatagaa | 2880 |
| ataaagccaa gaatctcttt cagttcaaat gttatcaatt gttaataaga aattgctatc | 2940 |
| tgggatgaca gaattacctc tgcttagtat ctcattataa ctgaaagaag gtttatcatt | 3000 |
| acaaataccc tccaatgaaa ccaagaattt ctcaaaatat ttaatgtcac atattataag | 3060 |
| aagttaccta atcctgcttc ttaacatcaa ttttttaaaaa tatcttaaaa ttactttgtt | 3120 |
| ttgtagtaaa cagtgaagaa aagattgcct cctaattatt tttttcaatg agtgctgaat | 3180 |

| | |
|---|---|
| gggaaaacat ttatatctta ctataaaagg ttctgttttg tttggaatca atggtagctt | 3240 |
| tattgactgt tctgattgtg ctgtttctaa tttattgaat ctgctaggtt ttattgatgc | 3300 |
| agccaccact taagtgacat aaatattata gaaaggtact gtgaaatgat cactttgtgg | 3360 |
| caggggtact tttaaacata aatgtttcta caaaagtagg ttgagttcat tgtaaataat | 3420 |
| tgtgaaagcc actgttcaaa taattttaag attacattaa ttttctata aattggaaga | 3480 |
| tttataaatg tttgaaattg tacacattga tatttaatga caaatttact taaaataaat | 3540 |
| tgaccccttg ttcttaaaaa aaaaaaaaaa aaa | 3573 |

<210> SEQ ID NO 60
<211> LENGTH: 2339
<212> TYPE: DNA
<213> ORGANISM: Homo sapiens

<400> SEQUENCE: 60

| | |
|---|---|
| aaaaaaataa tggcattatt tgggccactt ggaaaacccg gtggtattcc atgaagaaaa | 60 |
| ccactatgaa gataatccca ttcaccagac tcacaattgg agaaggacag caacaccacc | 120 |
| tgggggagc caaacaggct ggagacagaa actcccggtg tggcagctga gatggcccag | 180 |
| gaaagaacta tattaccttc aaaaagagag gtacatgcga tgtttgaggt ggcatgaagc | 240 |
| tcagtggtgt tatattggaa tgagtgagtg accatcctgg agccttcctg aaagaggatt | 300 |
| ggaacatcag ttaacatctg accactgcca gcgcaccccc tcccacccac gtcgattgca | 360 |
| tctctgggct ccaggataa agcaggtctt ggggtgcacc atgatttcac cattcttagt | 420 |
| actggccatt ggcacctgcc ttactaactc cttagtgcca gagaaagaga aagaccccaa | 480 |
| gtactggcga gaccaagcgc aagagacact gaaatatgcc ctggagcttc agaagctcaa | 540 |
| caccaacgtg gctaagaatg tcatcatgtt cctgggagat gggatgggtg tctccacagt | 600 |
| gacggctgcc cgcatcctca agggtcagct ccaccacaac cctggggagg agaccaggct | 660 |
| ggagatggac aagttcccct tcgtggccct ctccaagacg tacaacacca agcccaggt | 720 |
| ccctgacagc gccggcaccg ccaccgccta cctgtgtggg gtgaaggcca atgagggcac | 780 |
| cgtgggggta agcgcagcca ctgagcgttc ccggtgcaac accacccagg ggaacgaggt | 840 |
| cacctccatc ctgcgctggg ccaaggacgc tgggaaatct gtgggcattg tgaccaccac | 900 |
| gagagtgaac catgccaccc ccagcgccgc ctacgcccac tcggctgacc gggactggta | 960 |
| ctcagacaac gagatgcccc ctgaggcctt gagccagggc tgtaaggaca tcgcctacca | 1020 |
| gctcatgcat aacatcaggg acattgacgt gatcatgggg ggtggccgga atacatgta | 1080 |
| ccccaagaat aaaactgatg tggagtatga gagtgacgag aaagccaggg gcacgaggct | 1140 |
| ggacggcctg gacctcgttg acacctggaa gagcttcaaa ccgagacaca gcactccca | 1200 |
| cttcatctgg aaccgcacgg aactcctgac ccttgacccc cacaatgtgg actacctatt | 1260 |
| gggtctcttc gagccggggg acatgcagta cgagctgaac aggaacaacg tgacggaccc | 1320 |
| gtcactctcc gagatggtgg tggtggccat ccagatcctg cggaagaacc ccaaaggctt | 1380 |
| cttcttgctg gtggaaggag gcagaattga ccacgggcac catgaaggaa aagccaagca | 1440 |
| ggccctgcat gaggcggtgg agatggaccg ggccatcggg caggcaggca gcttgacctc | 1500 |
| ctcggaagac actctgaccg tggtcactgc ggaccattcc cacgtcttca catttggtgg | 1560 |
| atacaccccc cgtggcaact ctatctttgg tctggccccc atgctgagtg acacagacaa | 1620 |
| gaagcccttc actgccatcc tgtatggcaa tgggcctggc tacaaggtgg tgggcggtga | 1680 |
| acgagagaat gtctccatgg tggactatgc tcacaacaac taccaggcgc agtctgctgt | 1740 |

```
gccctgcgc cacgagaccc acggcgggga ggacgtggcc gtcttctcca agggccccat    1800
ggcgcacctg ctgcacggcg tccacgagca gaactacgtc ccccacgtga tggcgtatgc    1860
agcctgcatc ggggccaacc tcggccactg tgctcctgcc agctcggcag gcagccttgc    1920
tgcaggcccc ctgctgctcg cgctggccct ctaccccctg agcgtcctgt tctgagggcc    1980
cagggcccgg gcacccacaa gcccgtgaca gatgccaact tcccacacgg cagccccccc    2040 ctcaagggc agggaggtgg gggcctcctc agcctctgca actgcaagaa aggggaccca    2100
ggaaaccaaa gtctgccgcc cacctcgctc ccctctggaa tcttcccaa gggccaaacc    2160 cacttctggc ctccagcctt tgctccctcc ccgctgccct ttggccaaca gggtagattt    2220
ctcttgggca ggcagagagt acagactgca gacattctca aagcctctta tttttctagc    2280
gaacgtattt tccagacccc agaggccctg aagcctccgt ggaacattct ggatctgac    2339

<210> SEQ ID NO 61
<211> LENGTH: 3877
<212> TYPE: DNA
<213> ORGANISM: Homo sapiens

<400> SEQUENCE: 61
ctccttaggt ggaaaccctg ggagtagagt actgacagca aagaccggga aagaccatac      60
gtccccgggc aggggtgaca acaggtgtca tcttttttgat ctcgtgtgtg gctgccttcc    120
tatttcaagg aaagacgcca aggtaatttt gacccagagg agcaatgatg tagccacctc    180
ctaaccttcc cttcttgaac ccccagttat gccaggattt actagagagt gtcaactcaa    240
ccagcaagcg gctccttcgg cttaacttgt ggttggagga gagaacccttt gtggggctgc    300 gttctcttag cagtgctcag aagtgacttg cctgagggtg gaccagaaga aaggaaaggt    360
cccctcttgc tgttggctgc acatcaggaa ggctgtgatg ggaatgaagg tgaaaacttg    420
gagatttcac ttcagtcatt gcttctgcct gcaagatcat ccctttaaaag tagagaagct    480 gctctgtgtg gtggttaact ccaagaggca gaactcgttc tagaaggaaa tggatgcaag    540
cagctccggg ggccccaaac gcatgcttcc tgtggtctag cccagggaag cccttccgtg    600 ggggcccgg ctttgaggga tgccaccggt tctggacgca tggctgattc ctgaatgatg    660
atggttcgcc gggggctgct tgcgtggatt cccggtgg tggttttgct ggtgctcctc    720
tgctgtgcta tctctgtcct gtacatgttg gcctgcaccc caaaaggtga cgaggagcag    780
ctggcactgc ccagggccaa cagccccacg gggaaggagg ggtaccaggc cgtccttcag    840
gagtgggagg agcagcaccg caactacgtg agcagcctga gcggcagat cgcacagctc    900 aaggaggagc tgcaggagag gagtgagcag ctcaggaatg gcagtacca agccagcgat    960 gctgctggcc tgggtctgga caggagcccc ccagagaaaa cccaggccga cctcctggcc    1020
ttcctgcact cgcaggtgga caaggcagag gtgaatgctg cgtcaagct ggccacagag    1080 tatgcagcag tgccttcga tagctttact ctacagaagg tgtaccagct ggagactggc    1140
cttacccgcc accccgagga gaagcctgtg aggaaggaca gcgggatga gttggtggaa    1200 gccattgaat cagccttgga gaccctgaac aatcctgcag agaacagccc caatcaccgt    1260
ccttacacgg cctctgattt catagaaggg atctaccgaa cagaaaggga caaagggaca    1320
ttgtatgagc tcaccttcaa agggggaccac aaacacgaat caaacggct catcttattt    1380 cgaccattca gcccccatcat gaaagtgaaa aatgaaaagc tcaacatggc caacacgctt    1440
atcaatgtta tcgtgcctct agcaaaaagg gtggacaagt tccggcagtt catgcagaat    1500
ttcagggaga tgtgcattga gcaggatggg agagtccatc tcactgttgt ttactttggg    1560
```

```
aaagaagaaa taaatgaagt caaaggaata cttgaaaaca cttccaaagc tgccaacttc   1620
aggaacttta ccttcatcca gctgaatgga gaattttctc ggggaaaggg acttgatgtt   1680
ggagcccgct tctggaaggg aagcaacgtc cttctctttt tctgtgatgt ggacatctac   1740
ttcacatctg aattcctcaa tacgtgtagg ctgaatacac agccagggaa gaaggtattt   1800
tatccagttc ttttcagtca gtacaatcct ggcataatat acggccacca tgatgcagtc   1860
cctcccttgg aacagcagct ggtcataaag aaggaaactg attttggag agactttgga    1920 tttgggatga cgtgtcagta tcggtcagac ttcatcaata taggtgggtt tgatctggac   1980
atcaaaggct ggggcggaga ggatgtgcac ctttatcgca agtatctcca cagcaacctc   2040
atagtggtac ggacgcctgt gcgaggactc ttccacctct ggcatgagaa gcgctgcatg   2100
gacgagctga cccccgagca gtacaagatg tgcatgcagt ccaaggccat gaacgaggca   2160
tcccacggcc agctgggcat gctggtgttc aggcacgaga tagaggctca ccttcgcaaa   2220
cagaaacaga agacaagtag caaaaaaaca tgaactccca gagaaggatt gtgggagaca   2280
cttttctttt cctttttgcaa ttactgaaag tggctgcaac agagaaaaga cttccataaa   2340
ggacgacaaa agaattggac tgatgggtca gagatgagaa agcctccgat ttctctctgt   2400
tgggcttttt acaacagaaa tcaaaatctc cgctttgcct gcaaaagtaa cccagttgca   2460
ccctgtgaag tgtctgacaa aggcagaatg cttgtgagat tataagccta atggtgtgga   2520
ggttttgatg gtgtttacaa tacactgaga cctgttgttt tgtgtgctca ttgaaatatt   2580
catgatttaa gagcagtttt gtaaaaaatt cattagcatg aaaggcaagc atatttctcc   2640
tcatatgaat gagcctatca gcagggctct agtttctagg aatgctaaaa tatcagaagg   2700
caggagagga gataggctta ttatgatact agtgagtaca ttaagtaaaa taaaatggac   2760
cagaaaagaa aagaaaccat aaatatcgtg tcatattttc cccaagatta accaaaaata   2820
atctgcttat cttttggtt gtccttttaa ctgtctccgt ttttttcttt tatttaaaaa    2880
tgcacttttt ttcccttgtg agttatagtc tgcttattta attaccactt tgcaagcctt   2940
acaagagagc acaagttggc ctacattttt atattttta agaagatact ttgagatgca    3000
ttatgagaac tttcagttca aagcatcaaa ttgatgccat atccaaggac atgccaaatg   3060
ctgattctgt caggcactga atgtcaggca ttgagacata gggaaggaat ggttgtact    3120 aatacagacg tacagatact ttctctgaag agtattttcg aagaggagca actgaacact   3180
ggaggaaaag aaaatgacac tttctgcttt acagaaaagg aaactcattc agactggtga   3240
tatcgtgatg tacctaaaag tcagaaacca cattttctcc tcagaagtag ggaccgcttt   3300
cttacctgtt taaataaacc aaagtatacc gtgtgaacca acaatctct tttcaaaaca    3360 gggtgctcct cctggcttct ggcttccata agaagaaatg gagaaaaata tatatatata   3420
tatatatatt gtgaaagatc aatccatctg ccagaatcta gtgggatgga agttttgct    3480 acatgttatc caccccaggc caggtggaag taactgaatt attttttaaa ttaagcagtt   3540
ctactcaatc accaagatgc ttctgaaaat tgcattttat taccatttca aactattttt   3600
taaaaataaa tacagttaac atagagtggt ttcttcattc atgtgaaaat tattagccag   3660
caccagatgc atgagctaat tatctctttg agtccttgct tctgtttgct cacagtaaac   3720
tcattgttta aaagcttcaa gaacattcaa gctgttggtg tgttaaaaaa tgcattgtat   3780
tgatttgtac tggtagttta tgaaatttaa ttaaaacaca ggccatgaat ggaaggtggt   3840
attgcacagc taataaaata tgatttgtgg atatgaa                           3877
```

```
<210> SEQ ID NO 62
<211> LENGTH: 2779
<212> TYPE: DNA
<213> ORGANISM: Homo sapiens

<400> SEQUENCE: 62
aaaactattt gagacataaa cagttgtgtg atgtaatttt agtcgctggt gatcgcagaa      60
ttccagctca cagattggtg ctctcctctg tctcagacta ttttgctgcc atgtttacta     120
atgatgtcag agaggcaaga caagaagaaa taaaaatgga aggtgtagaa ccaaattcgt     180
tgtggtcctt gatccagtat gcttatacag gccgccttga attaaaagaa gataatattg     240
agtgcctgtt atctacagct tgccttcttc agctttcaca ggttgtagaa gcatgctgta     300
agtttttaat gaaacagctt catccatcca actgtcttgg aattcgttct tttgctgatg     360
cccaaggttg tacagatttg cataaagtgg ctcacaatta tactatggag catttcatgg     420
aagtaatcag aaaccaggaa tttgtattat taccagccag cgaaattgca aagctcttgg     480
ctagtgatga catgaacatt cctaatgagg agacaatatt gaatgcactt cttacttggg     540
tccgtcatga tttggaacag agacggaaag atctaagtaa acttttggct tatattaggc     600
tacctcttct tgcaccacag ttcctggcag acatggaaaa taatgtactt tttcgggatg     660
atatagaatg tcagaaactc attatggaag caatgaagta ccatttatta ccagagagac     720
gacccatgtt acaaagtcct cggacaaaac ctaggaagtc aactgttggt acattatttg     780
cagttggggg aatggattca acaaaggag caacaagcat tgaaaagtat gatctccgta     840
caaatatgtg gactccagta gcaaatatga atgggaggag gctacagttc ggtgttgcag     900
tgctagatga caaactgtat gtggttggag aagagatgg actgaagact ttgaatactg     960
tagagtgcta caaccccaaa acaaaaactt ggagtgtgat gccacctatg tccacacata    1020
gacatggcct tggtgtggct gtactggaag gtcccatgta tgccgtagga ggacatgatg    1080
gctggagcta tctgaacaca gtggaaagat gggaccctca ggctcgccag tggaattttg    1140
ttgccactat gtctacccct aggagtacag taggtgtggc agtactaagt ggaaagcttt    1200
atgcagttgg tggtcgtgat ggaagttctt gtctcaaatc agtagaatgt tttgatcctc    1260
atactaataa gtggacactg tgtgcacaga tgtcaaaaag gagaggtggc gtaggagtga    1320
cgacctggaa tggactgctg tatgctatag gggggcacga tgctcccgca tccaacttga    1380
cttccagact ctcagactgt gtggaaagat atgatcccaa acagacatg tggactgcag    1440 tagcatccat gggcatcagc agagatgcag tgggggtctg tttacttggt gataagttat    1500
atgctgttgg ggggtatgat ggacaggcat accttaatac tgtggaggct tatgatcccc    1560
agacaaatga gtggacccag gttgctccac tgtgcctagg aagagctgga gcttgtgttg    1620
tgactgtaaa attataattt agtgccccgt tttctacatg aagacaccgt cttcctttat    1680
taatttagta taattattct atcaatggat acattttag taaatgtgca ttgtcacaat    1740
cctgggcaca aagtgcctga tgtcaaaatg aagatagtaa acaagggag gaagcagtgg    1800 atggaccagg attaattcct ttcatttctt agtaaattaa aacctgcagc tggtggattg    1860
tgatcacaca ttcccgaagt aataagtgag gacgaatgca ctgctctgga acataaccca    1920
gtgctaactg ggggtttcat ttattcagtc aagcacatct tactcacatc cagatttatt    1980
ttcctacagt gcaaacacac cagatgaaac tttaaaatgt tactttttgt aagcttatca    2040
taaatgagtt gcagtaattt gtttgcttgt tgtttaacc acaaccacta ttttaatgat    2100
atactaaaga taacactatt tagttttttc agaaacatct gcattatatg tgtgttggtt    2160
gtggattttg tttctaaaat tggcttagtc caataaataa agaaaagcat taaggactta    2220
```

| | |
|---|---|
| aagcaacaat aaccaaataa aaacttgata ggatctttga agtctattta aatattcatt | 2280 |
| ccattacatc tagactcacc aagaactaca tgttatgatg ttaagttgaa gttgaaacat | 2340 |
| gatgttttgc attaaattta agatatgcaa atttatgtag agaaaataaa tgttatatac | 2400 |
| cctataatct ttcacctaat tagtatttaa ttatatggat ttgttttata ttataaaaga | 2460 |
| tgttttgatt ttgtcttttg atattgacaa aattgtttgg atatccttat gttctcaagt | 2520 |
| ctgtatctgc ctccctgcc ttatttctta tgttttgcca cagttaaccc attgtgcttc | 2580 |
| tttgtaatca aacagtttgt gggagaatgg gcttattgaa tgtctaaaaa ataagtttaa | 2640 |
| agtgtttgtt accctaagtt ttttacattt ttaaactcta attacatatg tgaatgttat | 2700 |
| tactctcagt gaattgttat tgtttgcaaa aatgcactgg gcagtaacat tttgtgataa | 2760 |
| atcctataag atataagtc | 2779 |

<210> SEQ ID NO 63
<211> LENGTH: 554
<212> TYPE: DNA
<213> ORGANISM: Homo sapiens
<220> FEATURE:
<221> NAME/KEY: unsure>
<222> LOCATION: (326)(353)(383)
<223> OTHER INFORMATION: Wherein n can be a, c, t, or g

<400> SEQUENCE: 63

| | |
|---|---|
| gggccctata ccagtacgtg ggccaagatg tggacgagct gagcttcaac gtgaacgagg | 60 |
| tcattgagat cctcatggaa gatccctcgg gctggtggaa gggccggctt cacggccagg | 120 |
| agggcctttt cccaggaaac tacgtggaga agatctgagc tgggccctgg gatactgcct | 180 |
| tctctttcgc ccgcctatct gcctgccggc ctggtgggga gccaggccct gccaatgaga | 240 |
| gcctcgttta cctgggctgc aatagcctaa aagtccagtc ctttggcctc cagtcctgcc | 300 |
| caggccctgg gtcaccaggt cactgntgca gcccccgccc ctgggccctg gtnttcctcc | 360 |
| aacatcacac ctgctgccca ttntccattt ctgtgtgtgt caaaggggac taacagcaga | 420 |
| atctacctcc caactgccat gtgattaaga aatgggtctt gagtcctgtg ctgttggcaa | 480 |
| agtgccaggc acagttgggg aggggggggt ccttaacaag cgtgactttg ctcattctgt | 540 |
| catcactaag gcaa | 554 |

<210> SEQ ID NO 64
<211> LENGTH: 1638
<212> TYPE: DNA
<213> ORGANISM: Homo sapiens

<400> SEQUENCE: 64

| | |
|---|---|
| tgtgtggaat caactttccg gaagcaacca gcccaccaga ggaggtcccg agcgcgagcg | 60 |
| gagacgatgc agcggagact ggttcagcag tggagcgtcg cggtgttcct gctgagctac | 120 |
| gcggtgccct cctgcgggcg ctcggtggag ggtctcagcc gccgcctcaa aagagctgtg | 180 |
| tctgaacatc agctcctcca tgacaagggg aagtccatcc aagatttacg gcgacgattc | 240 |
| ttccttcacc atctgatcgc agaaatccac acagctgaaa tcagagctac ctcggaggtg | 300 |
| tcccctaact ccaagccctc tcccaacaca aagaaccacc ccgtccgatt tgggtctgat | 360 |
| gatgagggca gatacctaac tcaggaaact aacaaggtgg agacgtacaa agagcagccg | 420 |
| ctcaagacac ctgggaagaa aaagaaaggc aagcccggga aacgcaagga gcaggaaaag | 480 |
| aaaaaacggc gaactcgctc tgcctggtta gactctggag tgactgggag tgggctagaa | 540 |
| ggggaccacc tgtctgacac ctccacaacg tcgctggagc tcgattcacg gtaacaggct | 600 |

-continued

```
tctctggccc gtagcctcag cggggtgctc tcagctgggt tttggagcct cccttctgcc    660
ttggcttgga caaacctaga attttctccc ttttatgtat ctctatcgat tgtgtagcaa    720
ttgacagaga ataactcaga atattgtctg ccttaaagca gtaccccct accacacaca    780 cccctgtcct ccagcaccat agagaggcgc tagagcccat tcctctttct ccaccgtcac    840
ccaacatcaa tcctttacca ctcttccaaa taatttcata ttcaagcttc agaagctagt    900
gaccatcttc ataatttgct ggagaagtgt gtttcttccc cttactctca cacctgggca    960
aactttcttc agtgttttc atttcttacg ttctttcact tcaagggaga atatagaagc   1020
atttgatatt atctacaaac actgcagaac agcatcatgt cataaacgat tctgagccat   1080
tcacactttt tatttaatta aatgtattta attaaatctc aaatttattt taatgtaaag   1140
aacttaaatt atgttttaaa cacatgcctt aaatttgttt aattaaattt aactctggtt   1200
tctaccagct catacaaaat aaatggtttc tgaaaatgtt taagtattaa cttacaagga   1260
tataggtttt tctcatgtat cttttttgttc attggcaaga tgaataatt tttctagggt   1320 aatgccgtag gaaaaataaa acttcacatt tatgtggctt gtttatcctt agctcacaga   1380
ttgaggtaat aatgacactc ctagactttg ggatcaaata acttagggcc aagtcttggg   1440
tctgaattta tttaagttca caacctaggg caagttactc tgcctttcta agactcactt   1500
acatcttctg tgaaatataa ttgtaccaac ctcatagagt ttggtgtcaa ctaaatgaga   1560
ttatatgtgg actaaatatc tgtcatatag taaacactca ataaattgca aaaaaaaaa   1620 aaaaaaaaaa aaaaaaaa                                                 1638
```

<210> SEQ ID NO 65
<211> LENGTH: 398
<212> TYPE: DNA
<213> ORGANISM: Homo sapiens
<220> FEATURE:
<221> NAME/KEY: unsure
<222> LOCATION: (200)(245)
<223> OTHER INFORMATION: Wherein n can be a, c, t, or g

<400> SEQUENCE: 65

```
ggaactctaa cctattcgtg tcatattgac cttttgctgc atgagtcata aattatgaaa     60
tcagtcttac agtttttgaa atgtagccag catttgtaag gctaaacctt tttcatgaac    120
tgaatttaag tgaataacca agccacagtt cctcctcaaa tggagagtga tgatcgacat    180
ttgaatctct ttgcccttn ccaacggcta tggcatcagg ttctaaaata agctcgtaat    240 ttttnccgt tattttaata atatggaaat attagcatag tgtttctttt gatagtgata    300
gactataatc catatttaaa ttttatagag aagaaatttt attgtactgt gatgtagata    360
tttattatcc aggtaaggat ttgcccggtg tgtattttt                           398
```

<210> SEQ ID NO 66
<211> LENGTH: 1906
<212> TYPE: DNA
<213> ORGANISM: Homo sapiens

<400> SEQUENCE: 66

```
cccaagacca agtcgtaata gcaacttccc ttcctcagct gcctgaactt tttttttccc     60
ttgtagctgg agagaagtgt cacattttgc tcactctcaa ccttcctcgc ccaccccctt    120
cccggagaac ctgtgcggtg tgtagagggt gctgtgagcc acctccagcc tcgggtggct    180
gcttaagtaa ctttcaactc ctctcttctt aacactatga agtgtctcgg gaagcgcagg    240
ggccaggcag ctgctttcct gcctctttgc tggctctttt tgaagattct gcaaccgggg    300
```

-continued

```
cacagccacc tttataacaa ccgctatgct ggtgataaag tgataagatt tattcccaaa      360
acagaagagg aagcatatgc actgaagaaa atatcctatc aacttaaggt ggacctgtgg      420
cagcccagca gtatctccta tgtatcagag ggaacagtta ctgatgtcca tatcccccaa      480
aatggttccc gagccctgtt agccttctta caggaagcca acatccagta caaggtcctc      540
atagaagatc ttcagaaaac actggagaag ggaagcagct tgcacaccca gagaaaccga      600
agatccctct ctggatataa ttatgaagtt tatcactcct tagaagaaat tcaaaattgg      660
atgcatcatc tgaataaaac tcactcaggc ctcattcaca tgttctctat tggaagatca      720
tatgagggaa gatgtctttt tattttaaag ctgggcagac gatcacgact caaaagagct      780
gtttggatag actgtggtat tcatgcaaga gaatggattg gtcctgcctt ttgtcagtgg      840
tttgtaaaag aagctcttct aacatataag agtgacccag ccatgagaaa aatgttgaat      900
catctatatt tctatatcat gcctgtgttt aacgtcgatg gataccattt tagttggacc      960
aatgatcgat tttggagaaa aacaaggtca aggaactcaa ggtttcgctg ccgtggagtg     1020
gatgccaata gaaactggaa agtgaagtgg tgtgatgaag gagcttctat gcacccttgt     1080
gatgacacat actgtggccc ttttccagaa tctgagccgg aagtgaaggc tgtagctaac     1140
ttccttcgaa aacacagaaa gcacattagg gcttatctct cctttcatgc atatgctcag     1200
atgttactgt atccctattc ttacaaatat gcaacaattc ccaattttag atgtgtggaa     1260
tctgcagctt ataaagctgt gaatgcactt cagtcagtat acggggtacg atacagatat     1320
ggaccagcct ccacaacgtt gtatgtgagc tctggtagct caatggattg ggcctacaaa     1380
aatggaatac cttatgcatt tgctttcgaa ctacgtgaca ctggatattt tggatttta      1440
ctcccagaga tgctcatcaa acccacctgt acagaaacta tgctggctgt gaaaaatatc     1500
acaatgcacc tgctaaagaa atgtccctga gacagcccaa ggctcaggtc aactgccata     1560
ggattctgag caaggcctac ttggccctgg atagaaattg tttcaaaga gaagggcagc      1620
tgcttagagt gaacatgtct atggacttta aaaagacccc acgcaatttg actttgtggc     1680
aatagaaaac agtaaaaaac agggcatagc ctagtttgtt ataagaaaaa gcatccattt     1740
tctatccttt tagagtctta tttgattatg gtgggaggga atgttttcaa atttcccatt     1800
tctcaagaaa tgttcatatt aattgaggat ttcccttcaa taaatctcat gtcctcaatt     1860
ataaaaaaaa aaaaaaaaaa aaaaaaaaaa aaaaaaaaaa aaaaaa                    1906
```